US008461414B2

(12) United States Patent
Yoshizumi et al.

(10) Patent No.: US 8,461,414 B2
(45) Date of Patent: Jun. 11, 2013

(54) GENE HAVING ENDOREDUPLICATION PROMOTING ACTIVITY

(75) Inventors: Takeshi Yoshizumi, Yokohama (JP); Minami Matsui, Yokohama (JP); Takanari Ichikawa, Yokohama (JP); Miki Nakazawa, Yokohama (JP); Mika Kawashima, Yokohama (JP); Naoki Takahashi, Yokohama (JP); Chika Akagi, Yokohama (JP); Hiroko Hara, Yokohama (JP); Yuko Tsumoto, Yokohama (JP)

(73) Assignee: Riken, Wako-shi (JP)

( * ) Notice: Subject to any disclaimer, the term of this patent is extended or adjusted under 35 U.S.C. 154(b) by 439 days.

(21) Appl. No.: 12/593,304

(22) PCT Filed: Sep. 27, 2007

(86) PCT No.: PCT/JP2007/069418
§ 371 (c)(1), (2), (4) Date: Sep. 28, 2009

(87) PCT Pub. No.: WO2008/120410
PCT Pub. Date: Oct. 9, 2008

(65) Prior Publication Data

US 2010/0199387 A1 Aug. 5, 2010

(30) Foreign Application Priority Data

Mar. 28, 2007 (JP) ................................ 2007-085500

(51) Int. Cl.
*C12N 15/82* (2006.01)
*A01H 5/00* (2006.01)

(52) U.S. Cl.
USPC ............ 800/278; 435/419; 435/468; 800/298

(58) Field of Classification Search
None
See application file for complete search history.

(56) References Cited

U.S. PATENT DOCUMENTS

2004/0216190 A1 10/2004 Kovalic

OTHER PUBLICATIONS

Yoshizumi T. et al. Increased level of polyploidy1, a conserved repressor of CYCLINA2 transcription, controls endoreduplication in *Arabidopsis*. Plant Cell. Oct. 2006;18(10):2452-68. Epub Sep. 29, 2006.*

Verkest et al. The cyclin-dependent kinase inhibitor KRP2 controls the onset of the endoreduplication cycle during *Arabidopsis* leaf development through inhibition of mitotic CDKA;1 kinase complexes. Plant Cell. Jun. 2005;17(6):1723-36. Epub Apr. 29, 2005.*

Tabata et al., Uniprot Accession No. Q9FNN3, Mar. 1, 2001.*

Ichikawa et al. Sequence database of 1172 T-DNA insertion sites in *Arabidopsis* activation-tagging lines that showed phenotypes in T1 generation. Plant J. Nov. 2003;36(3):421-9.*

Nakazawa et al. Activation tagging, a novel tool to dissect the functions of a gene family. Plant J. Jun. 2003;34(5):741-50.*

Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*

Sugimoto-Shirasu et al. "Big it up": endoreduplication and cell-size control in plants. Curr Opin Plant Biol. Dec. 2003;6(6):544-53.*

Yoshizumi et al. Increased level of polyploidy1, a conserved repressor of CYCLINA2 transcription, controls endoreduplication in *Arabidopsis*. Plant Cell. Oct. 2006;18(10):2452-68. Epub Sep. 29, 2006.*

Yoshizumi, Takeshi et al., "Increased Level of Polyploidy1, a Conserved Repressor of CYCLINA2 Transcription, Controls Endoreduplication in *Arabidopsis*", The Plant Cell, vol. 18, No. 10, pp. 2452-2468, Oct. 2006.

Yoshizumi, Takeshi et al., "Saibo Bunretsu no Nai Saibo Shuki 'Endoreduplication' o Yokusei suru Idenshi no Hakken", Bionics, vol. 4, No. 2, pp. 74 to 76, Feb. 1, 2007, (with partial English translation).

Yoshizumi, Takeshi et al., "*Arabidopsis thaliana* no Shinki na Tensha Yokusei Inshi de aru ILP1 wa CyclinA2 no Tensha o Yokusei suru Koto de Endoreduplication o Sokushin suru", The Japanese Society of Plant Physiologists, p. 268, P103 (649), May 1, 2006, (with partial English translation).

Takahashi, Naoki et al., "*Arabidopsis thaliana* no ILP5 wa Endoreduplication o Sei ni Seigyo suru", The Japanese Society of Plant Physiologists, p. 268, P102 (648), May 1, 2006, (with partial English translation).

Yoshizumi, Takeshi et al., "Endoreduplication o Sei ni Seigyo suru Inshi ILP1 wa CyclinA2 no Tensha o Yokusei suru", The Japanese Society of Plant Physiologists, p. 161, 2aD05 (280), Mar. 15, 2007, (with partial English translation).

Yoshizumi, Takeshi et al., "*Arabidopsis thaliana* no Shinki na Tensha Yokusei Inshi de aru ILP1 wa CyclinA2 no Tensha o Yokusei suru Koto de Endoreduplication o Sokushin suru", The 27th Annual Meeting of the Molecular Biology Society of Japan, p. 554, 1PB-220, (2004), (with partial English translation).

(Continued)

*Primary Examiner* — Cynthia Collins
(74) *Attorney, Agent, or Firm* — Oblon, Spivak, McClelland, Maier & Neustadt, L.L.P.

(57) ABSTRACT

This invention is intended to identify a gene that regulates endoreduplication in a plant and to use such gene for breeding aimed at increasing the crop size. This invention provides a gene encoding an *Arabidopsis thaliana*-derived protein having an amino acid sequence as shown in SEQ ID NO: 2, 4, 6, 8, 10, or 12, which has endoreduplication promoting activity, a transgenic plant into which such gene has been introduced, thereby increasing the nuclear DNA content in the cells of such plant, and a method of using such gene to increase the size of the entire plant or a part thereof.

9 Claims, 34 Drawing Sheets

OTHER PUBLICATIONS

Takahashi, Naoki et al., "*Arabidopsis thaliana* no ILP5 wa Endoreduplication o Sei ni Seigyo suru", $27^{th}$ Annual Meeting of the Molecular Biology Society of Japan, p. 554, 1PB-217, (2004), (with partial English translation).

Yoshizumi, T. et al., "Increased Level of Polyploidyl, a Conserved Repressor of CYCLINA2 Transcription, Controls Endoreduplication in *Arabidopsis*", Plant Cell, Total 4 pages, (2006).

Extended European Search Report issued May 3, 2011, in Application No. / Patent No. 10015052.3-2403.

Database EMBL [online], "*Arabidopsis thaliana* clone C104780 unknown protein (At5g56790) mRNA, complete cds", XP002632886, Oct. 24, 2002, retrieved from EBI accession No. EM_PL:BT000971, Database accession No. BT000971, 2 pages.

Database EMBL [online], "*Arabidopsis thaliana* unknown protein (At5g56790) mRNA, complete cds.", XP002632885, retrieved from EBI accession No. EM_PL :AY056259, Database accession No. AY056259, 2 pages, Nov. 14, 2006.

Database UniProt [Online], "SubName: Full=Putative uncharacterized protein At5g56790;", XP002632887, retrieved from EBI accession No. UniProt : Q8H0Z8, Database accession No. Q8H0Z8, 1 page, Feb. 6, 2007.

Database UniProt [Online], "SubName : Full=Putative uncharacterized protein At5g56790;", XP002632888, retrieved from EBI accession No. UniProt: Q93ZU1, Database accession No. Q93ZU1, 1 page, Feb. 6, 2007.

Database GenBank [online], T. Yoshizumi, et al., "*Arabidopsis thaliana* ILP1 mRNA for transcriptional repressor ILP1, complete cds", GeoBank AB253763.1, FASTA Graphics, *Arabidopsis thaliana* (thale cress), <http://www.ncbi.nlm.nih.gov/entrez/viewer.fcgi?117413995:DDBJ:6048014>, Nov. 2, 2006, 3 pages.

* cited by examiner

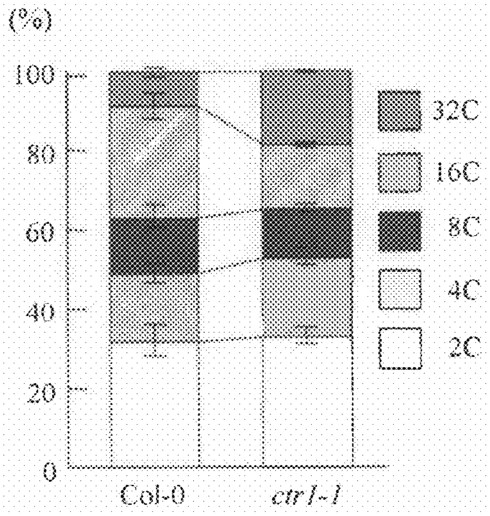
Fig. 1B
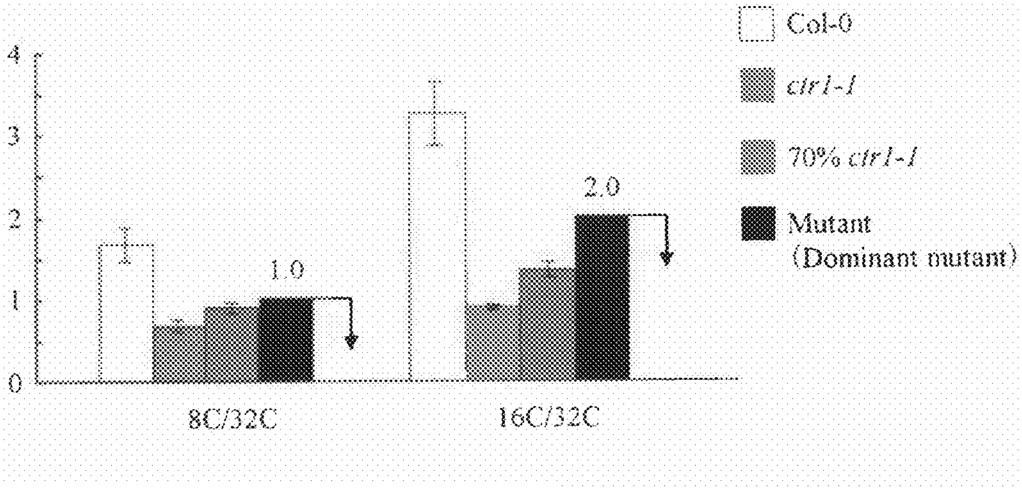

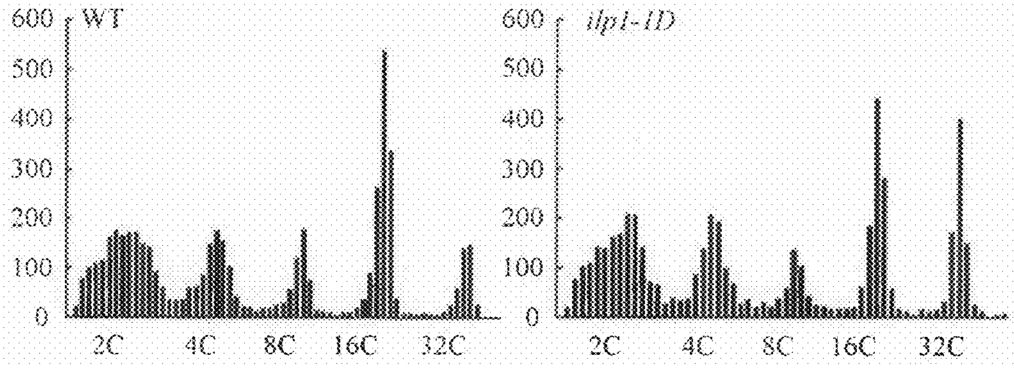
Fig. 2B
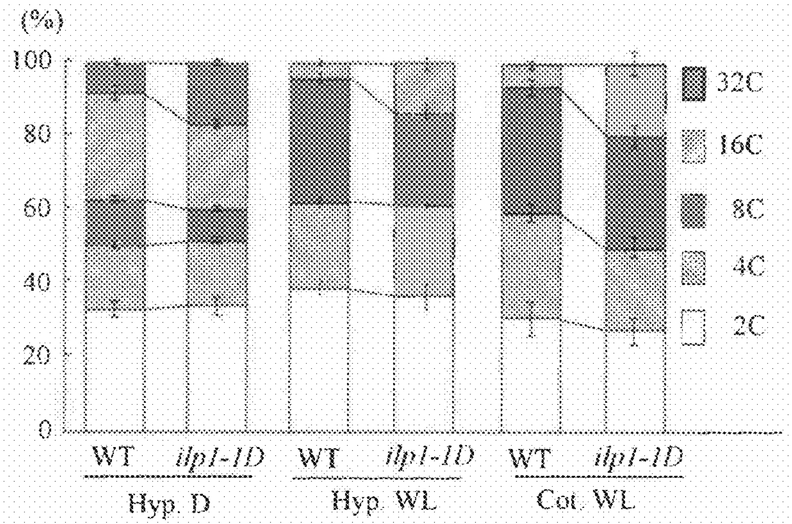

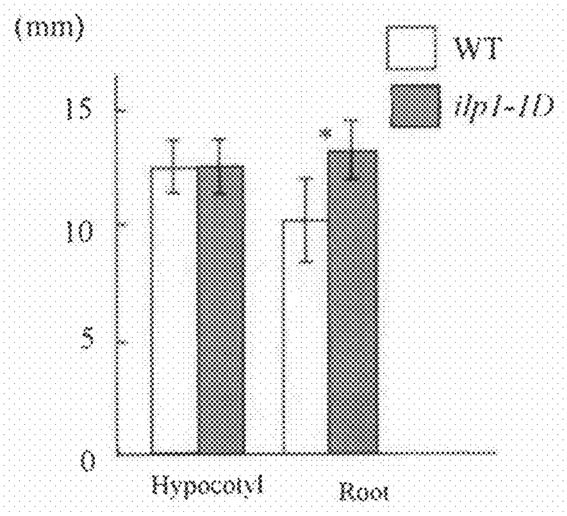
Fig. 2G
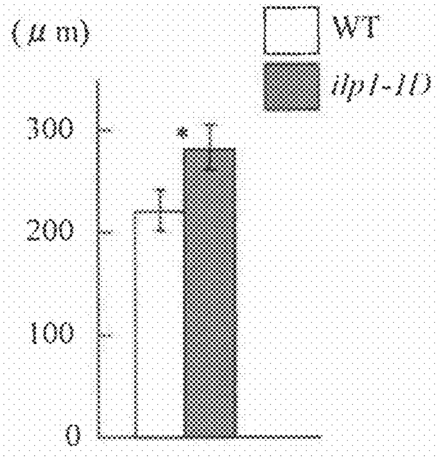

Fig. 3D

MGSNRPKNFRRRGDDGGDEIDGKVATPSSKPTST
LSSSKPKTLSASAPKKKLLSFADDEEEEEDGAPR
VTIKPKNGRDRVKSSSRLGVSGSSHRHSSTKERR
PASSNVLPQAGSYSKEALLELQKNTRTLPYSRSS
ANAEPKVVLKGLIKPPQDHEQQSLKDVVKQVSDL
DFDEEGEEEQHEDAFADQAAIIRAKKERMRQSRS
APAPDYISLDGGIVNHSAVEGVSDEDADFQGIFV
GPRPQKDDKKGVFDFGDENPTAKETTTSSIYEDE
DEEDKLWEEEQFKKGIGKRMDEGSHRTVTSNGIG
VPLHSKQQTLPQQQPQMYAYHAGTPMPNVSVAPT
IGPATSVDTLPMSQQAELAKKALKDNVKKLKESH
AKTLSSLTKTDENLTASLMSITALESSLSAAGDK
YVFMQKLRDFISVICDFMQNKGSLIEEIEDQMKE
LNEKHALSILERRIADNNDEMIELGAAVKAAMTV
LNKHGSSSSVIAAATGAALAASTSIRQQMNQPVK
LDEFGRDENLQKRREVEQRAAARQKRRARFENKR
ASAMEVDGPSLKIEGESSTDESDTETSAYKETRD
SLLQCADKVFSDASEEYSQLSKVKARFERWKRDY
SSTYRDAYMSLTVPSIFSPYVRLELLKWDPLHQD
VDFFDMKWHGLLFDYGKPEDGDDFAPDDTDANLV
PELVEKVAIPILHHQIVRCWDILSTRETRNAVAA
TSLVTNYVSASSEALAELFAAIRARLVEAIAAIS
VPTWDPLVLKAVPNTPQVAAYRFGTSVRLMRNIC
MWKDILALPVLENLALSDLLFGKVLPHVRSIASN
IHDAVTRTERIVASLSGVWTGPSVTRTHSRPLQP
LVDCTITLRRILEKRLGSGLDDAETTGLARRLKR
ILVELHEHDHAREIVRTFNLKEAV

Fig. 3E

```
                     . . . .10 . . . .20 . . . .30 . . . .40 . . . .50 . . . .60
ILP1        366:....KESHAKTLSSLTKTDENLTASLMSITAIESSLSAAGDKYVFMQKLRDFISVICDF:421
AT5g09210   154:...PQEQPQMYAGRPEELAKEPDENLTMSIAAAESCPSAPVYKYASLQEISDFKSVFRNF:211
Human       401:...SMKELHKTNRQQHEKHLQSRVDSTRAIERLEGSSGGIGERYKFLQEMRGYVQDLLEC:458
Mouse       340:....KELHKTNQQQHEKHLQSRVDSTRAIERLEGSSGGIGERYKFLQEMRGYVQDLLEC:395
HumanGCF1   281:RLTLLQETHRSHLREYEKYVQDVKSSKSTIQNLESSSN.QALNCKFYKSMKIYVENLIDC:340
consensus     1:-----**-***------**-**----**-*!--*!***-*-***********-**--****: 60

                     . . . .70 . . . .80 . . . .90 . . . 100 . . . 110 . .
ILP1        422:MQNKGSLIEEIEDQMKELNEKHALSILERRIADNNDEMIELGAAVKAAMTVLNKH:476
AT5g09210   212:MQGICVAFVCVSGAFISIKRLLSIFFLSQKNGYLITAIEDQMKVDGYSLI.....:261
Human       459:FSEKVPLINELESAIHQLYKQRASRLVQRRQDDIKDESSEFSS............:501
Mouse       396:FSEKVPLINELESAIHQLYKQRASRLVQRRQDDIKDESSEFSSHS..........:440
HumanGCF1   341:LNEKIINIQEIESSMHALLLKQAMTFMKRRQ........................:371
consensus    61:*****-**********-*-*-***-**-***-**-**--*---------------:115
```

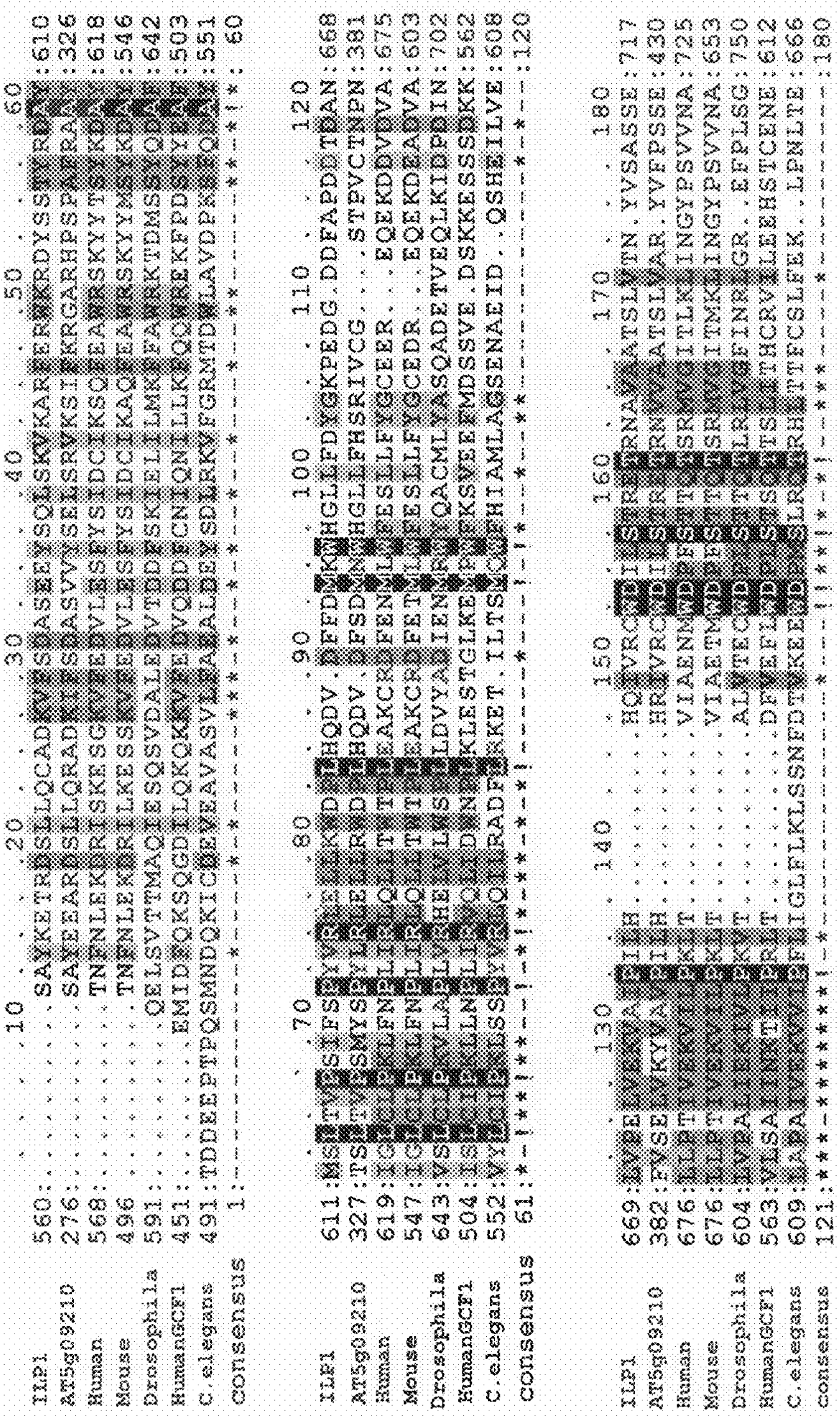

Fig. 3F

```
ILP1       560:..........SAYKETRISLLQCADXVSHASEEISQISKYKARERWKRDYSSXRXM:610
AT5g09210  276:..........SAYEEARDSLLQRADXTSHASVVISELSRYKSIRKRGARHSPXMRAX:326
Human      568:..........TNFNLEKDRISKESGXEVLESFYSIDCIKSQEEAMRSKYYTSKDX:618
Mouse      496:..........TNFNLEKMRILKESSXEDVLESFYSIDCIKAQEAMRSKYYMSKDX:546
Drosophila 591:..........QELSVTTMAQIESQSVDALEXVTDDRSKIELILMKFARRKTDMSXQQX:642
HumanGCF1  451:..........EMIDMQKSQGDILQKQKXMVEDVQDDFCNIQNILLKQQMREKFPDSXYX:503
C.elegans  491:TDDEEPTPQSMNDQKICMEVEAVASVLXAXALBEISDIRKVFGRMTDXLAVDPKXMQ:551
consensus    1:----------------|**|**    *      *   |*  *|*:       :60

ILP1       611:MSXTTXCSIFSXTXXEXKD.HQDV.DFFDXRKXHGLIFDXGKPEDG.DDFAPDDTDAN:668
AT5g09210  327:TSXTTXSMYSPXLRXEXRD.HQDV.FSDXNXHGLIFHSRIVCG...STPVCTNPN:381
Human      619:IGXPFXFNELXRXQXTT.EAKCRXFENLLXESLLFYGCEER..EQEKDDVDVA:675
Mouse      547:IGXPFXFNELXRXQXTT.EAKCRXFETLLXESLLFYGCEDR..EQEKDZADVA:603
Drosophila 643:VSXPVLAXIXHEXLXS.LDVYALIENXRXXQACMLYASQADETVEQLKIDPDIN:702
HumanGCF1  504:ISXPKLLNXIXQXDN.KLESTGLKE.PXEKSVEEEMDSSVE.DSKKESSSDKK:562
C.elegans  552:VIXISSYXEQXRADFXRKET.ILTSXLEFHIAMLAGGSENAEID..QSHEILVE:608
consensus   61:*-|**|*                                  :120

ILP1       669:XVXEXXXAXIXH........HQXVRCXISRXRNAXATSLXTN.YVSASSE:717
AT5g09210  382:FVSEIXKYXAXIXH........HRXVRCXISTRXRMXATSLXAR.YVFPSSE:430
Human      676:XPXTXVXXXKXT........VIAENMXEXTSRXXITLKXINGYPSVVNA:725
Mouse      604:XHXTXVXXXKXT........VIAETMXXTSRXXITMKXINGYPSVVNA:653
Drosophila 604:DVRAXXXXEXKXT........ALXTECXXLLRXXFINPXGR..EFPLSG:750
HumanGCF1  563:VLSAXXNTX........DFXEFLXXDLRXLEEHSTCENE:612
C.elegans  609:LAXAXXXXXXXXFXIGLFLKLSSNFDTXKEEXDLRXRHXTTFCSLFEX..LPNLTE:666
consensus  121:-----|*                                  :180
```

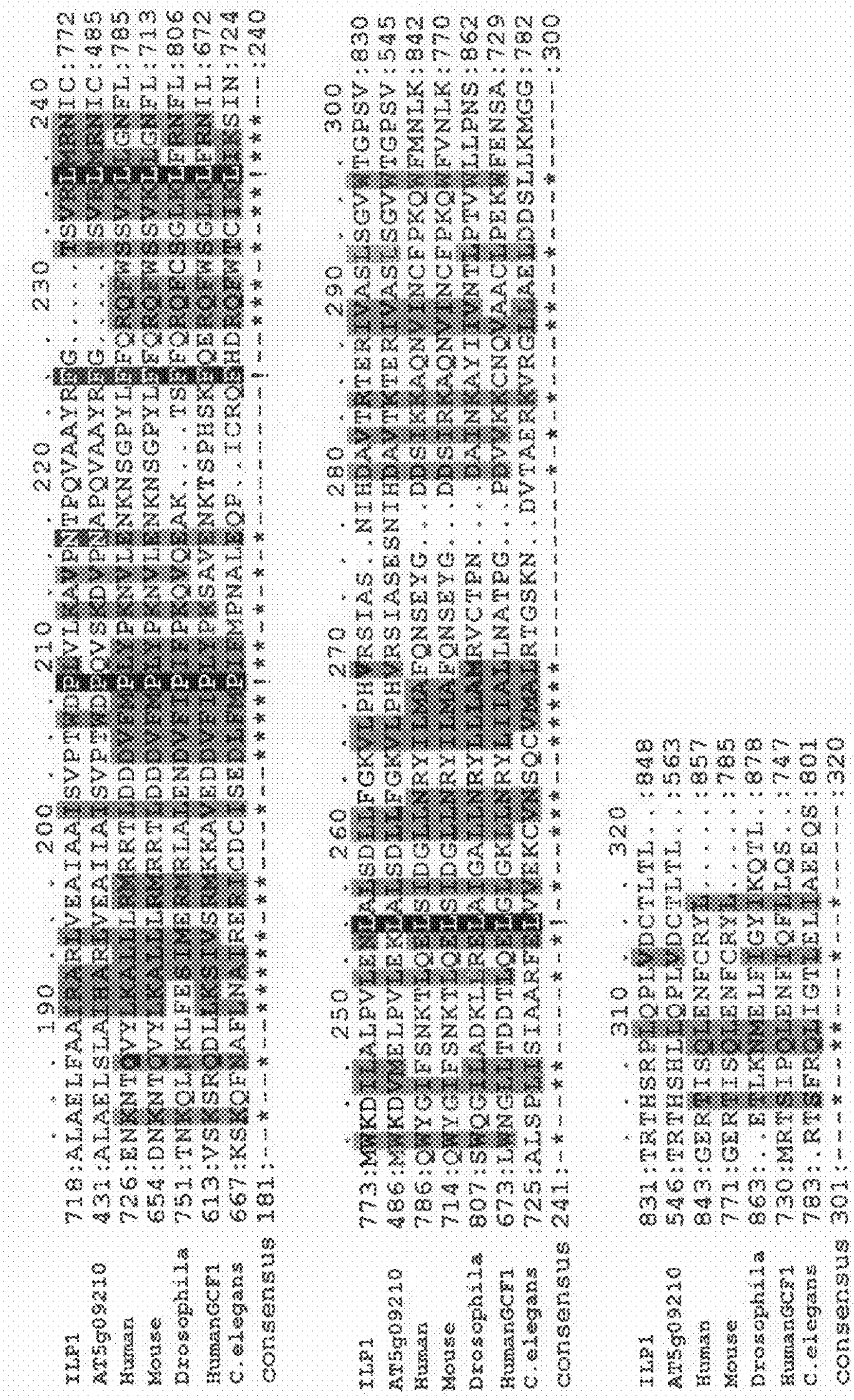

Fig. 3F (continued)

```
ILP1           718:ALAELFAA..RVEAIAA SVPT  VLAA P TPQVAAYR G....  S    IC:772
At5g09210      431:ALAELSLA..RVEAIIA SVPT  QVS D P APQVAAYR G....  S    IC:485
Human          726:ENKNTQVY..L RRT DD   N L NKNSGPYLFQ    S    GNFL:785
Mouse          654:DNKNTQVY..L RRT DD   N L NKNSGPYLFQ    S    GNFL:713
Drosophila     751:TNKQLKLFE..  RLA EN   KQ AK...TS FQ EC  G   FM FL:806
HumanGCF1      613:VS SR DL   S KKA ED   F  SAV NKTSPHSK QE       F  IL:672
C.elegans      667:KS QF AF N  RE  CDC SE L    MPNAL QP..ICRQ HD      SIN:724
consensus      181:---.*----.**.****.****.*.*...-*..**..*.******.:240

                    250       260       270       280       290       300
ILP1           773:M KD  ALPVEE  SD FGK PH RSIAS..NIHDA T TER ASLSGV TGPSV:830
At5g09210      486:M KD  ELPVIE A SD FGK PH RSIASESNIHDA T TER ASLSGV TGPSV:545
Human          786:Q YG  FSNKTIQ S DG RY .FQNSEYG..D S  AQN NCFPKQ FMNLK:842
Mouse          714:Q YG  FSNKTIQ S DG RY .FQNSEYG..D S  AQN NCFPKQ FVNLK:770
Drosophila     807:S QG  ADKLR    GA  RY L  RVCTPN... A N AYI NT PTV LLPNS:862
HumanGCF1      673:L NG  TDDTLQ  GK  RYL  LNATPG..P V  CNQ AAC PEN FENSA:729
C.elegans      725:ALSP  SIAARF   EKC SQC    RTGSKN..DVTAER VRG AEL DDSLIKMGG:782
consensus      241:-.**--.*--*.*.-*.**.*..*.--..*.*.--.**.*.**-:300

                    310       320
ILP1           831:TRTHSRP QPLI DCTLTL..:848
At5g09210      546:TRTHSHL QPLI DCTLTL..:563
Human          843:GER IS  ENFCRY......:857
Mouse          771:GER IS  ENFCRY......:785
Drosophila     863:..E LK  ELF GY KQTL.:878
HumanGCF1      730:MRTSIP  ENF QF LQS..:747
C.elegans      783:RT FR  IGT EL AEEQS:801
consensus      301:---.*----.***------:320
```

A

B

A

B

C

G

H

GENE HAVING ENDOREDUPLICATION PROMOTING ACTIVITY

The present application is a 35 U.S.C. §371 National Stage patent application of International patent application PCT/JP2007/069418, filed on Sep. 27, 2007, which claims priority to Japanese patent application JP 2007-085500, filed Mar. 28, 2007.

TECHNICAL FIELD

The present invention relates to a gene having endoreduplication promoting activity in a plant and a transgenic plant into which such gene has been introduced.

BACKGROUND ART

Endoreduplication is a type of cell cycle in which nuclear chromosome DNA duplication takes place without cell division. When endoreduplication is repeated, the nuclear DNA content (i.e., a nuclear phase) is doubled from the basic 2C, and cells having doubled 4C or 8C nuclear DNA content are produced. Cells are known to grow in response to an increase in the nuclear DNA content. Since the size of an organism is determined based on the number and the sizes of cells constituting an individual, endoreduplication is considered to be a mechanism that determines organism size.

Although endoreduplication is observed in several tissues in insects and mammals, this feature is a characteristic of plant organs, and it can serve to distinguish plant development from that of other organisms. In plants, many organs are composed of a mixture of cells of different ploidy levels, and this feature is prominent in hypocotyl elongation, leaf expansion, and endosperm development. These polyploid cells are commonly observed in various multicellular organisms, such as insects, mammals, and plants (Non-Patent Documents 1 and 2). Polyploid cells are often seen in various developing tissues and are correlated with development; hence, polyploidy is thought to be a marker of differentiation (Non-Patent Document 3).

Hypocotyl elongation of seedlings is a typical size increment caused by endoreduplication in *Arabidopsis thaliana*. Cells contain as much as 8C (C is a set of haploid chromosomes) of nuclear DNA in light-grown seedlings and as high as 16C in dark-grown seedlings (Non-Patent Document 4). The polyploidy levels in hypocotyls are also known to be controlled by phytohormones (Non-Patent Document 5). Constitutively triple response 1 (ctr1) is an ethylene signal transduction mutant in which the ethylene signal is constitutively activated and causes a triple response without exogenous ethylene (Kieber, J. J., Rothenberg, M., Roman, G, Feldmann, K. A., and Ecker, J. R., 1993, CTR1, a negative regulator of the ethylene response pathway in *Arabidopsis*, encodes a member of the raf family of protein kinases, *Cell* 72, 427-441), and ctr1 has increased polyploidy levels, as high as 32C, in hypocotyls of dark-grown seedlings (Non-Patent Document 6). This indicates that ethylene regulates endoreduplication positively in hypocotyl cells.

Endoreduplication is also involved in the development of a plant's organs. A trichome consists of a single cell that contains a nucleus of up to 32C (Non-Patent Document 7). Endoreduplication is also observed in endosperm, and there are several reports of the involvement of cell-cycle-related genes in endosperm expansion (Non-Patent Documents 8 and 9).

Thus, the regulation of endoreduplication plays an important role in plant development and differentiation.

To date, cell-cycle-related factors are known to control endoreduplication, and a representative example is cyclin. For example, the D-type cyclin gene CYCD3;1 expresses specifically in meristems and developing leaves in *Arabidopsis*. When CYCD3;1 is overexpressed, the polyploidy levels of transgenic plants are reduced and cell sizes become smaller (Non-Patent Document 10). This indicates that CYCD3;1 is involved in cell proliferation through inhibiting endoreduplication in plant tissue. Also, it is reported that an *Arabidopsis thaliana* A-type cyclin gene, CYCA2;1, is expressed in various cells, such as guard cells, where substantially no endoreduplication occurs (Non-Patent Documents 11 and 12). When tobacco (*Nicotiana tabacum*) CYCA3;2, which is also an A-type cyclin gene, is overexpressed in *Arabidopsis*, polyploidy levels are reduced in various tissues (Non-Patent Document 13). It is also reported that loss of *Arabidopsis thaliana* CYCA2;3 function increases polyploidy in mature true leaves (Non-Patent Document 14). In particular, accordingly, A-type cyclins can play an important role in regulating endoreduplication in plants.

Although there have been several research reports regarding endoreduplication as described above, the major part of the mechanism of endoreduplication in plants has not yet been elucidated. Thus, elucidation of such mechanism enables understanding of the mechanism of plant size determination, which in turn realizes various applications.

(Non-Patent Document 1) Edgar, B. A., and On-Weaver, T. L. (2001) Endoreplication cell cycles: more for less. Cell 105, 297-306.

(Non-Patent Document 2) Joubes, J., and Chevalier, C. (2000) Endoreduplication in higher plants. Plant Mol. Biol. 43, 735-745.

(Non-Patent Document 3) De Veylder, L., Beeckman, T., Beemster, G. T., Krols, L., Terras, F., Landrieu, I., van der Schueren, E., Maes, S., Naudts, M., and Inzé, D. (2001) Functional analysis of cyclin-dependent kinase inhibitors of *Arabidopsis*. Plant Cell 13, 1653-1668.

(Non-Patent Document 4) Gendreau, E., Traas, J., Desnos, T., Grandjean, O., Caboche, M., and Hofte, H. (1997) Cellular basis of hypocotyl growth in *Arabidopsis thaliana*. Plant Physiol. 114, 295-305.

(Non-Patent Document 5) Gendreau, E., Orbovic, V., Hofte, H., and Traas, J. (1999) Gibberellin and ethylene control endoreduplication levels in the *Arabidopsis thaliana* hypocotyl. Planta 209, 513-516.

(Non-Patent Document 6) Gendreau, E., Traas, J., Desnos, T., Grandjean, O., Caboche, M., and Hofte, H. (1997) Cellular basis of hypocotyl growth in *Arabidopsis thaliana*. Plant Physiol. 114, 295-305.

(Non-Patent Document 7) Melaragno, J. E., Mehrotra, B., and Coleman, A. W. (1993) Relationship between endopolyploidy and cell size in epidermal tissue of *Arabidopsis*. Plant Cell 5, 1661-1668

(Non-Patent Document 8) Sun, Y, Flannigan, B. A., and Setter, T. L. (1999) Regulation of endoreduplication in maize (*Zea mays* L.) endosperm. Isolation of a novel B1-type cyclin and its quantitative analysis. Plant Mol. Biol. 41, 245-258.

(Non-Patent Document 9) Larkins, B. A., Dukes, B. P., Dante, R. A., Coelho, C. M., Woo, Y. M., and Liu, Y. (2001) Investigating the hows and whys of DNA endoreduplication. J. Exp. Bot. 52, 183-192.

(Non-Patent Document 10) Dewitte, W., Riou-Khamlichi, C., Scofield, S., Healy, J. M., Jacqmard, A., Kilby, N. J., and Murray, J. A. H. (2003) Altered cell cycle distribution, hyperplasia, and inhibited differentiation in *Arabidopsis* caused by the D-type cyclin CYCD3. Plant Cell 15, 79-92

(Non-Patent Document 11) Melaragno, J. E., Mehrotra, B., and Coleman, A. W. (1993) Relationship between endopolyploidy and cell size in epidermal tissue of *Arabidopsis*. Plant Cell 5, 1661-1668.

(Non-Patent Document 12) Burssens, S., de Almeida Engler, J., Beeckman, T., Richard, C., Shaul, O., Ferreira, P., Van Montagu, M., and Inze, D. (2000) Developmental expression of the *Arabidopsis thaliana* CycA2;1 gene. Planta 211, 623-631.

(Non-Patent Document 13) Yu, Y, Steinmetz, S., Meyer, D., Brown, S., Shen, W. H. (2003). The tobacco A-type Cyclin, Nicta; CYCA3;2, at the nexus of cell division and differentiation. Plant Cell 15, 2763-2777.

(Non-Patent Document 14) Imai, K. K., Ohashi, Y, Tsuge, T., Yoshizumi, T., Matsui, M., Oka, A., and Aoyama, T. (2006) The A-Type Cyclin CYCA2;3 Is a Key Regulator of Ploidy Levels in *Arabidopsis* Endoreduplication. Plant Cell 18, 382-396.

DISCLOSURE OF THE INVENTION

An object of the present invention is, accordingly, to identify a gene that regulates endoreduplication in plants and to apply such gene to breeding aimed at crop size increase.

The present inventors have conducted concentrated studies in order to attain the above object. They screened for mutants with increased cell nuclear DNA contents via flow cytometric analysis from *Arabidopsis thaliana* activation tagging lines and they isolated several mutants that dominantly exhibit such phenotypes. In such mutants, DNA contents were found to increase in dark-grown and light-grown seedlings. Thus, they designated these mutants as exhibiting increased level of polyploidy 1-1D (ilp1-1D). Up to the present, 6 mutant lines (i.e., ilp1-1D, 2-D, 3-D, 4-D, 5-D, and 7-D) have been found in which the causative genes have been identified. Cell size increase is also observed in such mutant lines along with an increase in DNA contents. ilp1-1D is described below as an example of analysis. The causative gene (i.e., the ILP1 gene) was isolated by plasmid rescue, and the structure and functions thereof were analyzed. As a result, it was verified that overexpression of the ILP1 genes would result in expanded cotyledons and elongated seedlings, the ILP1 gene would encode a novel nuclear protein homologous to the C-terminal region of the mammalian GC binding factor (GCF), the nuclear protein would function as a transcriptional repressor in vivo, and the ILP1 gene would repress cyclin A2 expression in *Arabidopsis thaliana* and in mice. Cyclin A2 accelerates cell division after DNA duplication. Thus, it was considered that the ILP1 protein represses expression of the cyclin A2 gene, endoreduplication is consequently accelerated, and the nuclear DNA content is increased. The present invention has been completed based on such findings.

Specifically, the present invention includes the following inventions.

(1) A gene which is the following (a) to (c):
(a) a gene comprising DNA consisting of the nucleotide sequence as shown in SEQ ID NO: 1, 3, 5, 7, 9, or 11;
(b) a gene comprising DNA which hybridizes under stringent conditions to DNA consisting of a nucleotide sequence complementary to DNA consisting of the nucleotide sequence as shown in SEQ ID NO: 1, 3, 5, 7, 9, or 11 and which encodes a protein having endoreduplication promoting activity; or
(c) a gene comprising DNA which consists of a nucleotide sequence having 80% or higher homology to the nucleotide sequence as shown in SEQ ID NO: 1, 3, 5, 7, 9, or 11 and which encodes protein having endoreduplication promoting activity.

(2) A gene encoding a protein which is the following (d) to (f):
(d) a protein consisting of the amino acid sequence as shown in SEQ ID NO: 2, 4, 6, 8, 10, or 12;
(e) a protein consisting of an amino acid sequence derived from the amino acid sequence as shown in SEQ ID NO: 2, 4, 6, 8, 10, or 12 by deletion, substitution, or addition of one or several amino acids and having endoreduplication promoting activity; or
(f) a protein consisting of an amino acid sequence having 80% or higher homology to the amino acid sequence as shown in SEQ ID NO: 2, 4, 6, 8, 10, or 12 and having endoreduplication promoting activity.

(3) A protein which is the following (d) to (f):
(d) a protein consisting of the amino acid sequence as shown in SEQ ID NO: 2, 4, 6, 8, 10, or 12;
(e) a protein consisting of an amino acid sequence derived from the amino acid sequence as shown in SEQ ID NO: 2, 4, 6, 8, 10, or 12 by deletion, substitution, or addition of one or several amino acids and having endoreduplication promoting activity; or
(f) a protein consisting of an amino acid sequence having 80% or higher homology to the amino acid sequence as shown in SEQ ID NO: 2, 4, 6, 8, 10, or 12 and having endoreduplication promoting activity.

(4) A recombinant vector containing the gene according to (1) or (2).

(5) A transgenic plant with an increased nuclear DNA content in a plant cell into which the gene according to (1) or (2) or the recombinant vector according to (4) has been introduced.

(6) The transgenic plant with an increased nuclear DNA content in a plant cell according to (5), wherein the plant is a plant body, a plant organ, a plant tissue, or a cultured plant cell.

(7) A method for producing a transgenic plant with an increased nuclear DNA content in a plant cell comprising introducing the gene according to (1) or (2) or the recombinant vector according to (4) into a plant cell and reproducing a plant body from the plant cell.

(8) A method for increasing the size of the entire plant body or a part thereof by overexpressing the gene according to (1) or (2) in the plant body.

BRIEF DESCRIPTION OF THE DRAWINGS

FIG. 1A shows the relative ratio of cell ploidy of a wild-type (Col-0) and ctr1-1. Approximately 5,000 nuclei were counted in the wild-type (Col-0) and in the ctr1-1 mutant.

FIG. 1B shows a ratio of 8C/32C and 16C/32C of dark-grown seedlings of wild type (Col-0), ctr1-1, and a mixture of Col-0 and ctr1-1 at a ratio of 3:7. Black bars indicate the categories used for mutant screening. For each ploidy measurement, at least 20 seedlings were used and measurement was replicated 3 times. Error bars indicate standard deviations.

Figure 2C:
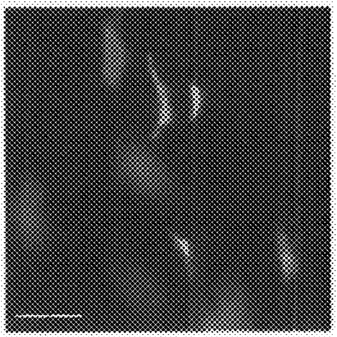
FIG. 2A shows histograms of ploidy levels of hypocotyl cells of 7-day-old dark-grown seedlings: left panel: wild-type; right panel: homozygous ilp1-1D; X axis: nuclear ploidy; and Y axis: cell count. Approximately 5,000 nuclei were counted in wild-type and ilp1-1D.
FIG. 2B shows the relative ratio of each cell ploidy for dark- and light-grown wild-type and ilp1-1D. At least 20 seedlings were used for ploidy analysis and analysis was replicated 3 times. (Hyp. D): hypocotyls cells of dark-grown seedlings; (Hyp. WL); hypocotyls cells of light-grown seedlings; and (Cot. WL); cotyledon cells of light-grown seedlings. Approximately 3,000 to 5,000 nuclei were counted in wild-type and ilp1-1D.

FIG. 2C shows DAPI staining of nuclei of the lower part of the hypocotyls of wild-type seedlings.

Figure 2D:
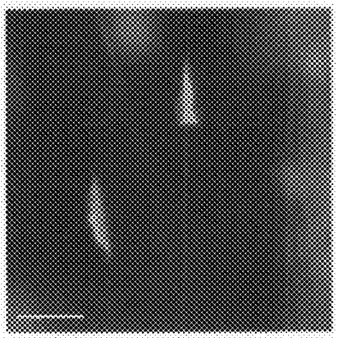

FIG. 2D shows DAPI staining of nuclei of the lower part of the hypocotyl of ilp1-1D.

Figure 2E:
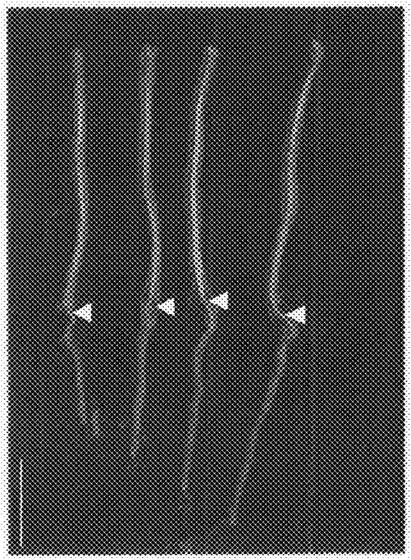

FIG. 2E shows morphology of 7-day-old dark-grown wild-type seedlings (2 seedlings on the left) and ilp1-1D seedlings (2 seedlings on the right). A white arrow indicates the junction of a hypocotyl and a root.

FIG. 2F shows hypocotyl and root length of 7-day-old dark-grown wild-type seedlings and ilp1-1D seedlings.

FIG. 2G shows the diameters of hypocotyls of 7-day-old dark-grown wild-type seedlings and ilp1-1D seedlings.

Figure 2H:
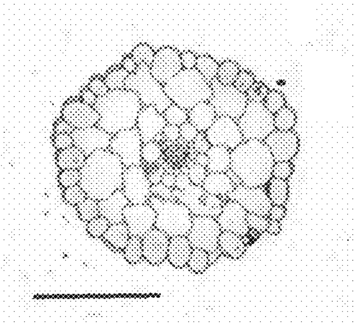

FIG. 2H shows transverse sections of hypocotyls of dark-grown wild-type seedlings.

Figure 2I:
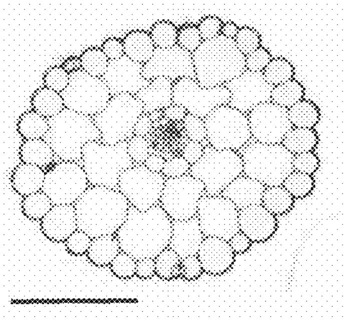

FIG. 2I shows transverse sections of hypocotyls of dark-grown ilp1-1D.

Figure 2J:
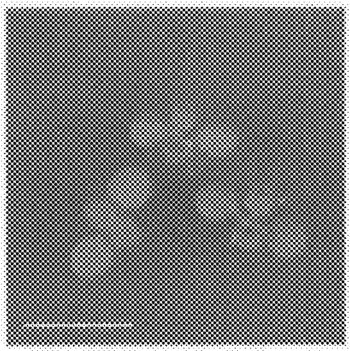

FIG. 2J shows cotyledons of 7-day-old light-grown wild-type seedlings.

Figure 2K:
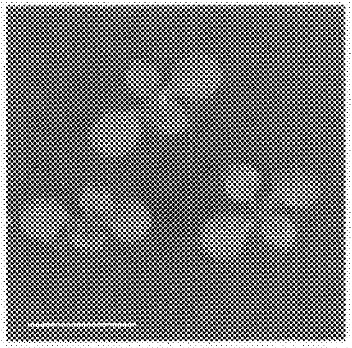

FIG. 2K shows cotyledons of 7-day-old light-grown ilp1-1D.

Figure 2L:
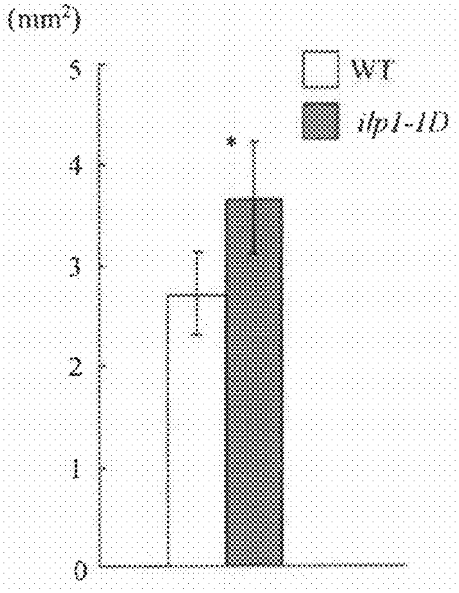

FIG. 2L shows cotyledonal areas of 7-day-old light-grown wild-type and ilp1-1D seedlings.

(In FIGS. 2F, 2G, and 2L, at least 20 seedlings were subjected to measurement. Bars shown in FIGS. 2B, 2F, 2Q and 2L indicate standard deviations. Bars shown in FIGS. 2C and 2D are 10 μm, bars shown in FIGS. 2E, 2J, and 2K are 5 mm, and bars shown in FIGS. 2H and 2I are 100 μm. Student's t-test: *0.001>p versus wild-type in FIGS. 2F, 2G and 2L)

Figure 3A:
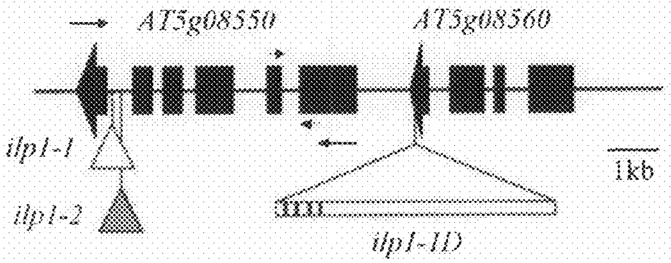

FIG. 3A shows T-DNA insertion sites in ilp1-1D. Triangles with bars indicate the activation tagging T-DNA insertion sites in ilp 1-1D. Black lines on the bars indicate the four copies of the CaMV 35S enhancers near the RB. Small white and gray triangles indicate the T-DNA insertion sites of ilp1-1 (SALK_030650) and ilp1-2 (SALK_135563), respectively. Short arrows indicate primer positions for real-time PCR in FIGS. 3B and 6C, and long arrows indicate primer positions for semi-quantitative RT-PCR in FIG. 4B.

Figure 3B:
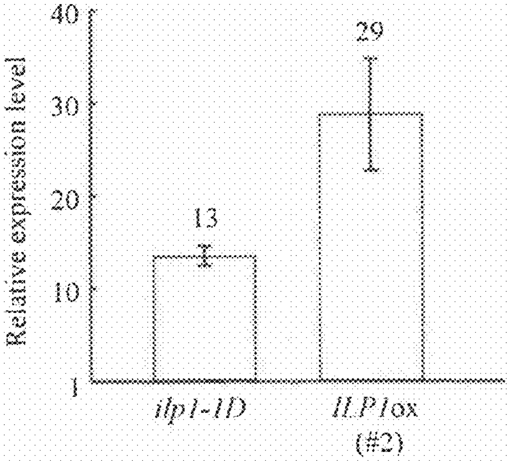

FIG. 3B shows real-time PCR analysis showing expression of AT5g08550 (ILP1) in wild-type (Col-0), ilp1-1D, and ILP1ox seedlings. Relative expression levels: expression levels of the ILP1 genes in ilp1-1D and AT5g08550 (ILP1) overexpressing lines (#2) (ILP1ox) relative to wild-type seedlings. Error bars indicate standard deviations.

Figure 3C:
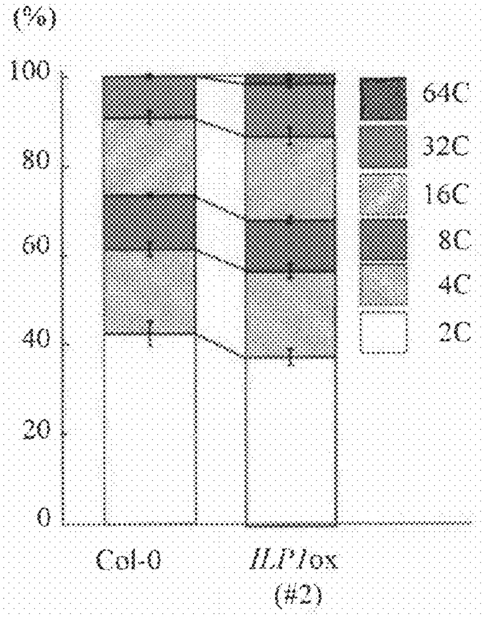

FIG. 3C shows the relative ratio of each cell ploidy for dark-grown wild type (Col-0) and ILP1ox (#2) seedlings. Approximately 5,000 nuclei were counted in wild type and ILP1ox seedlings.

FIG. 3D shows the amino acid sequence of the ILP1 protein (SEQ ID NO: 2). The box with the broken line indicates motif 1 and the box with the solid line indicates motif 2. Bold letters indicate putative nuclear localization signals (NLS).

FIG. 3E shows an alignment of ILP1 motif 1 and its homologs. The ILP1 motif 1 (SEQ ID NO: 50) was aligned with similar regions of other proteins; *Arabidopsis thaliana* (AT5g09210) (SEQ ID NO: 51), human (AAK68721) (SEQ ID NO: 52), mouse (AAK68725) (SEQ ID NO: 53), and human GCF1 (AAA35598) (SEQ ID NO: 54). The amino acid identity and homology between the ILP1 motif 1 and its homologs are 38% and 42% for *Arabidopsis thaliana,* 27% and 48% for human, 27% and 48% for mouse, and 28% and 52% for human GCF1.

FIG. 3F shows an alignment of ILP1 motif 2 and its homologs. ILP1 Motif 2 (SEQ ID NO: 55) was aligned with similar regions of other proteins; *Arabidopsis thaliana* (AT5g09210) (SEQ ID NO: 56), human (AAK68721) (SEQ ID NO: 57), mouse (AAK68725) (SEQ ID NO: 58), *Drosophila* (AAF54074) (SEQ ID NO: 59), human GCF1 (AAA35598) (SEQ ID NO: 60), and *C. elegans* (NP492341) (SEQ ID NO: 61). All alignments were performed using clustalW and Mac Boxshade software. The amino acid identity and homology between ILP1 motif 2 and its homologs are 72% and 77% for *Arabidopsis thaliana,* 27% and 45% for human, 27% and 44% for mouse, 28% and 48% for *Drosophila,* 22% and 43% for human GCF1, and 25% and 44% for *C. elegans.*

(In FIGS. 3E and F, gray letters indicate functionally conserved amino acid residues in at least 3 members. White letters with a black background indicate conserved amino acid residues in all members.)

Figure 3G:
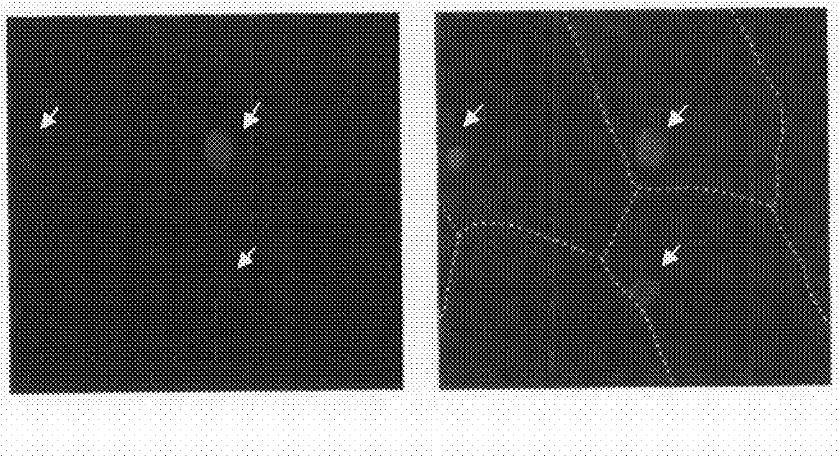

FIG. 3G shows localization of ILP1:GFP. The left panel indicates fluorescence of ILP1:GFP. The right panel indicates a DAPI-stained nuclear image. Triangular arrows indicate nuclei. The experiment was replicated 3 times.

Figure 3H:
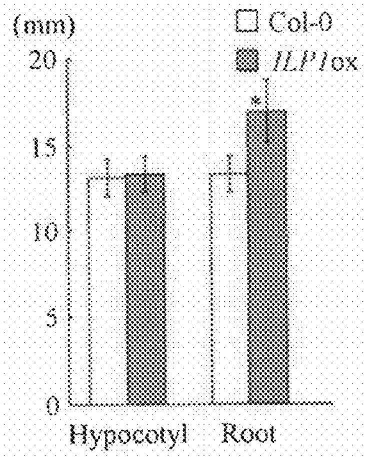

FIG. 3H shows elongation of taproots of dark-grown ILP1-overexpressing seedlings (ILP1ox). Error bars indicate standard deviations.

Figure 3I:
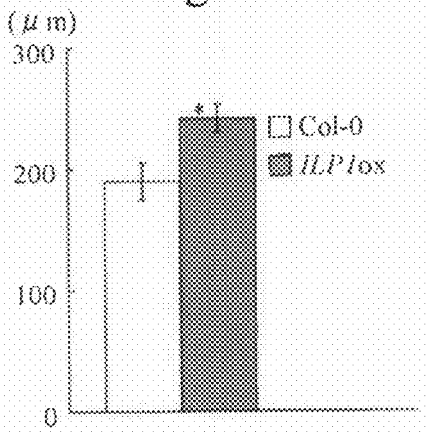

FIG. 3I shows diameters of hypocotyls of the dark-grown ILP1-overexpressing seedlings (ILP1ox). Error bars indicate standard deviations.

Figure 3J:
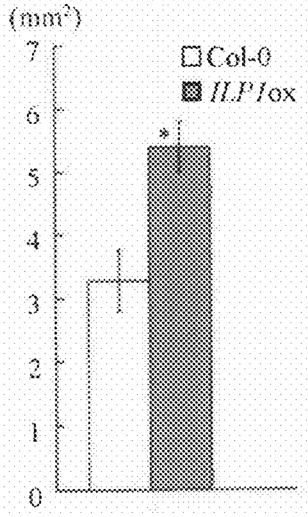

FIG. 3J shows the cotyledonal area of the light-grown ILP4-overexpressing seedlings (ILP4ox). Error bars indicate standard deviations.

Figure 4A:
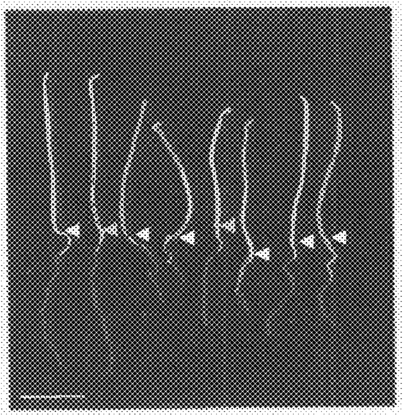

FIG. 4A shows morphology of dark-grown wild-type, ilp1-1, and ilp1-2 seedlings. Seedlings were grown for 5 days. The pairs of seedlings from left to right are wild-type, ilp1-1, heterozygotes of ilp1-1 and ilp1-2, and ilp1-2, respectively. Isogenic wild-type siblings of ilp1-1 were used as wild-type seedlings. The same result was obtained from wild-type siblings of ilp1-2. A white triangular arrow indicates the junction of a hypocotyl and a root.

Figure 4B:
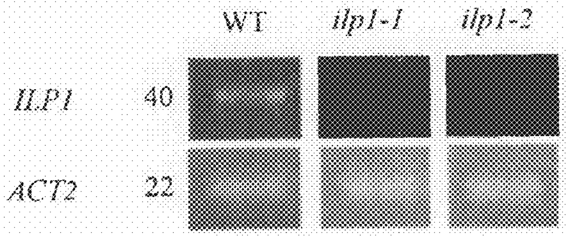

FIG. 4B shows semi-quantitative RT-PCR for the expression of ILP1. The numbers on the left indicate the numbers of PCR cycles. ACT2 was used as a control.

Figure 4C:
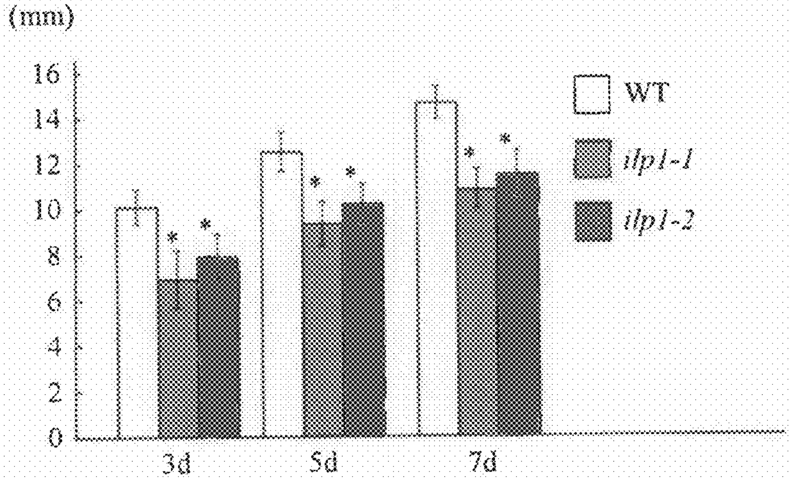

FIG. 4C shows the hypocotyl length of 3, 5, and 7-day-old dark-grown wild-type, ilp1-1, and ilp1-2 seedlings.

Figure 4D:
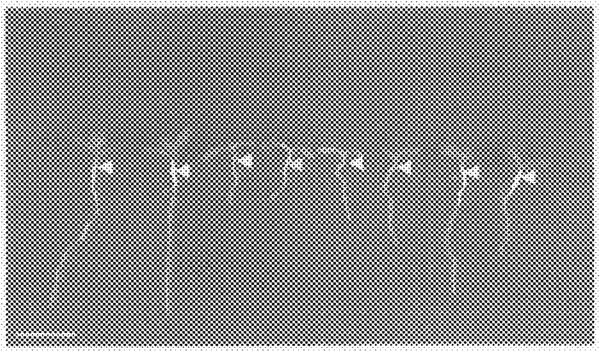

FIG. 4D shows 7-day-old light-grown seedlings. The alignment of seedlings is the same as in FIG. 4A. A white arrow indicates the junction of a hypocotyl and a root.

Figure 4E:
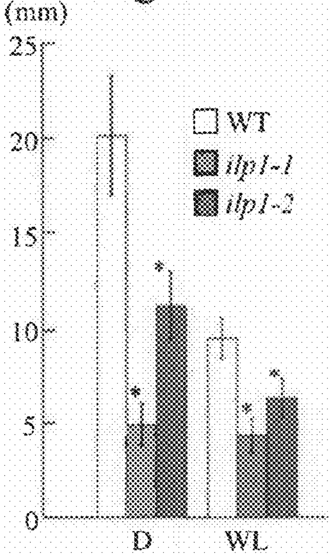

FIG. 4E shows the root length of 7-day-old dark- or light-grown wild-type, ilp1-1, and ilp1-2 seedlings. (D: darkness; WL: white light)

Figure 4F:
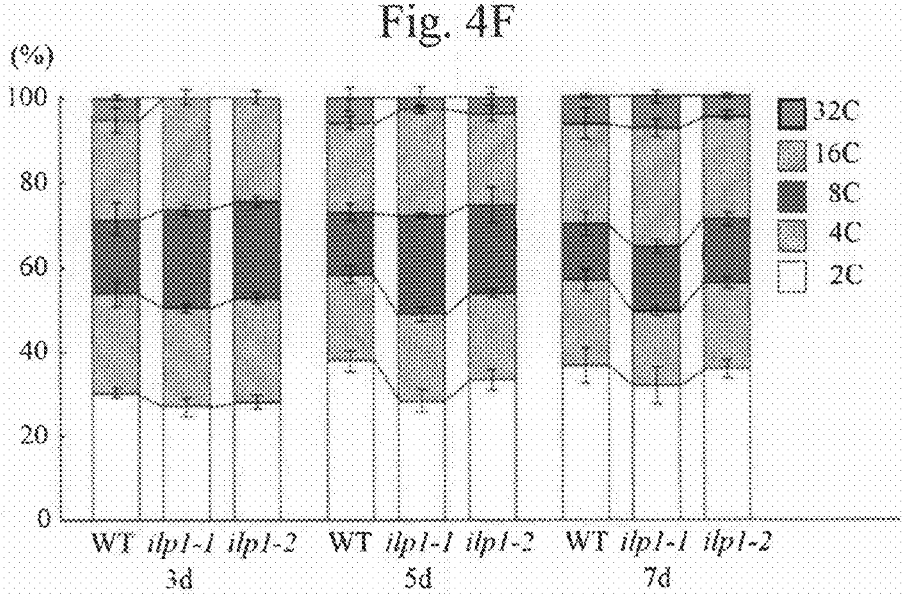

FIG. 4F shows the relative ratio of each cell ploidy for 3, 5, and 7-day-old dark-grown wild-type, ilp1-1, and ilp1-2 homozygotes. Approximately 3,000 nuclei were counted in wild-type, ilp1-1, and ilp1-2.

(Bars shown in FIGS. 4A and 4D are 5 mm. Student's t-test in FIGS. 4C and 4E: *0.001>p versus wild-type)

Figure 5A:
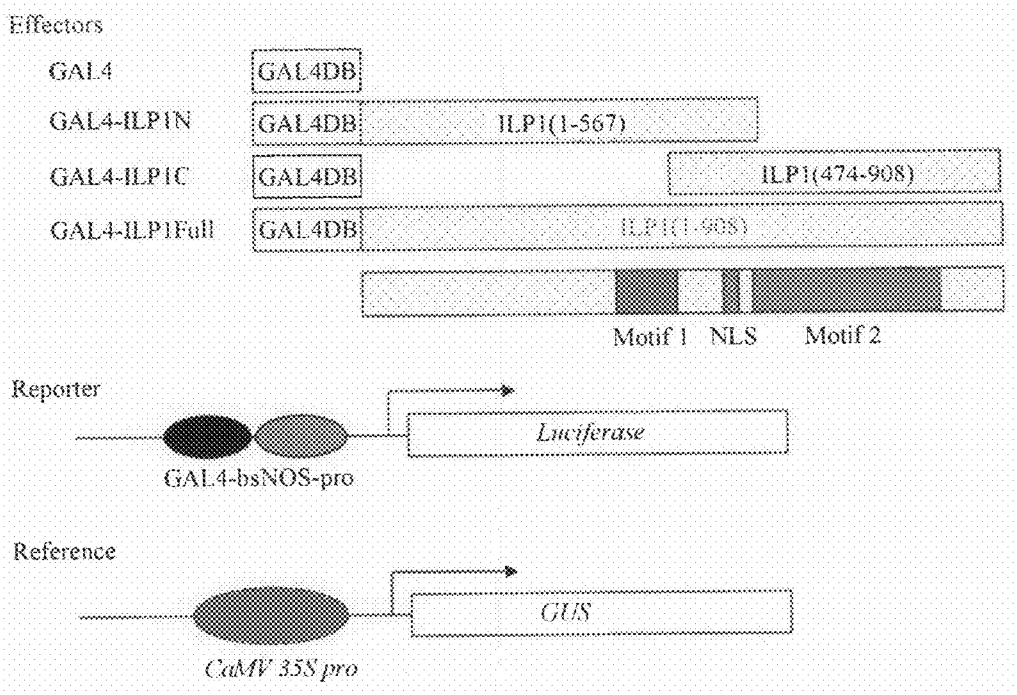

FIG. 5A shows constructs used for the in vivo transcription assay. GAL4-ILP1N: the GAL4 DNA binding domain (GAL4 DB) is fused to the N-terminal region of ILP1 (amino acid residues 1-567); GAL4-ILP1C: the GAL4 DB is fused to the C-terminal region of ILP1 (amino acid residues 474-908); and GAL4ILP1Full: GAL4 DB is fused to full-length ILP1. The reporter plasmid contains a GAL4 binding site and 0.2 kb of the nopaline synthase promoter (NOS-pro) upstream of the LUC reporter gene. The reference plasmid serves to monitor the transcription efficiency by GUS expression controlled by a constitutive CaMV 35S promoter.

Figure 5B:
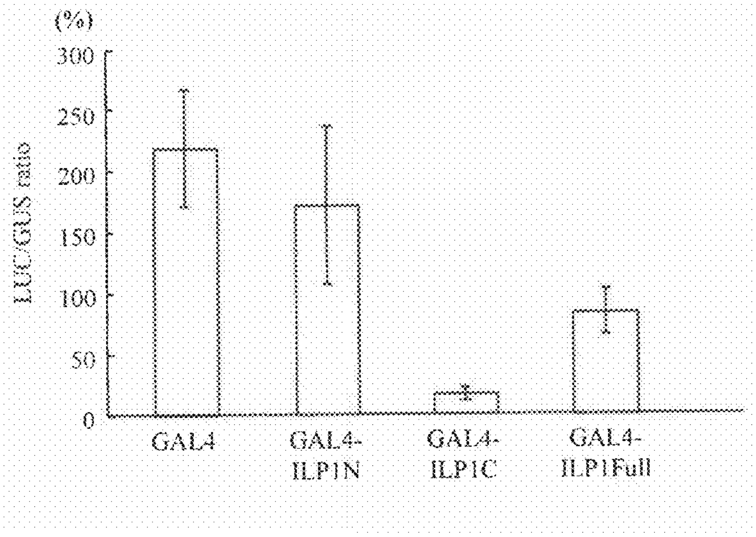

FIG. 5B shows in vivo transcription assay in tobacco leaves. LUC/GUS ratio: LUC expression (reporter) was normalized with GUS expression (reference). Error bars indicate standard deviations. The experiment was replicated 5 times.

Figure 6A:
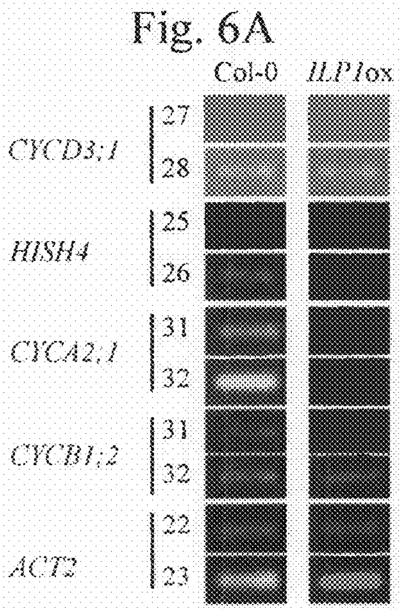

FIG. 6A shows semi-quantitative RT-PCR analysis of cell-cycle-related genes. CYCD3;1, HISH4, CYCA2;1, and CYCB1;2 are G1-, S-, G2- and M-phase-specific markers, respectively. ACT2 was used as a control. The numbers on the left indicate the numbers of PCR cycles.

Figure 6B:
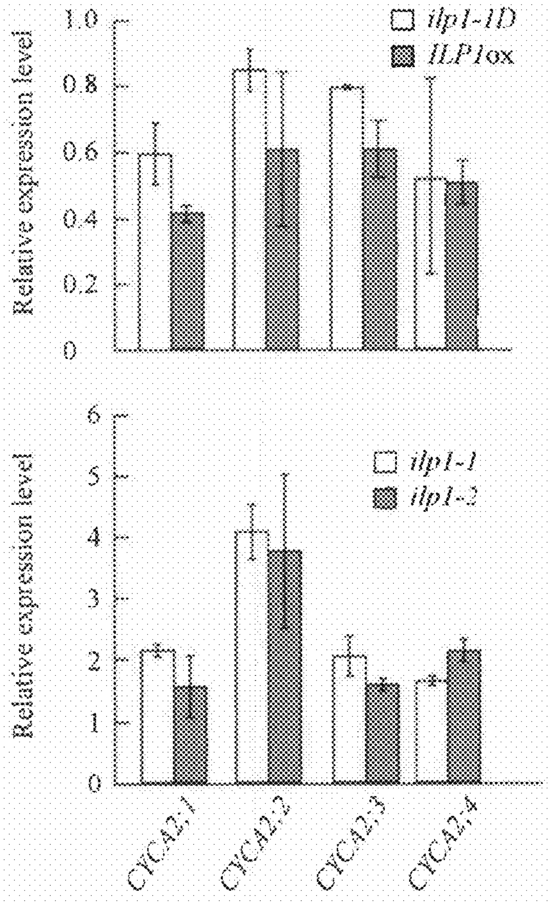

FIG. 6B shows real-time PCR analysis of CYCA2 gene family members. The expression levels of the CYCA2 family genes were normalized with ACT2 expression. Relative expression levels: expression levels of the CYCA2 genes in each mutant line and an ILP1-ox line relative to the wild type. RNA was isolated from 7-day-old dark-grown hypocotyls of ilp1-1D and ILP1ox (the upper panel), and from 3-day-old dark-grown hypocotyls of ilp1-1 and ilp1-2 (the lower panel). Error bars indicate standard deviations. The experiment was replicated four times.

Figure 6C:
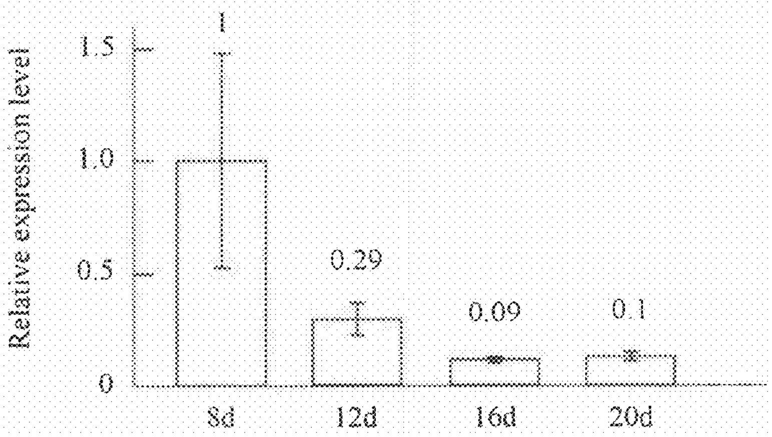

FIG. 6C shows real-time PCR analysis of ILP1 in wild-type seedlings (Col-0). Error bars indicate standard deviations. The numbers indicate the ILP1 expression levels relative to day 8. The experiment was replicated four times.

Figure 6D:
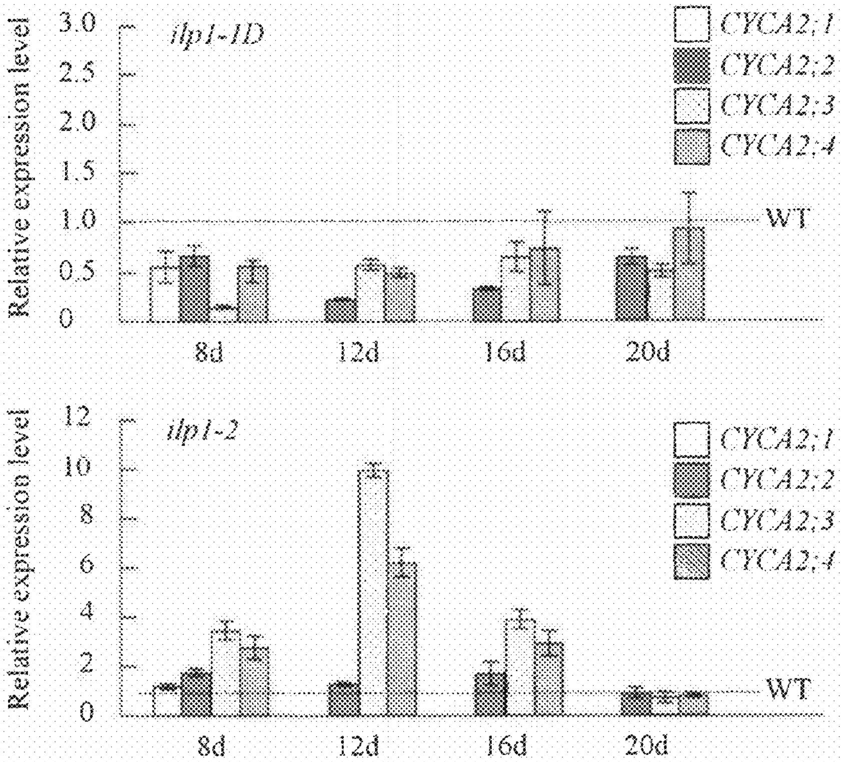

FIG. 6D shows real-time PCR analysis of the CYCA2 gene family in first leaves of ilp1-1D and ilp1-2 at 4 developmental stages. Expression levels of the CYCA2 gene family were normalized with ACT2 expression levels. Relative expression levels: expression levels of the CYCA2 genes in each mutant line relative to the wild type. CYCA2;1 expression was not detected in wild-type and ilp1-1D after day 12.

Figure 6E:
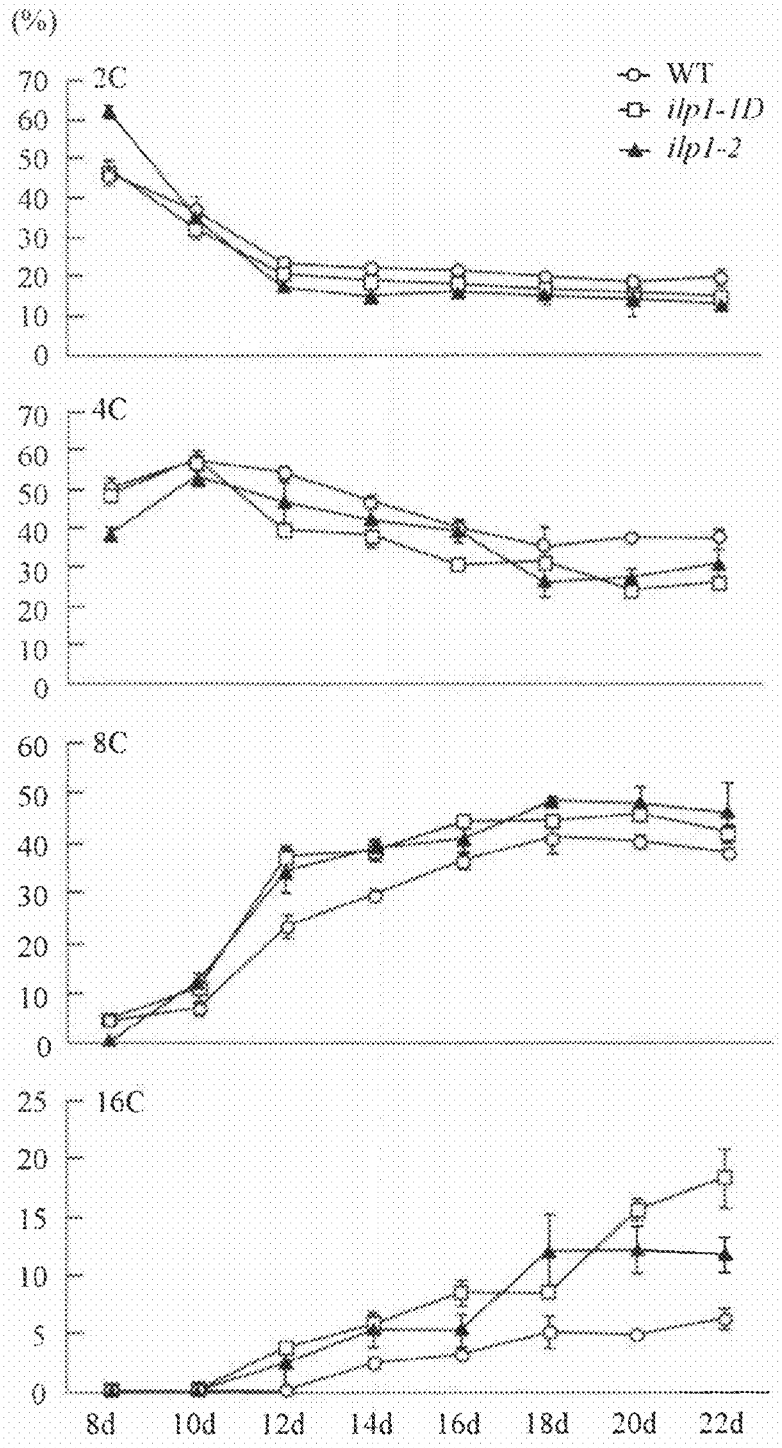

FIG. 6E shows ploidy distribution patterns of first leaves of wild-type, ilp1-1D, and ilp1-2 at different developmental stages. The fraction of each ploidy was plotted as wild-type (open circle), ilp1-1D (open square), and ilp1-2 (closed triangle). Isogenic wild-type siblings of ilp1-1D were used as wild-type seedlings. The same result was obtained from wild-type siblings of ilp1-2.

Figure 7A:
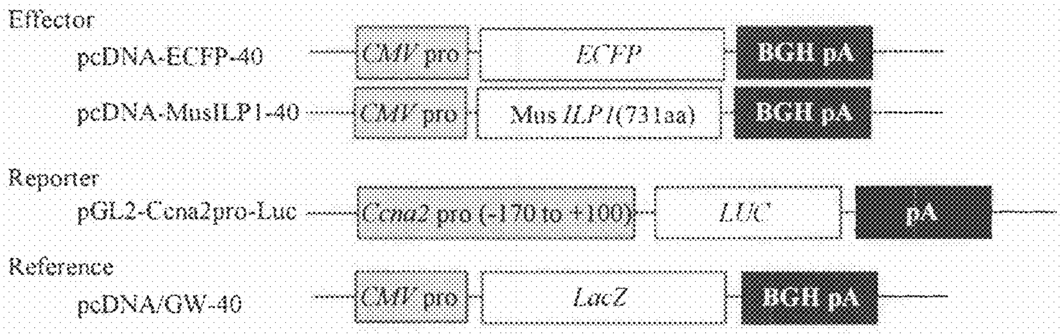

FIG. 7A shows a construct used for the in vivo transcription assay in mouse NIH3T3 cells. pcDNA-ECFP-40 contains the enhanced cyan fluorescent protein (ECFP) gene, which is used as a control, and pcDNA-MusILP1-40 contains the mouse ILP1 cDNA (731 aa, AAK68725). The reporter plasmid consists of the Ccna2 promoter region (−170 to +100 by of the transcription initiation site) fused to the LUC gene. The reference plasmid serves to monitor the transcription efficiency by β-galactosidase (LacZ) expression (CMV pro: CMV promoter; BGH pA: bovine growth hormone polyadenylation site)

Figure 7B:
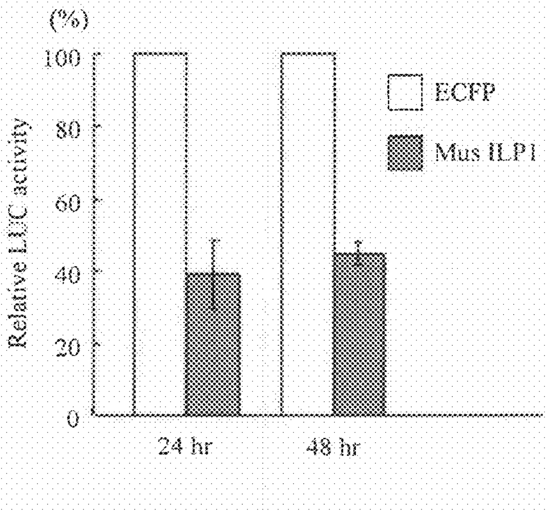

FIG. 7B shows in vivo transcription assay in mouse NIH3T3 cells. LUC activity was normalized with β-galactosidase activity (relative LUC activity: LUC activity of mouse ILP1 relative to ECFP). Activity was measured 24 hours and 48 hours after transfection. Error bars indicate standard deviations. The experiment was replicated four times.

Figure 8A:
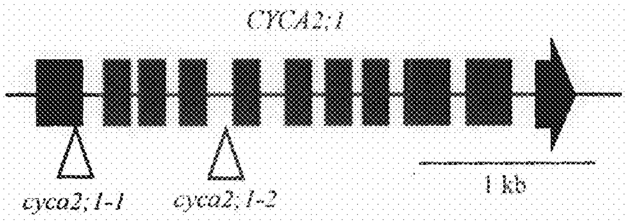

FIG. 8A shows loci of T-DNA insertions in CYCA2;1. Triangles indicate insertion sites of T-DNAs of cyca2;1-1 (SALK_121077) and cyca2;1-2 (SALK_136750).

Figure 8B:
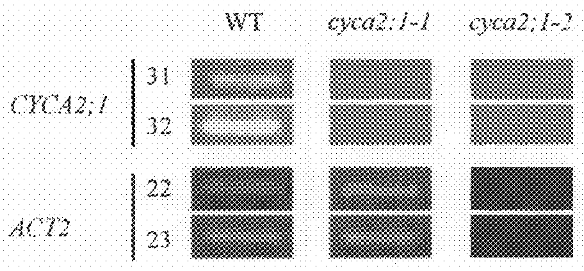

FIG. 8B shows semi-quantitative RT-PCR of CYCA2;1. The numbers on the left indicate the numbers of PCR cycles.

Figure 8C:
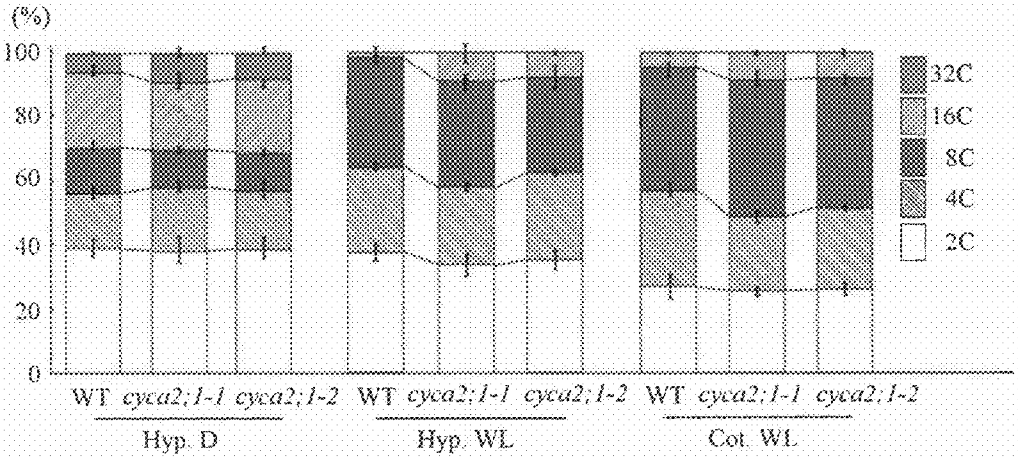

FIG. 8C shows the relative ratio of each cell ploidy for dark- and light-grown wild-type, cyca2;1-1, and cyca2;1-2 homozygotes. (Hyp. D): hypocotyl cells of dark-grown seedlings; (Hyp. WL): hypocotyl cells of light-grown seedlings; and (Cot. WL): cotyledonal cells of dark-grown seedlings. Isogenic wild-type siblings of cyca2;1-1 were used as wild-type seedlings. The same result was obtained from wild-type siblings of cyca2;1-2. Approximately 3,000 nuclei were counted in the wild-type, cyca2;1-1, and cyca2;1-2. Error bars indicate standard deviations.

Figure 9:
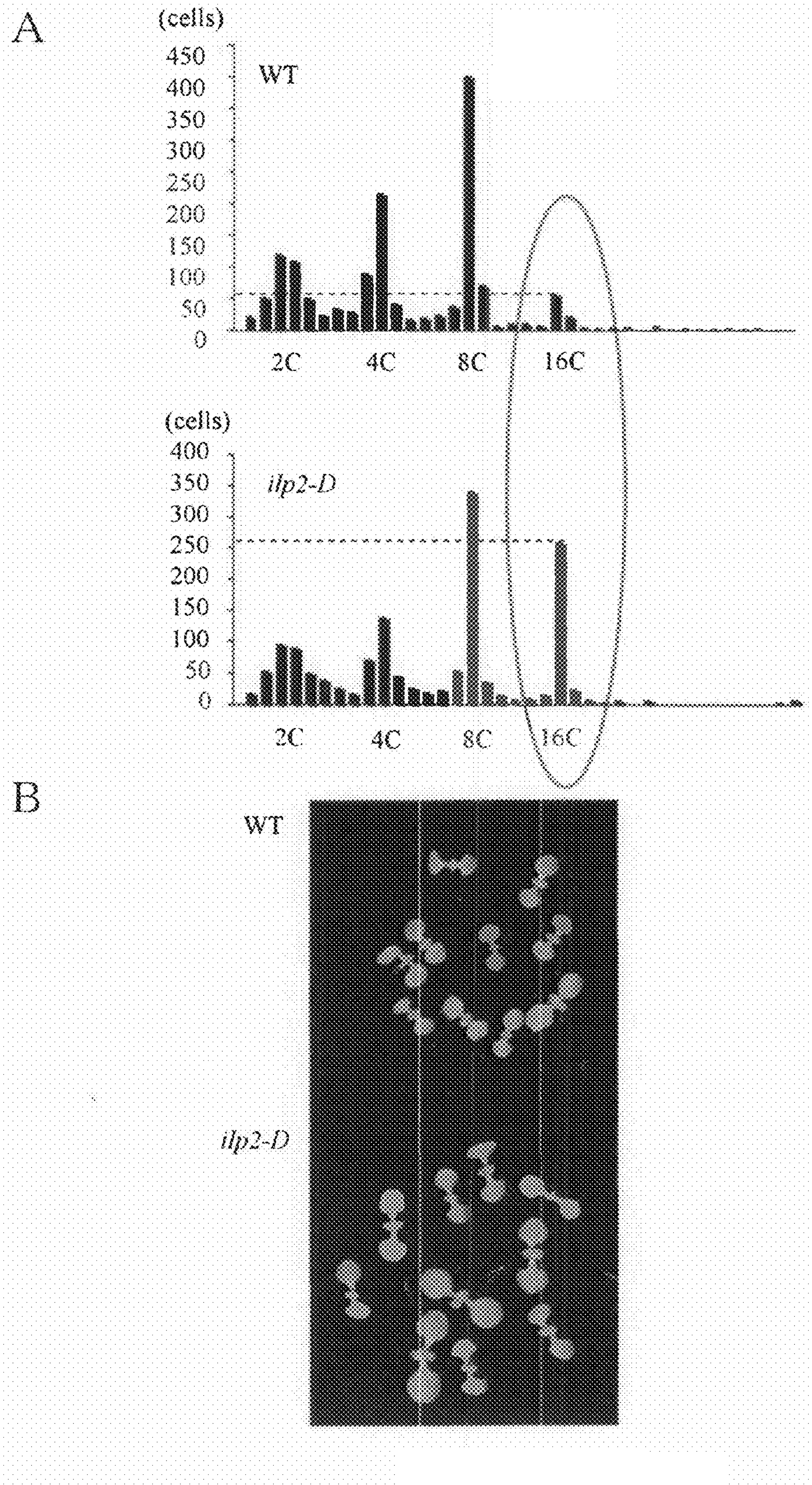
Figure 9:
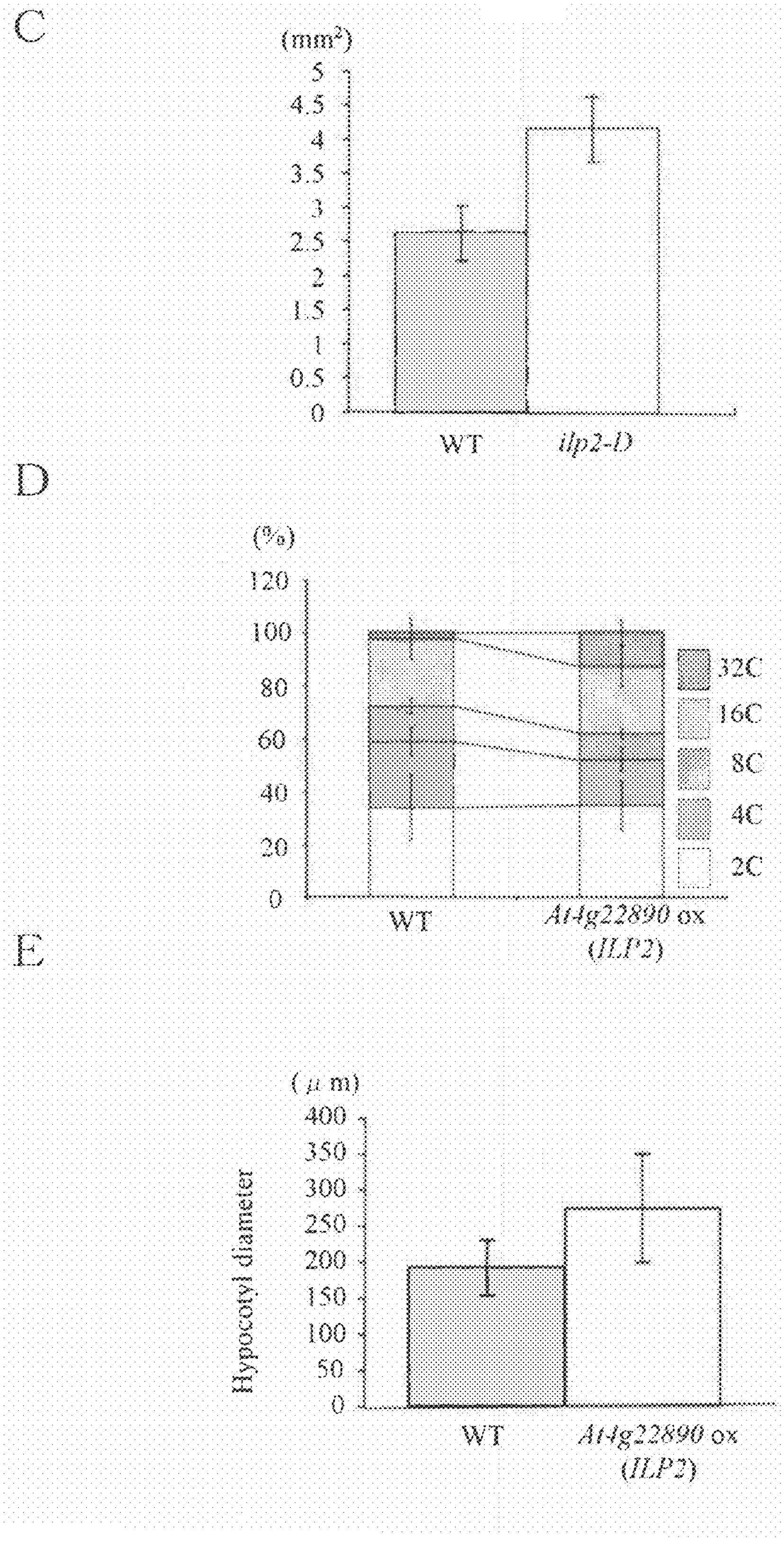
Figure 9:
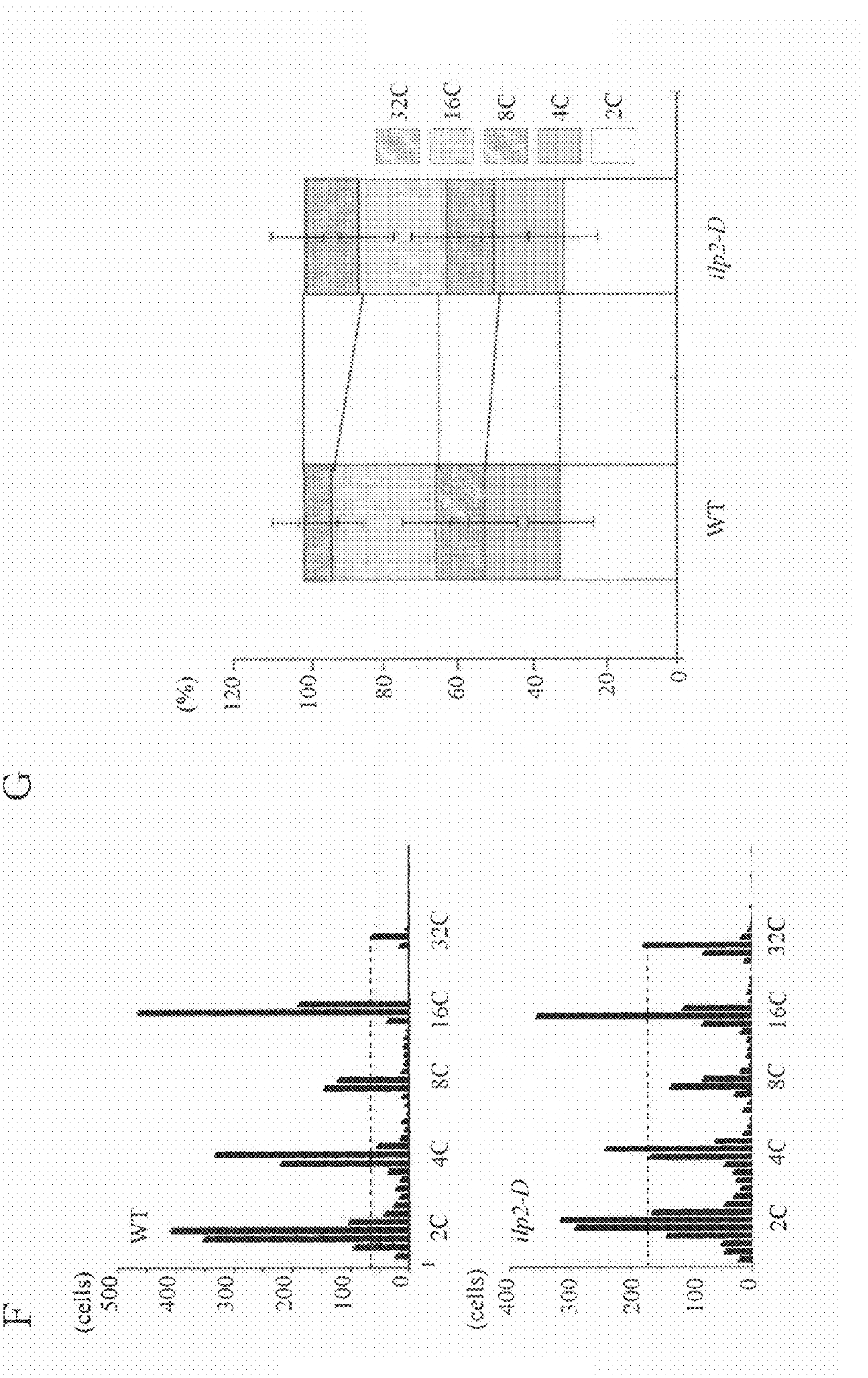
Figure 9:
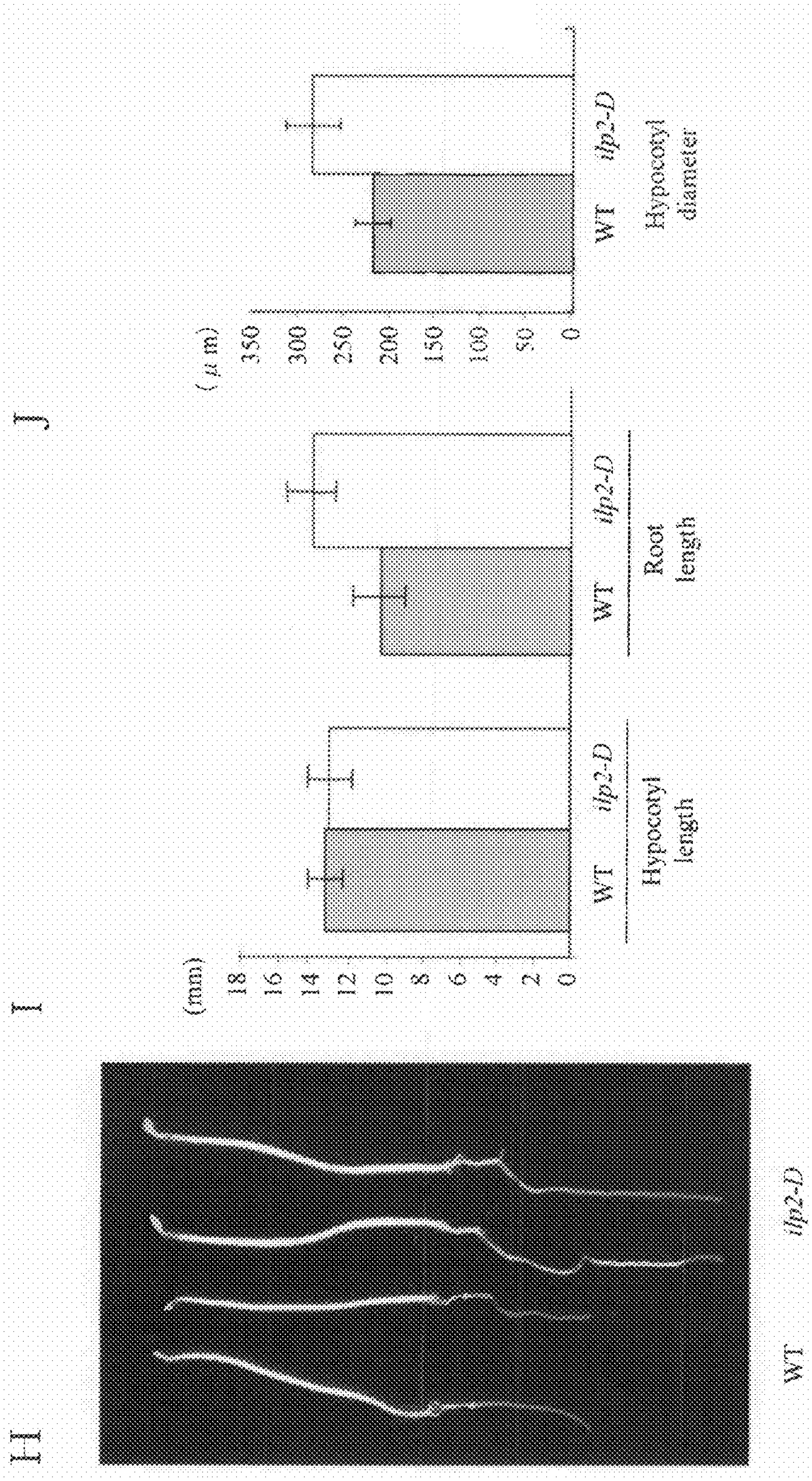

FIG. 9 shows phenotypes of ilp2-D.

FIG. 9A shows DNA content in cotyledon of light-grown ilp2-D. The upper part indicates a wild type and the lower part indicate ilp2-D.

FIG. 9B shows morphology of cotyledon of light-grown ilp2-D. The upper part indicates a wild type and the lower part indicate ilp2-D. ilp2-D has larger cotyledon than a wild type.

FIG. 9C shows a cotyledonal area of light-grown ilp2-D. Error bars indicate standard deviations.

FIG. 9D shows DNA content in hypocotyls of dark-grown ILP2-overexpressing seedlings (ILP2ox). Error bars indicate standard deviations.

FIG. 9E shows diameters of hypocotyls of dark-grown ILP2-overexpressing seedlings (ILP2ox). Error bars indicate standard deviations.

FIG. 9F shows DNA content in hypocotyls of dark-grown ilp2-D. The upper part indicates a wild type and the lower part indicate ilp2-D.

FIG. 9G shows DNA content in hypocotyls of dark-grown ilp2-D. Error bars indicate standard deviations.

FIG. 9H shows morphology of 7-day-old dark-grown wild-type and ilp2-D seedlings.

FIG. 9I shows hypocotyl length and a root length of dark-grown ilp2-D. Error bars indicate standard deviations. The roots of ilp2-D are elongated compared with those of a wild type.

FIG. 9J shows diameters of hypocotyls of dark-grown ilp2-D. Error bars indicate standard deviations. ilp2-D has a thicker hypocotyl than a wild type.

Figure 10:
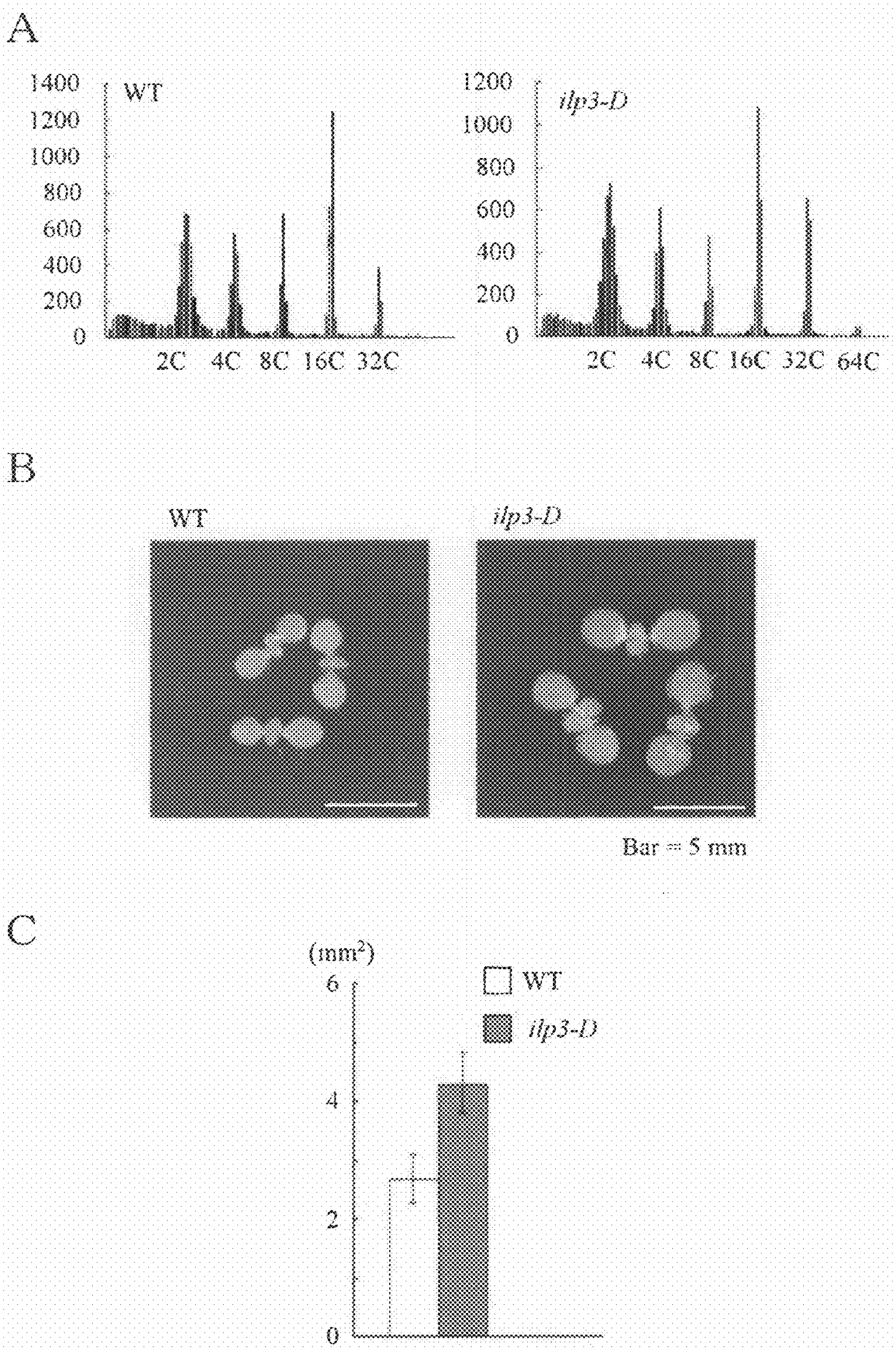
Figure 10:
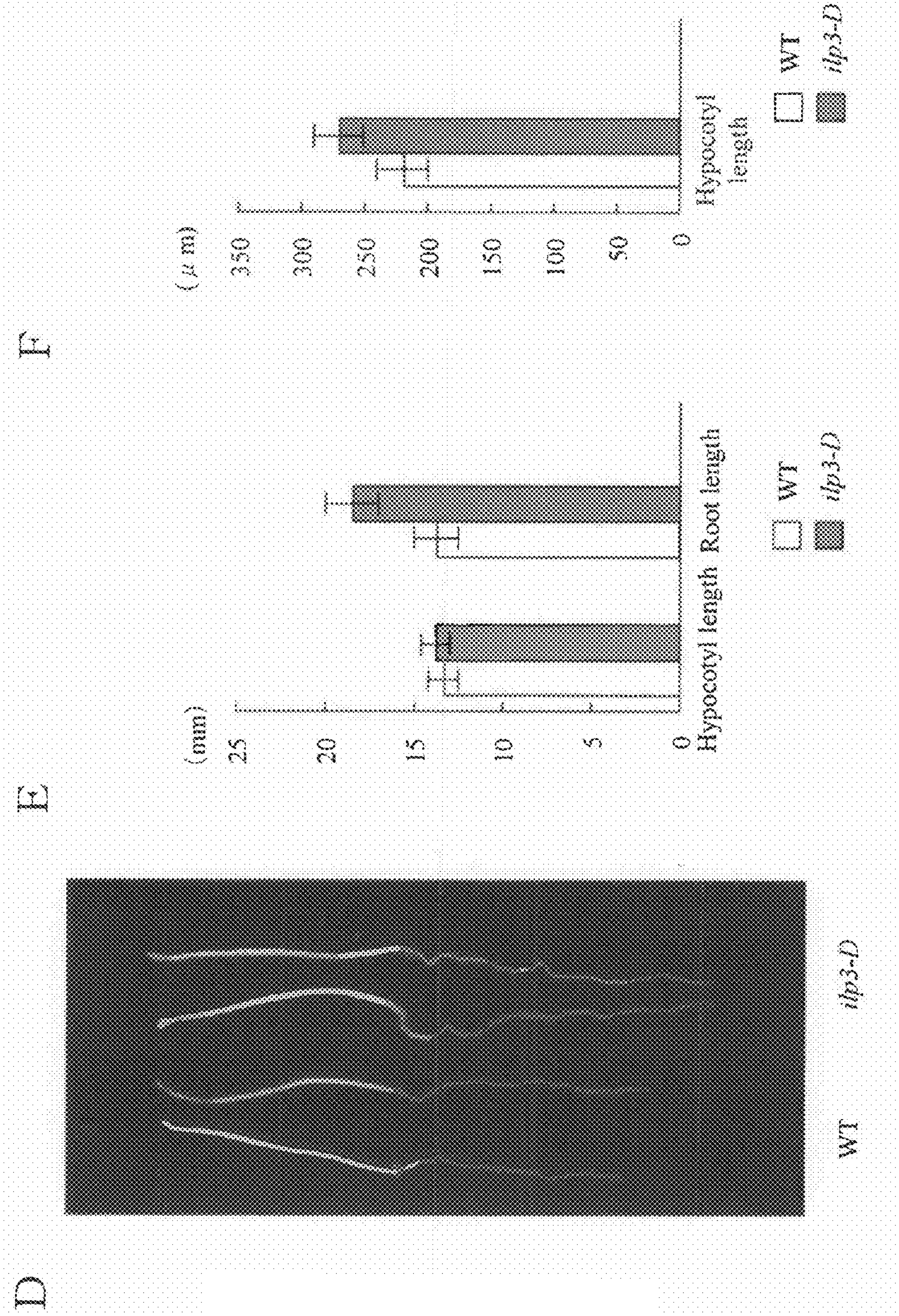

FIG. 10 shows phenotypes of ilp3-D.

FIG. 10A shows DNA content in hypocotyls of dark-grown ilp3-D. The left part indicates a wild type and the right part indicate ilp3-D.

FIG. 10B shows morphology of a cotyledon of light-grown ilp3-D. The left part indicates a wild type and the right part indicate ilp3-D. ilp3-D has a larger cotyledon than a wild type.

FIG. 10C shows a cotyledonal area of light-grown ilp3-D. Error bars indicate standard deviations.

FIG. 10D shows morphology of 7-day-old dark-grown wild-type and ilp3-D seedlings.

FIG. 10E shows a hypocotyl length and a root length of dark-grown ilp3-D. Error bars indicate standard deviations. The roots of ilp3-D are elongated compared with those of a wild type.

FIG. 10F shows the diameter of hypocotyl of dark-grown ilp3-D. Error bars indicate standard deviations. Ilp3-D has a thicker hypocotyl than a wild type.

Figure 11:
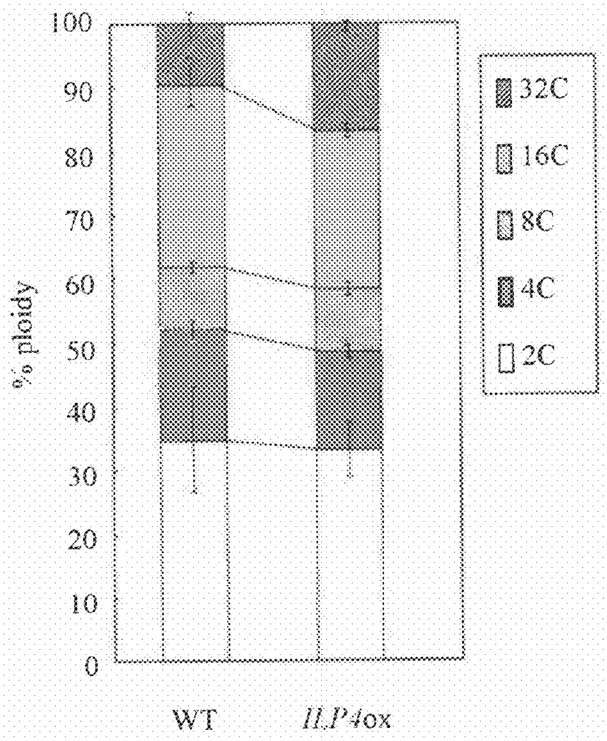
Figure 11:
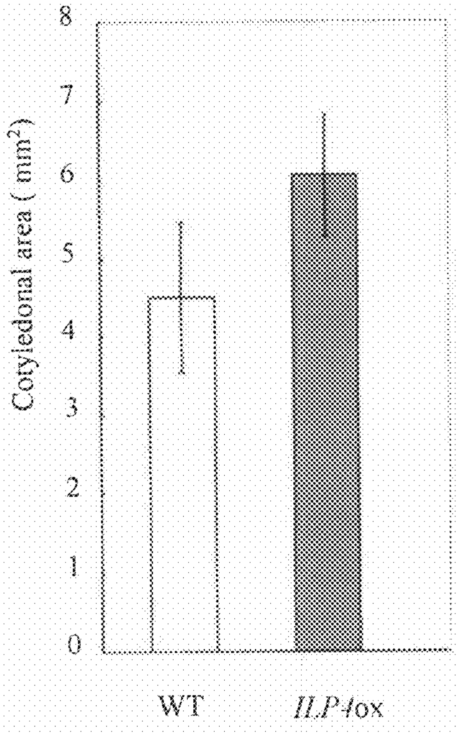

FIG. 11 shows phenotypes of ILP4-overexpressing seedlings (ILP4ox).

FIG. 11A shows DNA content in hypocotyls of dark-grown ILP4-overexpressing seedlings (ILP4ox). Error bars indicate standard deviations.

FIG. 11B shows a cotyledonal area of light-grown ILP4-overexpressing seedlings (ILP4ox). Error bars indicate standard deviations.

Figure 12:
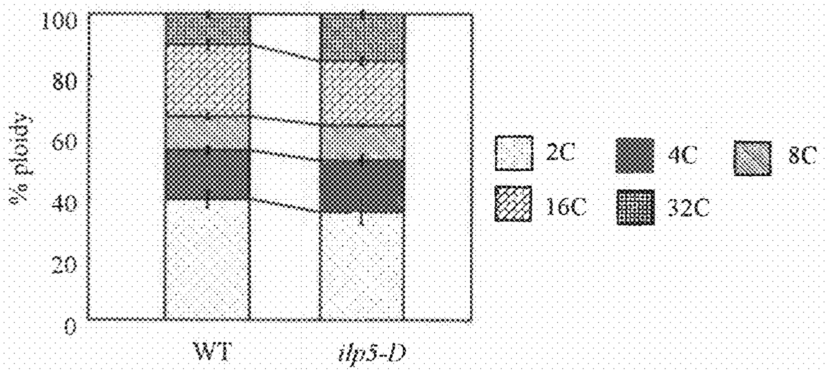
Figure 12:
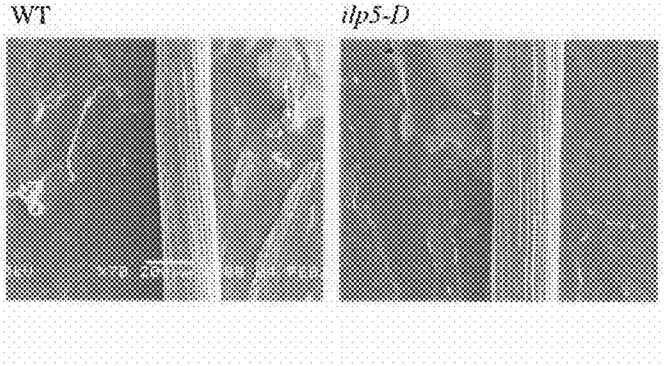
Figure 12:
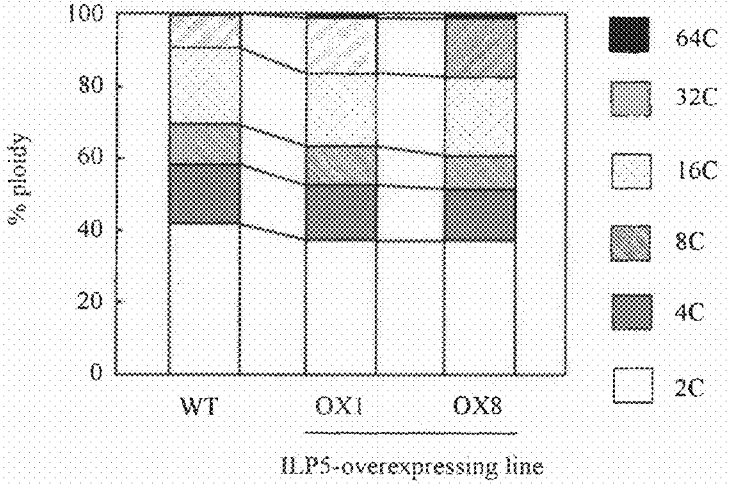
Figure 12:
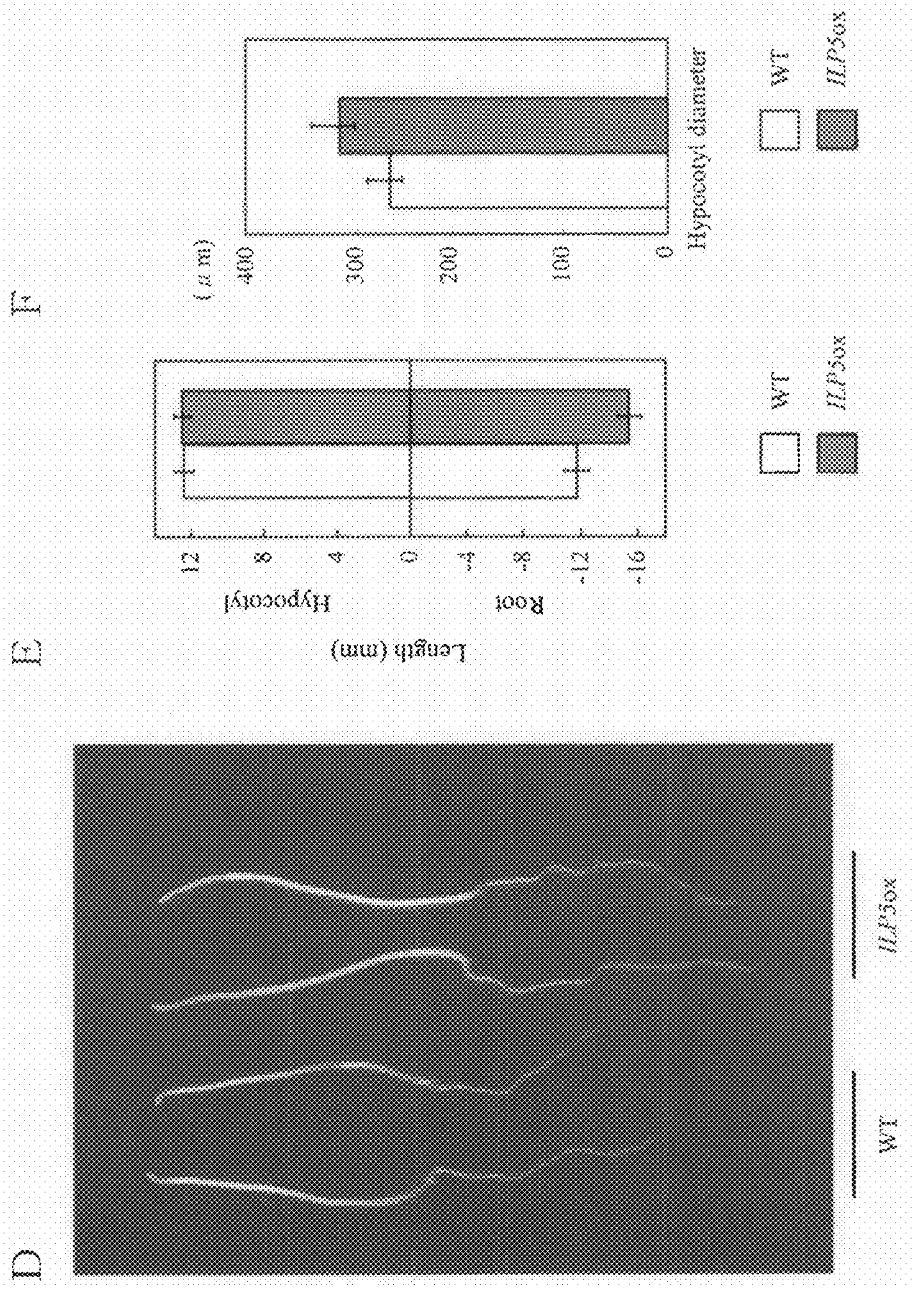
Figure 12:
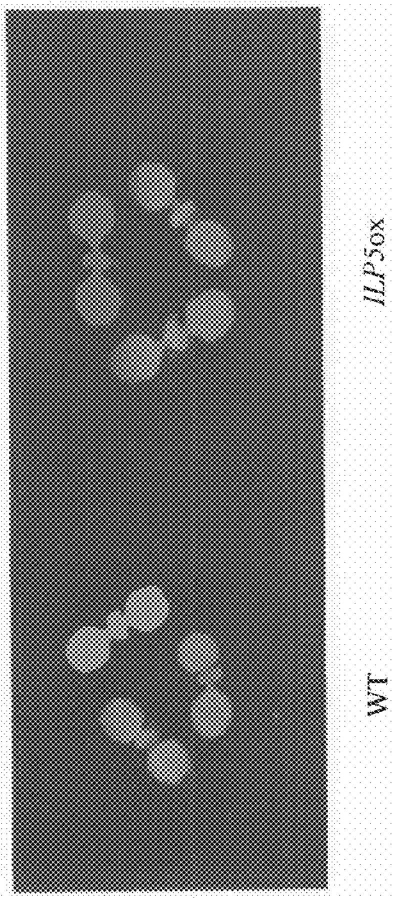
Figure 12:
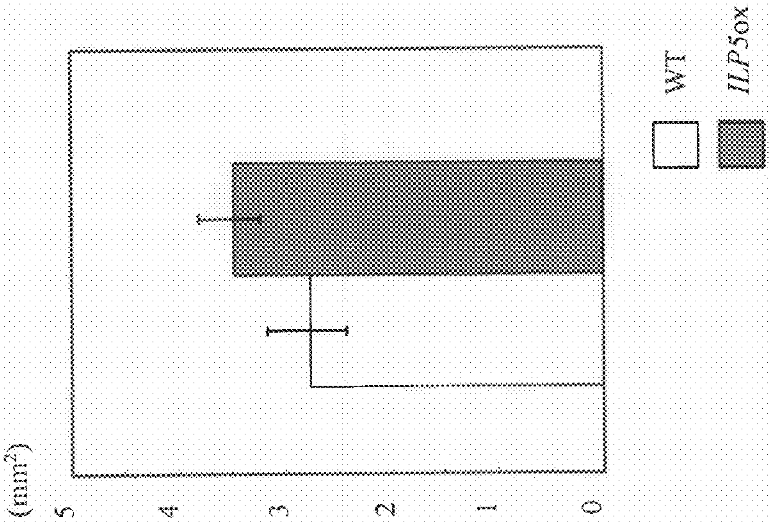

FIG. 12 shows phenotypes of ilp5-D.

FIG. 12A shows DNA content in hypocotyls of dark-grown ilp5-D. Error bars indicate standard deviations.

FIG. 12B shows a hypocotyl surface of dark-grown ilp5-D (an electron microscope image). The left part indicates a wild type and the right part indicates ilp5-D. Ilp5-D has thicker hypocotyl than a wild type.

FIG. 12C shows DNA content in hypocotyls of dark-grown ILP5-overexpressing seedlings (ILP5ox).

FIG. 12D shows morphology of 7-day-old dark-grown wild-type and ILP5-overexpressing seedlings (ILP5ox).

FIG. 12E shows a hypocotyl length and a root length of dark-grown ILP5-overexpressing seedlings (ILP5ox). Error bars indicate standard deviations. The roots of ILP5ox are elongated compared with those of a wild type.

FIG. 12F shows a diameter of hypocotyl of dark-grown ILP5-overexpressing seedlings (ILP5ox). Error bars indicate standard deviations. ILP5ox has a thicker hypocotyl than a wile type.

FIG. 12G shows morphology of cotyledons of light-grown ILP5-overexpressing seedlings (ILP5ox). The left part indicates a wild type and the right part indicates ILP5ox. ILP5ox has a larger cotyledon than a wild type.

FIG. 12H shows a cotyledonal area of light-grown ILP5-overexpressing seedlings (ILP5ox). Error bars indicate standard deviations.

Figure 13:
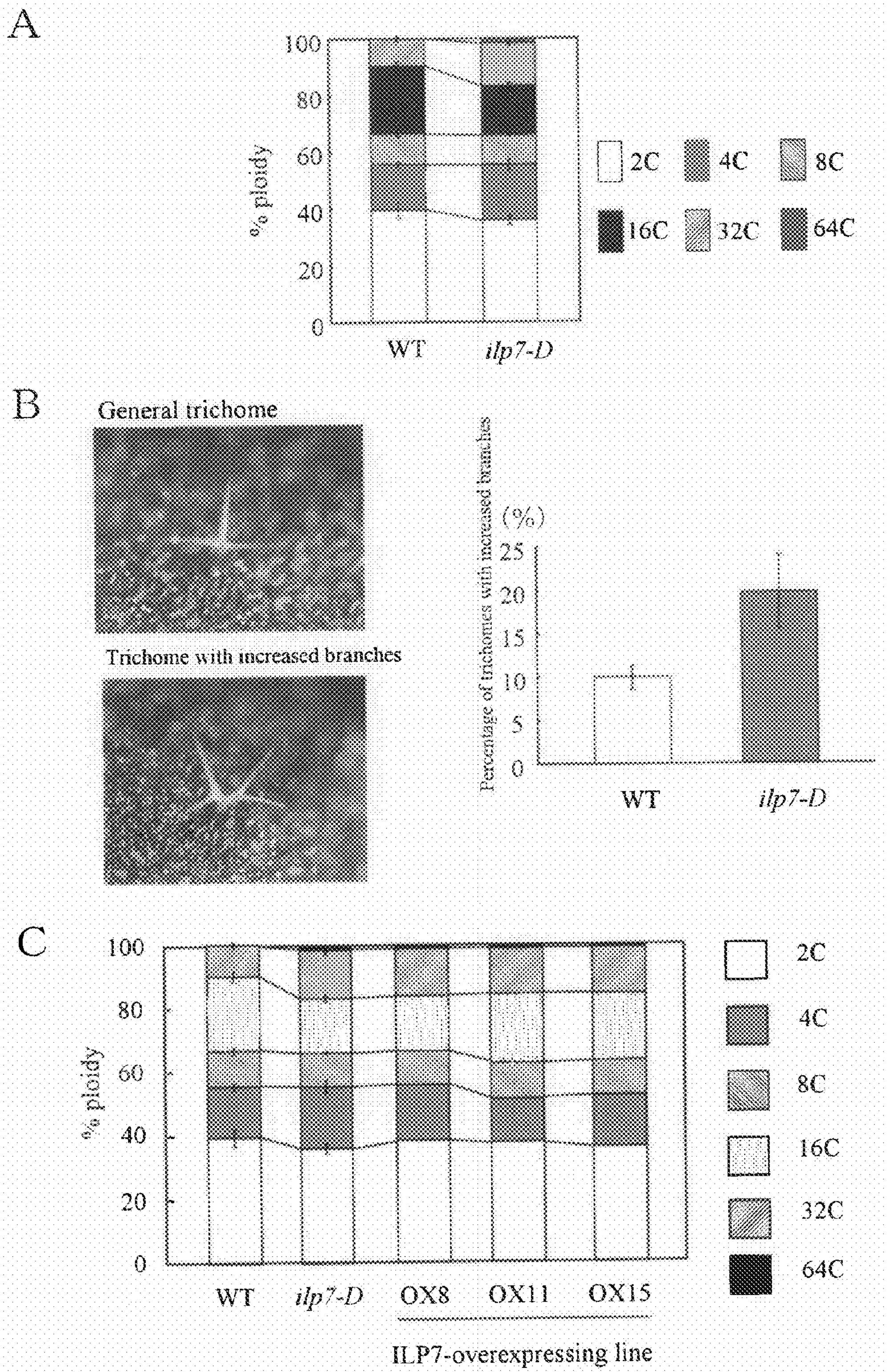
Figure 13:
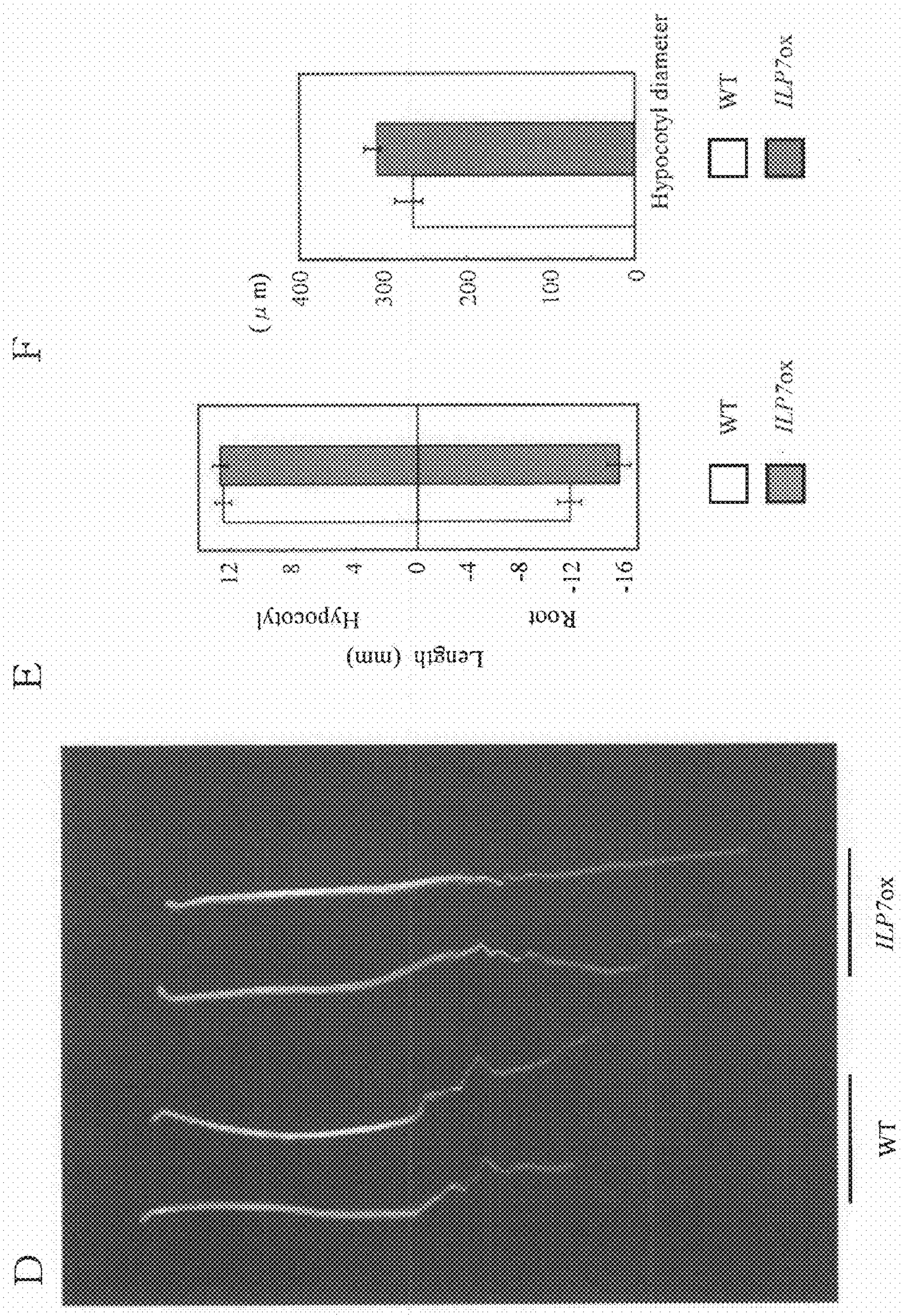
Figure 13:
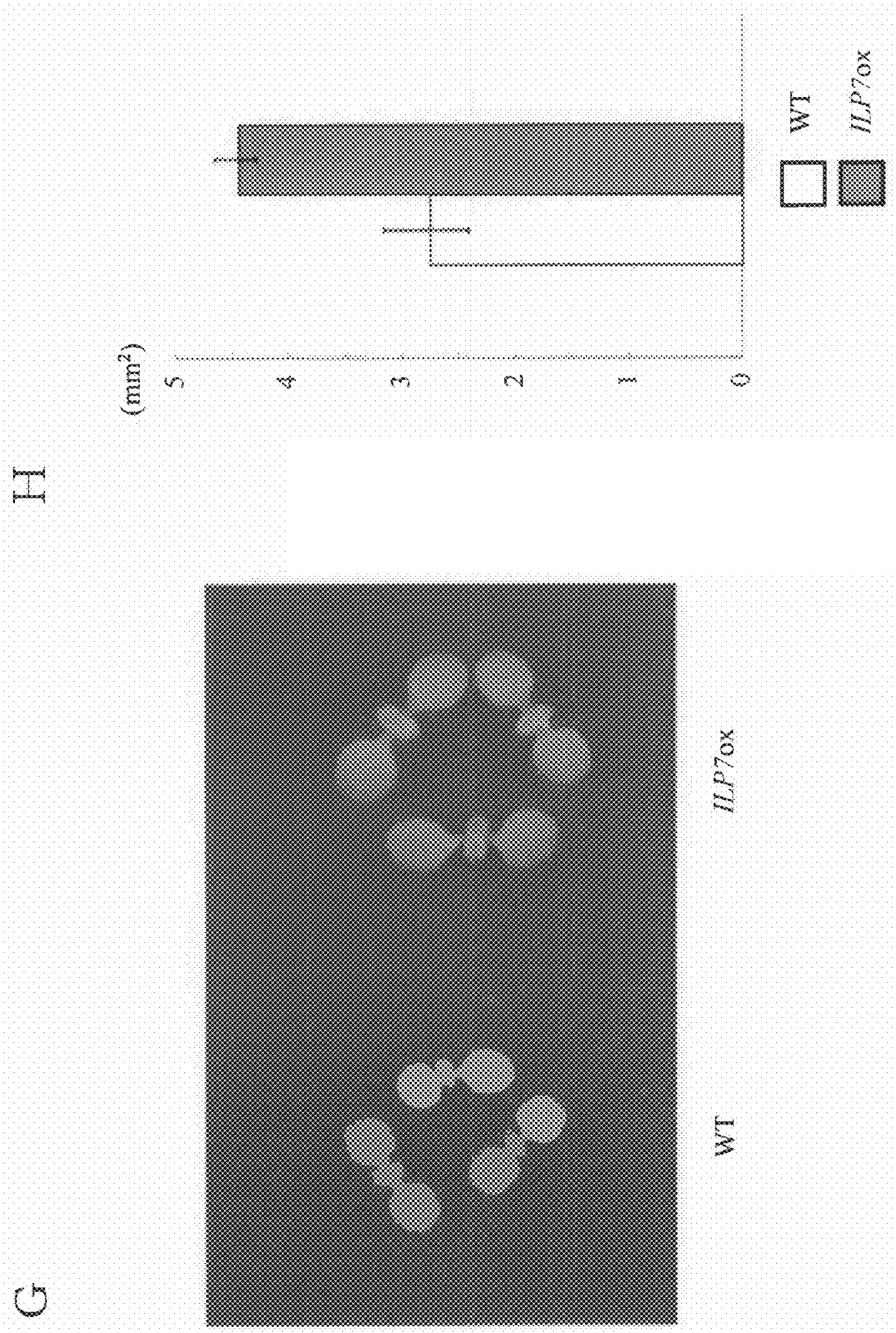

FIG. 13 shows phenotypes of ilp7-D.

FIG. 13A shows DNA content in hypocotyls of dark-grown ilp7-D. Error bars indicate standard deviations.

FIG. 13B shows trichome distribution in the foliage leaves of ilp7-D. In the photograph, the upper part indicates general trichomes, and the lower part indicates an enlarged trichome resulting from increase of a branch. The number of ilp7-D with an increased number of branches (i.e., enlarged trichome) is increased, compared with the wild-type case. Error bars indicate standard deviations.

FIG. 13C shows DNA content in hypocotyls of dark-grown ILP7-overexpressing seedlings (ILP7ox). Error bars indicate standard deviations.

FIG. 13D shows morphology of 7-day-old dark-grown wild-type and ILP7-overexpressing seedlings (ILP7ox).

FIG. 13E shows hypocotyl lengths and root lengths of dark-grown ILP7-overexpressing seedlings (ILP7ox). Error bars indicate standard deviations. The roots of ILP7ox are elongated compared with those of a wild type.

FIG. 13F shows the diameters of hypocotyls of dark-grown ILP7-overexpressing seedlings (ILP7ox). Error bars indicate standard deviations. ILP7ox has a thicker hypocotyl than a wild type.

FIG. 13G shows morphology of cotyledon of light-grown ILP7-overexpressing seedlings (ILP7ox). The left part indicates a wild type and the right part indicates ILP7ox. ILP7ox has a larger cotyledon than a wild type.

FIG. 13H shows a cotyledonal area of light-grown ILP7-overexpressing seedlings (ILP7ox). Error bars indicate standard deviations.

This patent application claims priority from Japanese Patent Application No. 2007-085500 filed on Mar. 28, 2007, and includes part or all of the contents as disclosed in the description thereof.

Hereafter, the present invention is described in detail.

1. Gene having Endoreduplication Promoting Activity

The gene of the present invention can be obtained by preparing a mutant of a plant gene with activated transcription via activation tagging and cloning the causative gene.

Specifically, the gene of interest can be obtained in the following manner.

(i) An activation T-DNA tagging vector is randomly inserted into the genome of *Arabidopsis thaliana* via *Agrobacterium* to prepare an activation tagging line.

(ii) A $T_2$ plant is allowed to grow from the seed collected from the tagging line, phenotypic characters are recorded based on the test items regarding predetermined phenotypic characters (e.g., nuclear DNA content, thickness and length of hypocotyl, size of cotyledon, and the number of branches and size of trichome), and a digital image thereof is also recorded.

(iii) A DNA fragment containing T-DNA is recovered via plasmid rescue from the genome of a mutant of $T_2$ generation having phenotypic characters apparently different from those of a wild-type plant, and the sequence thereof is determined.

(iv) The DNA fragment is introduced into a wild-type *Arabidopsis thaliana* plant to inspect whether or not phenotypic characters of the mutant can be reproduced.

(v) Corresponding cDNA is cloned.

The term "$T_1$ generation" used herein refers to a plant generation that is obtained from the seed of a transgenic plant of $T_0$ generation. The "$T_1$ generation" is the first aggregate of transgenic plants and it can be selected with the use of a selection agent corresponding to a tolerant gene of the transgenic plant (e.g., antibiotics or herbicide). The term "$T_2$ generation" refers to a plant generation that is obtained via self-pollination of flower of the plant of the $T_1$ generation, which has been selected in advance as a transgenic plant.

As an activation T-DNA tagging vector, a pPCVICEn4HPT vector that has been developed by Walden and others (Hayashi, H. et al, Science, 258, 1350-1353, 1992) can be used. This vector is a binary vector comprising 4 tandem enhancers (−90 to −440) in the CaMV 35S promoter adjacent to RB. *Arabidopsis thaliana* is transformed in *Agrobacterium* GV3101 (pMP90RK) comprising pPCVICEn4HPT. Transformation can be carried out by the floral dip method comprising soaking the terrestrial part of *Arabidopsis thaliana* in the *Agrobacterium* suspension and performing coculture.

If an interesting mutant is obtained, a gene that would cause mutation via transcription activation is cloned. Cloning is preferably carried out via plasmid rescue. Tail-PCR, adaptor PCR, and other techniques can also be employed. Specifically, plasmid rescue is carried out by purifying DNA of the mutant, treating the DNA with various restriction enzymes, confirming the band size via Southern blotting, and searching for restriction enzymes that would produce a fragment of approximately 10 to 20 kb, including the inserted T-DNA. Subsequently, DNA is then treated with the restriction enzymes, treated with phenol and chloroform, and subjected to ethanol precipitation, followed by self-ligation with the aid of ligase. The resultant is introduced into a competent cell (i.e., *E. coli* DH10B) via electroporation, a tolerant strain is selected in an ampicillin-containing medium, and the plasmid is selected via a conventional technique. The border sequence with T-DNA in the genomic DNA portion contained in the resulting plasmid is determined, and the position of the genome into which T-DNA has been inserted is then determined. Based on such position, a gene having a translation initiation site within 6 kb from the enhancer sequence is searched for from the *Arabidopsis thaliana* genome database (http://www.mips.biochem.mpg.de). These genes are used as candidate genes to design primers specific to the gene or recombinant vector that had been introduced into the plant, and cDNA is amplified from the *Arabidopsis thaliana* cDNA library, followed by cloning. The cDNA fragments are introduced into plants via *Agrobacterium* to inspect whether or not phenotypes of mutants can be reproduced.

The nucleotide sequence of the cDNA can be determined via conventional techniques such as the chemical modification technique of Maxam-Gilbert or the dideoxynucleotide chain termination method utilizing an M13 phage. In general, sequencing is carried out using an automated nucleotide sequencer (e.g., the ABI373 Sequencer and the 310 DNA Sequencer, Applied Biosystems). The determined nucleotide sequence is analyzed using DNA analyzing software such as DNASIS (Hitachi Software Engineering Co., Ltd), and a protein-encoding region that is encoded in the obtained DNA strand can be found.

By the above technique, AT5g08550 (Z010521) (note that descriptions in parentheses are designations of tagging lines) was isolated and identified as a gene having endoreduplication promoting activity, and the identified strain was designated as ilp1-1D. The nucleotide sequence of ILP1 is shown in SEQ ID NO: 1 and the amino acid sequence encoded by ILP1 is shown in SEQ ID NO: 2. By the above technique, AT4g22890 (Z009804), AT5g14960 (Z036220), AT5g56790 (Z032529), AT4g15140 (Z05228), and AT5g57410 (Z058029) were also isolated and identified as genes having endoreduplication promoting activity and these genes were designated as ILP2, ILP3, ILP4, ILP5, and ILP7. The nucleotide sequences of ILP2, ILP3, ILP4, ILP5, and ILP7 are shown in SEQ ID NOs: 3, 5, 7, 9, and 11 and the amino acid sequences encoded thereby are shown in SEQ ID NOs: 4, 6, 8, 10, and 12. Hereafter, such genes having endoreduplication promoting activity are collectively referred to as ILP genes.

An ILP gene used in the present invention may be a gene encoding a protein consisting of an amino acid sequence derived from the amino acid sequence as shown in SEQ ID NO: 2, 4, 6, 8, 10, or 12 by deletion, substitution, or addition of one or several amino acids, provided that such gene has endoreduplication promoting activity.

The number of the amino acid residues that may be deleted, substituted, or added refers to the number that can be deleted, substituted, or added by a conventional method of preparing a mutant protein, such as site-directed mutagenesis. Such number is preferably 1 to several. For example, 1 to 10, and preferably 1 to 5, amino acid residues may be deleted from the amino acid sequence as shown in any of SEQ ID NO: 2, 4, 6, 8, 10, or 12; 1 to 10, and preferably 1 to 5, amino acid residues may be added to the amino acid sequence as shown in any of SEQ ID NO: 2, 4, 6, 8, 10, or 12; or 1 to 10, and preferably 1 to 5, amino acid residues may be substituted with other amino acid residues in the amino acid sequence as shown in any of SEQ ID NO: 2, 4, 6, 8, 10, or 12. The term "mutation" used herein primarily refers to mutation that is artificially introduced via a conventional method for preparing a mutant protein. It may be similar to a mutation that exists in nature.

The gene of the present invention also includes a gene encoding a protein consisting of an amino acid sequence having 80% or higher homology to the amino acid sequence as shown in SEQ ID NO: 2, 4, 6, 8, 10, or 12 and having endoreduplication promoting activity. The aforementioned 80% or higher homology preferably refers to homology of 85% or higher, more preferably to homology of 90% or higher, and most preferably to homology of 95% or higher. Sequence identity can be determined via a FASTA or BLAST search.

The term "endoreduplication" used herein refers to a special cell cycle that undergoes DNA duplication without causing cell division. The term "endoreduplication promoting activity" refers to activity of accelerating such cell cycle and increasing the nuclear DNA content in plant cells.

When an amino acid "has endoreduplication promoting activity," such activity is substantially equivalent to activity of the protein having the amino acid sequence as shown in SEQ ID NO: 2, 4, 6, 8, 10, or 12.

The ILP gene of the present invention may be a gene comprising DNA which hybridizes under stringent conditions to DNA comprising a nucleotide sequence complementary to DNA consisting of the nucleotide sequence as shown in SEQ ID NO: 1, 3, 5, 7, 9, or 11 and which encodes a protein having endoreduplication promoting activity.

The term "stringent conditions" refers to conditions under which what is called a specific hybrid is formed but a non-specific hybrid is not formed. For example, under such conditions, complementary strands of DNA consisting of a highly homologous nucleic acid, i.e., DNA consisting of a nucleotide sequence exhibiting 80% or higher, preferably 85% or higher, more preferably 90% or higher, and most preferably 95% or higher homology to the nucleotide sequence as shown in any of SEQ ID NO: 1, 3, 5, 7, 9, or 11, hybridize, but complementary strands of a nucleic acid having homology lower than the aforementioned level do not hybridize. More specific conditions are constituted by a sodium salt concentration of 15 mM to 750 mM, and preferably 50 mM to 750 mM, and more preferably 300 mM to 750 mM, and a temperature of 25° C. to 70° C., preferably 50° C. to 70° C., and more preferably 55° C. to 65° C., and a formamide concentration of 0% to 50%, preferably 20% to 50%, and more preferably 35% to 45%. Under stringent conditions, further, the filter is washed after hybridization generally at a sodium salt concentration of 15 to 600 mM, preferably 50 to 600 mM, and more preferably 300 to 600 mM and a temperature of 50° C. to 70° C., preferably 55° C. to 70° C., and more preferably 60° C. to 65° C.

A person skilled in the art can readily obtain such homolog genes with reference to, for example, Molecular Cloning (Sambrook, J. et al., Molecular Cloning: A Laboratory Manual 2nd ed., Cold Spring Harbor Laboratory Press, 10 Skyline Drive Plainview, N.Y., 1989). Also, homology of the above sequences can be determined via a FASTA or BLAST search.

The ILP gene used in the present invention can be obtained as a nucleic acid fragment via PCR amplification with the use of primers designed based on the nucleotide sequence information and nucleic acids as templates obtained from a cDNA library, genomic DNA library, or the like. Also, the ILP gene can be obtained as a nucleic acid fragment via hybridization using the nucleic acid obtained from the library as a template and a DNA fragment, which is part of the ILP gene, as a probe. Alternatively, the ILP gene may be synthesized as a nucleic acid fragment via various techniques of nucleic acid synthesis, such as chemical synthesis, known in the art.

The amino acid can be deleted, added, or substituted by modifying the gene encoding the protein by a technique known in the art. Mutation can be introduced into a gene via conventional techniques such as the Kunkel method or the Gapped duplex method, or via a technique in accordance therewith. For example, mutation may be introduced using a mutagenesis kit, such as a Mutant-K (Takara) or Mutant-G (Takara), utilizing site-directed mutagenesis or the Takara LA PCR in vitro Mutagenesis series kit (Takara).

2. Recombinant Vector

The recombinant vector according to the present invention that is used for plant transformation can be constructed by introducing the ILP gene (hereafter, this may be referred to as "the target gene") into an adequate vector. For example, pBI, pPZP, and pSMA vectors that can introduce the target gene into a plant via *Agrobacterium* are preferably used. A pBI binary vector or intermediate vector is particularly preferable, and examples thereof include pBI121, pBI101, pBI101.2, and pBI101.3. A binary vector is a shuttle vector that can be replicated in *E. coli* and in *Agrobacterium*. When *Agrobacterium* containing a binary vector is allowed to infect plants, DNA in the portion sandwiched between border sequences consisting of the LB sequence and the RB sequence on the vector can be incorporated into the plant nuclear DNA. In contrast, a pUC vector can be used to directly introduce a gene into plants. Examples thereof include pUC18, pUC19, and pUC9 vectors. Plant virus vectors, such as cauliflower mosaic virus (CaMV), bean golden mosaic virus (BGMV), and tobacco mosaic virus (TMV) vectors, can also be used.

When a binary vector plasmid is used, the target gene is inserted between the border sequences (LB and RB sequences) of the binary vector, and this recombinant vector is then amplified in *E. coli*. Subsequently, the amplified recombinant vector is introduced into *Agrobacterium tumefaciens* GV3101, C58, LBA4404, EHA101, EHA105, or the like or *Agrobacterium rhizogenes* LBA1334 via electroporation or other means, and the aforementioned *Agrobacterium* is used for genetic transduction of plants.

The three-member conjugation method (Nucleic Acids Research, 12:8711, 1984) may also be used in addition to the method described above to prepare an *Agrobacterium* to infect plants containing the target gene. Specifically, plasmid-containing *E. coli* comprising the gene of interest, helper plasmid-containing *E. coli* (e.g., pRK2013), and an *Agrobacterium* are mixed and cultured on a medium containing rifampicin and kanamycin. Thus, a zygote *Agrobacterium* to infect plants can be obtained.

In order to insert the target gene into a vector, for example, a method may be employed in which the purified DNA is cleaved with an appropriate restriction enzyme and then inserted into the restriction site or the multi-cloning site of an appropriate vector DNA for ligation to the vector.

The target gene needs to be incorporated into a vector in a manner such that functions of the gene are exhibited. A promoter, an enhancer, a terminator, or a replication origin used for binary vector system (e.g., a replication origin derived from a Ti or Ri plasmid), a selection marker gene, or the like can be ligated to the vector at a site upstream, inside, or downstream of the target gene.

It is possible for the "promoter" to not be derived from plants, as long as the DNA can function in plant cells and can induce expression in a specific plant tissue or during a specific growth phase. Specific examples thereof include a cauliflower mosaic virus (CaMV) 35S promoter, a nopalin synthase gene promoter (Pnos), a maize ubiquitin promoter, a rice actin promoter, and a tobacco PR protein promoter.

An example of an enhancer is an enhancer region that is used for improving the expression efficiency of the target gene and that comprises the upstream sequence in the CaMV 35S promoter.

Any terminator can be used as long as it can terminate transcription of the gene transcribed by a promoter. Examples thereof include a nopalin synthase (NOS) gene terminator, an octopine synthase (OCS) gene terminator, and a CaMV 35S RNA gene terminator.

Examples of a selection marker gene include an ampicillin resistant gene, a neomycin resistant gene, a hygromycin resistant gene, a bialaphos resistant gene, and a dihydrofolate reductase gene.

The selection marker gene and the target gene may be ligated to the same plasmid to prepare a recombinant vector as described above. Alternatively, a recombinant vector that is obtained by ligating the selection marker gene to a plasmid may be prepared separately from a recombinant vector that is obtained by ligating the target gene to a plasmid. When recombinant vectors are separately prepared, both vectors are cotransfected into a host.

3. Transgenic Plant and Method for Preparing the Same

The transgenic plant according to the present invention can be prepared by introducing the gene or recombinant vector into the target plant. In the present invention, "gene introduction" refers to introduction of the target gene into a cell of the host plant via, for example, a conventional gene engineering technique, so that the gene can be expressed therein. The introduced gene may be incorporated into the genomic DNA of the host plant or may be present while remaining contained in a foreign vector.

The gene or recombinant vector can be adequately introduced into a plant via a variety of reported and established techniques. Examples thereof include the *Agrobacterium* method, the PEG-calcium phosphate method, electroporation, the liposome method, the particle gun method, and microinjection. The *Agrobacterium* method may employ a protoplast, a tissue section, or a plant itself (the in planta method). When a protoplast is employed, the protoplast is cultured together with the *Agrobacterium* (*Agrobacterium tumefaciens* or *Agrobacterium rhizogenes*) having a Ti or Ri plasmid, or it is fused with a spheroplasted *Agrobacterium* (the spheroplast method). When a tissue section is employed, *Agrobacterium* is allowed to infect a leaf section (a leaf disc) of an aseptically cultivated target plant or a callus (an undifferentiated cultured cell). When the in planta method that utilizes seeds or plants is employed, i.e., a method that is not carried out via tissue culture with the addition of phytohormones, *Agrobacterium* can be directly applied to water absorptive seeds, seedlings, potted plants, and the like. Such plant transformation can be carried out in accordance with a description of a general textbook, such as "Experimental protocols of model plants (New edition), Shimamoto, K. and Okada, K (e.d.), From Genetic engineering to genomic analysis, 2001, Shujunsha."

Whether or not the gene has been incorporated into the plant can be confirmed via PCR, Southern hybridization, Northern hybridization, Western blotting, or other means. For example, DNA is prepared from a transgenic plant, an ILP gene-specific primer is designed, and PCR is then carried out. After PCR has been carried out, the amplification product is subjected to agarose gel electrophoresis, polyacrylamide gel electrophoresis, or capillary electrophoresis and stained with ethidium bromide, a SYBR Green solution, or the like, thereby allowing detection of the amplification product as a band. Thus, transformation can be confirmed. Alternatively, the amplification product can be detected via PCR with the use of a primer that has been previously labeled with a fluorescent dye or the like. Further, the amplification product may be bound to a solid phase such as a microplate to thereby confirm the amplification product via fluorescent or enzyme reactions. Further, the protein may be extracted from the plant cell, two-dimensional electrophoresis may be carried out to fractionate the protein, and a band of the protein encoded by the ILP gene may be detected. Thus, expression of the ILP gene that has been introduced into the plant cell; i.e., transformation of the plant, may be confirmed. Subsequently, the amino acid sequence at the N terminus of the detected protein may be determined via Edman degradation or other means to confirm whether or not the amino acid sequence is consistent with the amino acid sequence at the N terminus of SEQ ID NO: 2, 4, 6, 8, 10, or 12. Thus, transformation of the plant cell can further be verified.

Alternatively, a variety of reporter genes, such as β-glucuronidase (GUS), luciferase (LUC), green fluorescent protein (GFP), chloramphenicol acetyltransferase (CAT), or β-galactosidase (LacZ), are ligated to the downstream region of the target gene to prepare a vector. *Agrobacterium* to which the aforementioned vector has been incorporated is used to transform a plant in the same manner as described above, and the expression of the reporter gene is assayed. Thus, incorporation of the gene into the plant can be confirmed.

In the present invention, monocotyledonous plants or dicotyledonous plants may be used for transformation. Examples thereof include, but are not limited to, those belonging to: *Brassicaceae* such as *Arabidopsis thaliana*, cabbage, and rapeseed; Gramineae such as rice, maize, barley, and wheat; Solanaceae such as tomato, eggplant, potato, and tobacco; Leguminosae such as soybean, garden pea, and bush bean; Convolvulaceae such as sweet potato; Euphorbiaceae such as *Manihot utilissima*; and Rosaceae such as strawberry.

In the present invention, examples of plant materials to be transformed include: plant organs, such as a stem, leaf, seed, embryo, ovule, ovary, and shoot apex; plant tissues, such as anther or pollen, and sections thereof; undifferentiated calluses; and cultured plant cells such as protoplasts prepared by removing cell walls via enzyme processing. When the in planta method is employed, water absorptive seeds or a whole plant can also be used.

A transgenic plant in the present invention refers to a whole plant, a plant organ (e.g., a leaf, petal, stem, root, grain, or seed), a plant tissue (e.g., the epidermis, phloem, parenchyma, xylem, or vascular bundle), or a cultured plant cell (e.g., callus).

When a cultured plant cell is to be transformed, an organ or individual may be regenerated from the obtained transformed cell via conventional tissue culture techniques. A person skilled in the art can easily carry out such procedures via a common technique that is known as a method of regenerating a plant from a plant cell. For example, a plant can be regenerated from a plant cell in the following manner.

At the outset, when plant tissues or protoplasts are used as plant materials to be transformed, they are cultured in a callus-forming medium that has been sterilized with the addition of, for example, inorganic elements, vitamins, carbon sources, saccharides as energy sources, or plant growth regulators (plant hormones, such as auxin, cytokinin, gibberellin, abscisic acid, ethylene, or brassinosteroid), and indeterminately proliferating dedifferentiated calluses are allowed to form (hereafter, this process is referred to as "callus induction"). The thus formed calluses are transferred to a fresh medium containing plant growth regulators, such as auxin, and then further proliferation takes place (i.e., subculture).

Callus induction is carried out on a solid medium such as agar, and subculture is carried out in, for example, a liquid medium. This enables both cultures to be carried out efficiently and in large quantities. Subsequently, the calluses proliferated via the aforementioned subculture are cultured under adequate conditions to induce redifferentiation of organs (hereafter referred to as "induction of redifferentiation"), and a complete plant is finally regenerated. Induction of redifferentiation can be carried out by adequately determining the type and quantity of each ingredient in the medium, such as plant growth regulators such as auxin and carbon sources, light, temperature, and other conditions. Such induction of redifferentiation results in formation of adventitious embryos, adventitious roots, adventitious buds, adventitious shoots, and the like, which further leads to growth into complete plants. Alternatively, such items may be stored in a state that corresponds to conditions before they become complete plants (e.g., encapsulated artificial seeds, dry embryos, or freeze-dried cells and tissues).

The transgenic plant of the present invention includes a progeny plant obtained via sexual reproduction or asexual reproduction of a plant into which the gene of interest has been introduced (including a plant regenerated from a transgenic cell or callus) and part of a tissue or organ of a progeny plant (e.g., a seed or protoplast). The transgenic plant of the present invention can be mass-produced by obtaining reproduction materials, such as seeds or protoplasts, from plants transformed via introduction of the ILP gene and cultivating or culturing the same.

In the thus-obtained transgenic plant, the nuclear DNA content in the plant cell increases via expression of the ILP gene. As a result, breeding of the enlarged transgenic plant of interest can be realized. The present invention, accordingly, provides a method comprising introducing the ILP gene or a homolog gene thereof into a plant and causing the same to overexpress in the plant, thereby enlarging the entire plant or a part thereof.

BEST MODES FOR CARRYING OUT THE INVENTION

Hereafter, the present invention is described in greater detail with reference to the following examples, although the technical scope of the present invention is not limited thereto.

[Material and Method]

The materials and the methods employed in the examples below are as follows.

(1) Plant Material and Growth Conditions

All plants were grown on a GM plate comprising 10 mg/ml of sucrose with or without antibiotics (G M, Valvekens, D., Van Montagu, M., and Van Lijsebettens, M., 1988, *Agrobacterium tumefaciens*-mediated transformation of *Arabidopsis thaliana* root explants by using kanamycin selection. Proc. Natl. Acad. Sci., U.S.A., 85, 5536-5540). Plants were grown in a temperature-controlled incubation chamber under a white light (15 $W/m^2$ of white light for light-grown cotyledons or 5 $W/m^2$ of white light for light-grown hypocotyls) or under complete darkness at 22° C. The SALK T-DNA-inserted mutants were subjected to backcross with Col-0 twice and then subjected to purification for a physiological experiment.

(2) Ploidy Analysis

Nuclei were extracted and stained with CyStain UV precise P (Partec GmbH, Munster, Germany) in accordance with the manufacturer's protocol. Flow cytometric analysis was carried out using the Ploidy Analyser (Partec GmbH, Munster, Germany).

(3) Preparation of ILP1, 2, 3, 4, 5, and 7-overexpressing Transgenic Lines cDNAs spanning the full coding regions of the genes were amplified via PCR using the primers shown below obtained from the Super Script *Arabidopsis* cDNA library (Invitrogen, California).

```
(For ILP1 amplification)
ILP1-F:
                                        (SEQ ID NO: 13)
5'-GGGGTACCATGGGAAGTAACCGTCCTAAG-3'

ILP1-R:
                                        (SEQ ID NO: 14)
5'-ACGCGTCGACTCAAACTGCCTCCTTAAGATT-3'

(For ILP2 amplification)
ILP2-F:
                                        (SEQ ID NO: 15)
5'-GGGGTACCGGAAAATGGGTAGCAAGATG-3'

ILP2-R:
                                        (SEQ ID NO: 16)
5'-CGAGCTCAGGGTTTAAGCTTGGCTTCC-3'
```

-continued (For ILP3 amplification)
ILP3-F:
(SEQ ID NO: 17)
5'-GGGGACAAGTTTGTACAAAAAAGCAGGCTTCATGGATTCTCTCGCTC
TCGC-3'

ILP3-R:
(SEQ ID NO: 18)
5'-GGGGACCACTTTGTACAAGAAAGCTGGGTATTTCTCCCGACCAAAC
T-3'

(For ILP4 amplification)
ILP4-F:
(SEQ ID NO: 19)
5'-GGGGACAAGTTTGTACAAAAAAGCAGGCTTCATGAAGCAGAAGGGTT
TTAAA-3'

ILP4-R:
(SEQ ID NO: 20)
5'-GGGGACCACTTTGTACAAGAAAGCTGGGTCCTATATTGGATTCATGA
CAAC-3'

(For ILP5 amplification)
ILP5-F:
(SEQ ID NO: 21)
5'-GGGGACAAGTTTGTACAAAAAAGCAGGCTTCATGGTGAATCAAAGAA
AGCTA-3'

ILP5-R:
(SEQ ID NO: 22)
5'-GGGGACCACTTTGTACAAGAAAGCTGGGTCTTAACACACCATTCCAT
CCCT-3'

(For ILP7 amplification)
ILP7-F:
(SEQ ID NO: 23)
5'-GGGGACAAGTTTGTACAAAAAAGCAGGCTTCATGCCGGCGAATGATG
CTGAA-3'

ILP7-R:
(SEQ ID NO: 24)
5'-GGGGACCACTTTGTACAAGAAAGCTGGGTCTCATACTCCCTCAGCTG
CCAA-3'

The obtained cDNAs of ILP1 and ILP2 were digested with KpnI and SalI or SacI and cloned into the yy45 vector (Yamamoto, Y. Y., Deng, X. W., and Matsui, M., 2001, CIP4, a new COP1 target, is a nucleus-localized positive regulator of *Arabidopsis* photomorphogenesis. Plant Cell 13, 399-411) as a derivative of pPZPY122 (Yamamoto, Y. Y et al. as above).

cDNAs of ILP3, 4, 5, and 7 were amplified via PCR using the above primer sets. The amplified PCR fragment was cloned into the pDONR207 vector (Invitrogen Corp., Carlsbad, Calif., USA) in a BP reaction of Gateway cloning. The pDONR207 vector into which cDNA has been integrated was cloned into the pBI pBIDAVL-GWR1 binary vector (Nakazawa M, Ichikawa T, Ishikawa A, Kobayashi H, Tsuhara Y, Kawashima M, Suzuki K, Muto S, Matsui M., Activation tagging, a novel tool to dissect the functions of a gene family. Plant J. 2003, 34: 741-750) in a Gateway cloning LR reaction.

The prepared binary vector was transfected into *Agrobacterium tumefaciens* (the GV3101 strain) via electroporation. In the case of the yy45 vector, the transgenic plant was selected on LB medium supplemented with 70 μg/ml of chloramphenicol. *Agrobacterium* into which pBIDAVL-GWR1 had been introduced was selected on 25 mg/ml of kanamycin medium. The *Arabidopsis thaliana* WT (Col-0) strain was transformed by the floral dip method (Clough, S. J., and Bent, A. F., 1998, Floral dip: a simplified method for *Agrobacterium*-mediated transformation of *Arabidopsis thaliana*, Plant J. 16, 735-743). The seedlings into which yy45 had been transfected were selected on GM supplemented with 50 μg/l of kanamycin and 100 μg/l of cephalotaxime. The seedlings into which pBIDAVL-GWR1 had been introduced were selected on GM containing 50 μg/l hygromycin and on GM containing 100 μg/l of cephalotaxime.

(4) Localization of Intracellular Proteins

GFP was amplified from yy217 using the primers shown below (GFPn-F and GFPn-R) to be used for ILP1:GFP.

(For GFP amplification)
GFPn-F:
(SEQ ID NO: 25)
5'-TCTAGAGGATCCCCCGGGGGTACCGTCGACATGGCAATGAGTAAAGG
AGAA-3'

GFPn-R:
(SEQ ID NO: 26)
5'-CGAGCTCTTATTTGTAAAGTTCATC-3'

The GFP fragment was digested with XbaI and Sad and cloned into yy45 (yy45GFPn).

ILP1 cDNA was amplified from the Super Script *Arabidopsis* cDNA library using the ILP1-F and ILP-R2-SAL primers (5'-ACGCGTCGACAACTGCCTCCTTAAGATTG-3': SEQ ID NO: 27) and cloned into the KpnI and the SalI sites of yy45GFPn to prepare ILP1:GFP. Onion epidermal cells were peeled and placed on a GM plate. The ILP1:GFP constructs were loaded on gold particles (diameters: 1 μm) in accordance with the manufacturer's protocol. The particles were delivered to the onion epidermal cells using the Biolistic PDS-1000/He system (BIO-RAD, California). The impact parameters were set at a rupture disc bursting pressure of 600 psi and a distance to the target tissue of 9 cm. GFP fluorescence was observed under the BX60 microscopy (Olympus, Tokyo, Japan) 18 hours and 36 hours after the impact application.

(5) Semi-quantitative RT-PCR and Real-time PCR Analysis (5-1) Semi-quantitative RT-PCR Semi-quantitative reverse-transcription PCR (RT-PCR) analysis was carried out as described in the published document (Kimura, M., Yoshizumi, T., Manabe, K., Yamamoto, Y. Y., and Matsui, M., 2001, *Arabidopsis* transcriptional regulation by light stress via hydrogen peroxide-dependent and -independent pathways, Genes Cells 6, 607-617). Seeds were sowed on a GM plate supplemented with sucrose, the plate was treated for 5 days, and incubation was then carried out at 22° C. under a white light for 3 days. The seedlings were harvested and total RNA was isolated as described in the published document (Yoshizumi, T., Nagata, N., Shimada, H., and Matsui, M., 1999, An *Arabidopsis* cell cycle-dependent kinase-related gene, CDC2b, plays a role in regulating seedling growth in darkness, Plant Cell 11, 1883-1896).

When expression of cell-cycle-related genes was analyzed (FIG. 6A), existing primer sets were used for gene amplification. The primer sets used for amplifying cDNA of CYCA2;1, CYCB1;2, and CYCD3;1 are described in Richard, C., Granier, C., Inzé, D., and De Veylder, L., 2001, Analysis of cell division parameters and cell cycle gene expression during the cultivation of *Arabidopsis thaliana* cell suspensions, J. Exp. Bot. 52, 1625-1633. The primer sets used for amplifying cDNA of HISH4 are described in Mariconti, L., Pellegrini, B., Cantoni, R., Stevens, R., Bergounioux, C., Cella, R., and Albani, D., 2002, The E2F family of transcription factors from *Arabidopsis thaliana*, Novel and conserved components of the retinoblastoma/E2F pathway in plants, J. Biol. Chem. 277, 9911-9919. The primer sets used for amplifying cDNA of ACT2 are described in Himanen, K., Boucheron, E., Vanneste, S., de Almeida Engler, J., Inze, D., and Beeckman, T., 2002, Auxin-mediated cell cycle activation during early lateral root initiation, Plant Cell 14, 2339-2351.

CYCA2;1 expression in the mutants into which T-DNA of CYCA2;1 has been inserted (i.e., cyca2; 1-1 and cyca2; 1-1) was analyzed with the use of the following primer set (FIG. 8B). ILP1 expression in ilp1-1D and ILP1ox was analyzed with the use of the primer set as shown in SEQ ID NOs: 13 and 14 (FIG. 4B).

```
(For CYCA2; 1 amplification)
CycA2; 1-F:
                                          (SEQ ID NO: 28)
5'-GGACTAGTGAGCTCGCACACTAATGCGAAGAAAG-3'

CycA2; 1-R:
                                          (SEQ ID NO: 29)
5'-CCGCTCGAGTCTAGAGCAGATGCATCTAAAGATTC-3'
```

(5-2) Real-time PCR Analysis

Real-time PCR was carried out in accordance with the protocol of Mx3000P (SIRATAGENE, CA).

As described above, total RNA was isolated from seedlings using TRIzol (Invitrogen, CA), and the isolated total RNA was used as a template to synthesize the first strand cDNA using the SuperScript first-strand synthesis system (Invitrogen, CA) in accordance with the manufacturer's instructions. PCR analysis was carried out with the use of the SYBR Green Realtime PCR Master Mix (TOYOBO, Osaka, Japan) via the Mx3000P multiplex quantitative PCR system (STRATAGENE, CA). The following primer sets were used in order to inspect the expression levels of the ILP1 gene (FIG. 3B and FIG. 6C) and the CYCA2 gene family (FIG. 6B and FIG. 6D).

```
(For ILP1 amplification)
ILP1realF:
5'-AGCTTGCCAAGAAGGCATTG-3'          (SEQ ID NO: 30)

ILP1realR:
5'-TCATCAACGACGCAGTCAGA-3'          (SEQ ID NO: 31)

(For CYCA2; 1 amplification)
CycA2; 1-F:
5'-CGCTTCAGCGGTTTTCTTAG-3'          (SEQ ID NO: 32)

CycA2; 1-R:
5'-ATCCTCCATTGCAAGTACCG-3'          (SEQ ID NO: 33)

(For CYCA2; 2 amplification)
CycA2; 2-F:
5'-TGTATGTGTTGGCCGTAATG-3'          (SEQ ID NO: 34)

CycA2; 2-R:
5'-TGGTGTCTCTTGCATGCTTA-3'          (SEQ ID NO: 35)

(For CYCA2; 3 amplification)
CycA2; 3-F:
5'-CTCTATGCCCCTGAAATCCA-3'          (SEQ ID NO: 36)

CycA2; 3-R:
5'-ACCTCCACAAGCAATCAAC-3'           (SEQ ID NO: 37)

(For CYCA2: 4 amplification)
CycA2; 4-F:
5'-CAAAGCCTCCGATCTCAAAG-3'          (SEQ ID NO: 38)
```

-continued

```
CycA2; 4-R:
5'-CTTGTCCGGTAGCTCTCCAG-3'          (SEQ ID NO: 39)

(For CYCA1: 1 amplification)
CycA1; 1-F:
5'-CGATGACGAAGAAACGAGCA-3'          (SEQ ID NO: 40)

CycA1; 1-R:
5'-TGGCATTAACGCAAACACTTG-3'         (SEQ ID NO: 41)

(For ACT2 amplification)
Act2-F:
5'-CTGGATCGGTGGTTCCATTC-3'          (SEQ ID NO: 42)

Act2-R:
5'-CCTGGACCTGCCTCATCATAC-3'         (SEQ ID NO: 43)
```

(6) Optical Microscopy

Plant materials were immobilized in 4% paraformaldehyde in a buffer containing 20 mM sodium cacodylate at 4° C. for 24 hours, dehydrated with an ethanol sereies, and then embedded into the Technovit 7100 resin (Kulzer and Co., Wehrheim, Germany). The sections (thickness: 2.5 μm) were cut with a glass knife on a ultramicrotome, placed on a cover slip, and then dried. The resultants were stained with 1% toluidine blue in 0.1 M phosphate buffered-physiological saline (pH 7.0) for 30 seconds, followed by washing with distilled water for 10 seconds. The samples were observed under an Olympus 1×70 microscope (Olympus, Tokyo, Japan).

(7) In Vivo Transcription Assay

The region from −150 to +5 of the NOS promoter was amplified by PCR from the pMA560 (Ma, J., Przibilla, E., Hu, J., Bogorad, L., and Ptashne, M., 1988, Yeast activators stimulate plant gene expression. Nature 334, 631-633) using the following primers: 5'-GGG GGA TCC GCG GGT TTC TGG AGT TTA ATG-3' (SEQ ID NO: 44) and 5'-CCT CTA GAG ACT CTA ATT GGA TAC CGA GG-3' (SEQ ID NO: 45). The amplified fragment was digested with BamHI and XbaI and cloned into the BamHI/XbaI site of yy76 (Yamamoto, Y. Y., and Deng, X. W., 1998, A new vector set for GAL4-dependent transactivation assay in plants, Plant Biotech. 15, 217-220). The second BamHI site located between the XbaI site and GUS in the resulting clone was maintained. The clone, yy78, was digested with BamHI/and HindIII and cloned into the BamHI/HindIII site of pBIL221 (Nakamura, M., Tsunoda, T., and Obokata, J., 2002, Photosynthesis nuclear genes generally lack TATA-boxes: a tobacco photosystem I gene responds to light through an initiator, Plant J. 29, 1-10) to obtain yy97. The yy97 plasmid was prepared from the GM2163 ($Dam^-/Dcm^-$) line for this assay. In order to prepare effector plasmids, ILP1 cDNA of various lengths was amplified with the use of ILP1-F and ILP1-R primers for GAL-ILP1 Full, with the use of ILP1-F and ILP1-No 2-R (5'-GGGGTACCTTAGGATCCGTCACTCTCATCAGTGCT-3': SEQ ID NO: 46) primers for GAL4-ILP1N, and with the use of ILP1-No 5-F (5'-GCTCTAGAGGATCCATGACAGT-TCTAAACAAACAT-3': SEQ ID NO: 47) and ILP1-R primers for GAL4-ILP1C. The obtained cDNA was digested with KpnI and SalI and cloned into the KpnI/SalI site of yy64 (Yamamoto, Y. Y., and Deng, X. W, 1998, A new vector set for GAL4-dependent transactivation assay in plants, Plant Biotech. 15, 217-220). Tobacco leaves (*Nicotiana tabacum* cv SR1) were subjected to biolistic bombardment in the manner described above. Luciferase activity was measured using the Lumat LB9507 luminometer (PerkinElmer, MA).

(8) Cell Culture and Transfection

Mouse NIH3T3 cells were cultured in DMEM medium (Invitrogen, CA) supplemented with 10% fetal bovine serum (FBS, Invitrogen, CA). NIH3T3 cells (about $2.0\times10^5$ cells)

were sowed in each well of a 12-well titer plate for transfection. After incubation in a $CO_2$ incubator (5% $CO_2$) for 2 days, transfection was carried out using Lipofectamine 2000 (Invitrogen, CA). Luciferase activity was assayed 24 hours and 48 hours after the transfection using the TD-20/20 luminometer (Promega, WI) in accordance with the manufacturer's protocol. The mouse ILP1 gene was amplified from the total RNA prepared from the NIH3T3 cells with the use of the following set of primers, and the amplified gene was confirmed via sequencing. The PCR fragment was cloned into pcDNA-DEST40 with the use of the GATE-WAY cloning system (Invitrogen, CA).

```
(For mouse ILP1 amplification)
Mouse ILP1F:
                                          (SEQ ID NO: 48)
5'-GGGGACAAGTTTGTACAAAAAAGCAGGCTTCGCCACCATGGACATG

GAGAGCGAGAAGG-3'

Mouse ILP1R:
                                          (SEQ ID NO: 49)
5'-GGGGACCACTTTGTACAAGAAAGCTGGGTCCTATTTTCCTTCAATCA

GAGACTT-3'
```

[Results]

EXAMPLE 1

Classification of Endoreduplication Mutants

Dark-grown *Arabidopsis* seedlings were used and the ploidy levels of hypocotyl cells were measured. To define the screening conditions, the ethylene signal transduction mutant ctr1-1 was used as a positive control (Gendreau, E., Trans, J., Desnos, T., Grandjean, O., Caboche, M., and Hofte, H., 1997, Cellular basis of hypocotyl growth in *Arabidopsis thaliana, Plant Physiol.* 114, 295-305). The 32C peak was significantly increased in dark-grown ctr1-1 hypocotyls. Other ploidy peaks, including 2C, 4C, 8C, and 16C, also appeared in ctr1-1 as they did in the wild type (Col-0) but at different ratios (FIG. 1A) (Gendreau, E. et al., 1997, the same as above; Orbovic, V., Höfte, H., and Traas, J., 1999, Gibberellin and ethylene control endoreduplication levels in the *Arabidopsis thaliana* hypocotyl, Planta 209, 513-516). Under the screening conditions with sucrose in the growth plates, cells with ploidy levels as high as 32C in dark-grown hypocotyls were observed.

The relative ratios of 8C/32C and 16C/32C of ctr1-1 and the wild type were calculated. In order to reproduce the inheritance of a dominant mutation exhibiting its phenotype in heterozygotes, ctr1-1 seedlings were mixed with the wild type at a ratio of 7 to 3 instead of 3 to 1. The above relative ratios were calculated regarding the resultant. The screening criteria were set to be less than 1.0 for 8C/32C and less than 2.0 for 16C/32C (FIG. 1B). These values were used for the isolation of dominant polyploid mutants.

Approximately 20 seedlings were used for each $T_2$ activation tagging line. In the present screening, it is difficult to isolate recessive mutants since recessive mutants will appear in only one-quarter of the T2 seeds, and, at this frequency, any difference in ploidy levels will be buried in wild-type patterns. For gain-of-function or dominant mutations, the mutant siblings appear in three-quarters of the population and can be monitored by flow cytometric assay. Dark-grown seedlings were used for this assay because they were easy to harvest and conditions were reproducible.

Seventeen dominant mutants were isolated from 4500 independent activation tagging lines (Nakazawa, M., Ichikawa, T., Ishikawa, A., Kobayashi, H., Tsuhara, Y., Kawashima, M., Suzuki, K., Muto, S., and Matsui, M., 2003, Activation tagging, a novel tool to dissect the functions of a gene family, Plant J. 34, 741-750; Ichikawa, T., Nakazawa, M., Kawashima, M., Muto, S., Gohda, K., Suzuki, K., Ishikawa, A., Kobayashi, H., Yoshizumi, T., Tsumoto, Y., Tsuhara, Y, Iizumi, H., Goto, Y., and Matsui, M., 2003, Sequence database of 1172 T-DNA insertion sites in *Arabidopsis* activation-tagging lines that showed phenotypes in T1 generation, Plant J. 36, 421-429; http://rarge.gscsiken.jp/activation-tag/top.php).

These mutants had an increased number of ploidy cells and showed a high 32C ploidy peak in the hypocotyls of dark-grown seedlings like the ctr1-1 mutant. These 17 mutants were divided into two groups according to hypocotyl length, root length, and dependency on light. They were designated as Group 1 and Group 2 (Table 1).

TABLE 1

Two groups of ploidy mutants

| | Ploidy (darkness, hypocotyl) | Ploidy (light, cotyledon) | Hypocotyl length (darkness) | Root length (darkness) | Other features |
|---|---|---|---|---|---|
| Group 1 | + | + | − | + | Large cotyledon Thick hypocotyl |
| Group 2 | + | − | + | + | |

(+: increase; −: not different from wild-type (Col))

Twelve mutants belonging to Group 1 showed increased ploidy levels in both dark- and light-grown seedlings compared with the wild type. They had longer roots, but the hypocotyl length was almost the same as the wild type. In Group 2, five mutants had increased ploidy levels only in the dark, and they had almost the same ploidy levels as the wild type in light. This indicates that the Group 2 phenotype is light dependent. They also had longer hypocotyls than dark-grown seedlings.

EXAMPLE 2

Characterization of Dominant Mutant ilp1-1D

A dominant mutant Z010521 that was designated as increased level of polyploidyl-1D (ilp1-1D) belonging to Group 1 was characterized. The hypocotyls of dark-grown seedlings contained cells with ploidy levels as high as 32C in the above assay (FIG. 2A). Homozygous ilp1-1D also contained cells with levels as high as 32C, but the ratio of the 32C peak was greater compared with the wild type (isogenic siblings that did not undergo T-DNA insertion) in the dark (FIG. 2A). This result was more apparent compared with a case in which the total cell numbers for each ploidy level were compared (FIG. 2B). In dark-grown hypocotyls, the percentage of cells represented by 32C cells was significantly increased in ilp1-1D compared with the wild type. In ilp1-1D, the values of 8C/32C and 16C/32C were 0.44 and 1.3, respectively, indicating that the mutant falls into the designated screening category. This result showed that the degree of endoreduplication was increased in this mutant.

The increased nuclear volume was measured by staining dark-grown hypocotyls with 4',6-diamidino-2-phenylindole (DAPI). ilp1-1D seedlings had much enlarged nuclei compared with the wild type (FIG. 2C and FIG. 2D). In light conditions, wild-type hypocotyls contained cells with levels of up to 16C in the assay, and the percentage of cells represented by 16C cells was increased in ilp1-1D (FIG. 2B). Cotyledons of light-grown ilp1-1D also had an increased number of 16C cells, as did the hypocotyl cells (FIG. 2B).

EXAMPLE 3

Analysis of ilp1-1D Phenotype

The ilp1-1D phenotype was compared with the wild type in the light and in the dark. The ilp1-1D homozygous lines did not show differences in hypocotyl length compared with the wild type when grown in the dark (FIG. 2E and FIG. 2F). Instead of elongating, ilp1-1D hypocotyls became thicker than that of the wild type, indicating that cells increased their volume along their horizontal axis (FIG. 2G). The cells in the hypocotyls were examined by making transverse sections. The cortical and endodermal cells of ilp1-1D were found to have increased diameters, resulting in thicker hypocotyls compared with the wild type (FIG. 2H and FIG. 2I). There was almost no difference in the number of cells contained in the cortex and endodermis. These results indicated that the rise in the ploidy level in ilp1-1D increased the diameter of hypocotyl cells, resulting in an increase in cell volume.

In addition to these hypocotyl phenotypes, an increase in primary root length was observed (FIG. 2E and FIG. 2F).

In light-grown seedlings, the ilp1-1D homozygous mutant showed greatly expanded cotyledons compared with the wild type (FIG. 2J to FIG. 2L). The number of cells was examined along the major and minor axes of the cotyledons. There was no difference in cell number between ilp1-1D and the wild type, indicating that the large cotyledon size of the mutant was caused by an increase in individual cell size and not by an increase in cell number. Adult ilp1-1D plants were almost the same height as those of the wild type.

EXAMPLE 4

Analysis of ILP1 Gene Structure (1) Selection of Candidate Gene

The activation T-DNA contains the hygromycin resistant gene as a selection marker. As a result of examination of $T_2$ progenies of ilp1-1D heterozygous plants, approximately 70% of the progeny was found to exhibit hygromycin resistance, suggesting that there was only one T-DNA in the genome. All the hygromycin-resistant plants showed increased ploidy levels in the $T_3$ generation. These results strongly suggest that the activation-tagged T-DNA was responsible for the increased polyploidy phenotype. The T-DNA flanking sequence was isolated by plasmid rescue. After sequencing, the T-DNA was inserted in the coding region of AT5g08560 (FIG. 3A). The distances between the putative initiation codons and the right border (RB) of the T-DNA were approximately 1 kb for AT5g08550 and approximately 7.4 kb for AT5g08560 (FIG. 3A). Expression of AT5g08550 in a heterozygote of ilp1-1D and the wild type was examined by real-time PCR. As a result, expression was found to be 13 times higher in ilp1-1D than in the wild type (FIG. 3B). To determine whether or not the insertion in AT5g08560 caused the increased polyploidy level, a T-DNA insertion line was inspected from the SALK T-DNA collections (SALK_095495) (Alonso, J. M., Stepanova, A. N., Leisse, T. J., Kim, C. J., Chen, H., Shinn, P., Stevenson, D. K., Zimmerman, J., Barajas, P., Cheuk, R, et al., 2003, Genome-wide insertional mutagenesis of *Arabidopsis thaliana*, Science 301, 653-657). The T-DNA was inserted in the first exon in AT5g08560 (data not shown). This line did not show an altered polyploidy level (data not shown). Based on these results, AT5g08550 was determined to be a candidate for the gene responsible for the activation phenotype of ilp1-1D.

(2) Identification of Candidate Gene AT5g08550

To confirm this, transgenic plants overexpressing the AT5g08550 cDNA isolated by RT-PCR under the control of the cauliflower mosaic virus 35S (CaMV 35S) promoter were generated. Eight out of 15 lines showed significantly increased ploidy levels in $T_2$ generation recapitulating the ilp1-1D phenotype. AT5g08550 was highly expressed in these lines (ILP1ox(#2)) (FIG. 3B). The ploidy of dark-grown seedlings of a homozygous line was examined. As a result, the relative ratio of the 32C peak was found to be increased, and cells as high as 64C were observed (FIG. 3C). Transgenic lines (#1 and #3) that did not show polyploidy phenotypes had almost the same ILP1 expression level as the wild type. AT5g08550 overexpression also reproduced the other phenotypes of ilp1-1D, such as enlarged cotyledons, thick hypocotyls, and elongated primary roots (FIG. 3H to FIG. 3J). However, there were almost no differences in adult plant height and seed size, compared with the wild type. These results strongly suggest that AT5g08550 is the corresponding gene for the ilp1-1D mutation. AT5g08550 was designated as ILP1.

The ILP1 gene encodes a protein of 908 amino acid residues. In order to identify conserved motifs, ILP1 homologs were searched for in the protein database using the BLASTP program. This search revealed that ILP1 had similarity to the C-terminal region of the GC-binding factor (GCF) of human and other species (FIG. 3D to FIG. 3F). The GCF protein was first isolated as a transcriptional repressor that bound to a GC-rich sequence in the promoter region of the epidermal growth factor receptor (EGFR), β-actin, and calcium-dependent protease genes (Kageyama, R., and Pastan, I., 1989, Molecular cloning and characterization of a human DNA binding factor that represses transcription, Cell 59, 815-825). However, the first reported GCF cDNA clone was a chimeric gene. The N terminus of the protein bound to a GC-rich region, and its C-terminal region was derived from another cDNA with unknown function (Reed, A. L., Yamazaki, H., Kaufman, J. D., Rubinstein, Y., Murphy, B., and Johnson, A. C., 1998, Molecular cloning and characterization of a transcription regulator with homology to GC-binding factor, J. Biol. Chem. 273, 21594-21602; Takimoto, M., Mao, P., Wei, G, Yamazaki, H., Miura, T., Johnson, A. C., and Kuzumaki, N., 1999, Molecular analysis of the GCF gene identifies revisions to the cDNA and amino acid sequences, Biochim. Biophys. Acta. 1447, 125-131).

To prevent confusion, the DNA binding domain is referred to as authentic GCF and the gene encoding the C-terminal region thereof is referred to as CTILP1 (for C-terminal region of ILP1). ILP1 shows homology to CTILP1. CTILP1 has paralogous genes in mouse, *Drosophila melanogaster*, and *Caenorhabditis elegans* (*C. elegans*) (FIG. 3E and FIG. 3F). ILP1 has a paralogous gene in the *Arabidopsis* genome (AT5g09210) (FIG. 3E and FIG. 3F). Two conserved motifs were found in ILP1 and other CTILP1 proteins. Motif 1 is at residues 371 to 465 of ILP1 (FIG. 3D and FIG. 3E), and motif 2 is at residues 571 to 852 (FIG. 3D and FIG. 3F). These two motifs are well conserved in CTILP1s of various species. Motif 2, in particular, is well conserved, but motif 1 is not found in proteins of *Drosophila* and *C. elegans*. Significant homology was not found in the N terminal region of CTILP1 proteins. No predicted features of these two motifs could be obtained even with the use of 3D-PSSM (Kelley, L. A., MacCallum, R. M., and Sternberg, M. J. E., 2000, Enhanced genome annotation using structural profiles in the program 3D-PSSM, J. Mol. Biol. 299, 499-520).

In these two conserved regions, a putative nuclear localization signal (NLS) was found using the PSORT program (Nakai, K., and Horton, P., 1999, PSORT: A program for detecting sorting signals in proteins and predicting their subcellular localization, Trends Biochem. Sci. 24, 34-36). This sequence is at residues 522 to 539 of ILP1 and is rich in arginine residues, which is a typical bipartite NLS (FIG. 3D). The presence of this putative NLS motif suggests that ILP1 is a nuclear protein. To confirm this prediction, ILP1 was expressed as a fusion protein with the N-terminal region of the green fluorescent protein (GFP) (ILP1:GFP) under the control of the CaMV 35S promoter. Localization in onion epidermal cells was examined by biolistic bombardment. The ILP1:GFP fusion protein was detected in the nucleus, indicating that ILP1 is a nuclear protein (FIG. 3G).

EXAMPLE 5

Phenotype of T-DNA Insertion Mutant of the ILP1 Gene

Two T-DNA insertion mutants were isolated from the SALK T-DNA insertion lines (Alonso, J. M., Stepanova, A. N., Leisse, T. J., Kim, C. J., Chen, H., Shinn, P., Stevenson, D. K., Zimmerman, J., Barajas, P., Cheuk, R, et al., 2003, Genome-wide insertional mutagenesis of *Arabidopsis thaliana*, Science 301, 653-657). Both mutants have T-DNA insertions in different positions in the 5th intron of ILP I (FIG. 3A, indicated by small triangles). Expression of the ILP1 gene in both these mutants was examined. Although a primer set (arrows in FIG. 3A) specific to the region did amplify a PCR product (data not shown), no expression was detected in lines when a primer set (ILP1-F and ILP1-R) for amplifying the full length was used (FIG. 4B). This indicates that these mutants lacked full-length transcripts rather than having null mutations. These homozygous mutants were designated as ilp1-1 (SALK_030650) and ilp1-2 (SALK_135563), respectively. Both ilp1-1 and ilp1-2 had shorter hypocotyls and roots, compared with their wild-type siblings in the dark (FIG. 4A, FIG. 4C, and FIG. 4E). In the light, they both showed shorter hypocotyls and smaller cotyledons, compared with the wild type, and there was inhibition of root elongation (FIG. 4D and FIG. 4E). ilp1-1, in which the T-DNA insertion is closer to the splicing acceptor site of the 5th intron, exhibited a more severe morphological phenotype than ilp1-2. To examine complementation of these lines, ilp1-1 and ilp1-2 were crossed with each other. The F1 plants also showed shorter hypocotyls and roots compared with the wild type both in the light and darkness (FIG. 4A and FIG. 4D). This result indicated that these lines were allelic, and loss of ILP1 caused the short hypocotyl phenotype. To address the relationship between ploidy and ILP1 function, the ploidy levels of heterozygous ilp1-1 and ilp1-2 were examined in the dark. Reduction in the number of 32C cells was observed in both ilp1-1 and ilp1-2 in hypocotyl cells of the 3-day-old seedling (FIG. 4F). To examine the relationship between the hypocotyl length and the ploidy level in ilp1-1 and ilp1-2, these mutants were analyzed at different stages of seedling development. ilp1-1 and ilp1-2 had shorter hypocotyls compared with the wild type at all stages of development in the dark (FIG. 4C). However, reduced ploidy levels of hypocotyl cells recovered to reach those of the wild type 7 days after imbibition. This indicates that a reduced ploidy level is not the consequence of a short hypocotyl length.

EXAMPLE 6

ILP1 Functions as a Transcriptional Repressor

It has been reported that the chimeric GCF, which was first identified, would function as a transcriptional repressor (Kageyama, R., and Pastan, I., 1989, Molecular cloning and characterization of a human DNA binding factor that represses transcription. Cell 59, 815-825). The N-terminal portion of this protein (GCF) has homology to GCF2 and has DNA binding activity (Reed, A. L., Yamazaki, H., Kaufman, J. D., Rubinstein, Y., Murphy, B., and Johnson, A. C., 1998, Molecular cloning and characterization of a transcription regulator with homology to GC-binding factor, J. Biol. Chem. 273, 21594-21602). ILP1 has homology to CTILP1s, but they have not been examined in detail in mammalian cells. To understand the function of ILP1, an in vivo transcriptional assay was performed (Yamamoto, Y. Y, and Deng, X. W., 1998, A new vector set for GAL4-dependent transactivation assay in plants, Plant Biotech. 15, 217-220). ILP1 cDNA was fused to the C-terminal region of the GAL4 DNA binding domain (GAL4-ILP1 Full). This chimeric plasmid was introduced into tobacco leaf cells by biolistic bombardment along with a luciferase (LUC) reporter plasmid containing the GAL4 binding sequence in the promoter region (FIG. 5A). The reporter plasmid was prepared from an *Escherichia coli* strain that lacked DNA methylase to ensure it was demethylated. When GAL4-ILP1 Full was used, reduction was observed in reporter activity (FIG. 5B). ILP1 has two conserved motifs. The part of the ILP1 protein that contains one of these motifs with a nuclear localization signal (NLS) was expressed. GAL4-ILP1N is a chimera containing the GAL4 DNA binding domain with the N-terminal region of ILP1 (residues 1 to 567) (FIG. 5A). This chimera contains motif 1 and NLS, and it did not show the strong repression as observed in the GAL4-ILP1Full protein (FIG. 5B). When the C-terminal region of ILP1 (residues 474 to 908) that contains motif 2 was used, however, much stronger repression of LUC reporter activity was observed (FIG. 5A and FIG. 5B). These results indicate that ILP1 functions as a transcriptional repressor in vivo and that motif 2 is responsible for this repressor activity.

EXAMPLE 7

Regulation of Cyclin A2 Expression by ILP1

Endoreduplication is a type of cell cycle, and switching to this cycle from a regular mitotic cell cycle may involve different cell-cycle-related genes. Thus, some cell-cycle-related genes that express at specific phases of the mitotic cell cycle were examined. CyclinD3;1 (CYCD3;1) was used as the G1-phase-specific gene (Riou-Khamlichi, C., Menges, M., Healy, J. M., and Murray, J. A. H., 2000, Sugar control of the plant cell cycle: differential regulation of *Arabidopsis* D-type cyclin gene expression, Mol. Cell. Biol. 20, 4513-4521); HistonH4 (HISH4) was used as the S phase-specific gene (Mariconti, L., Pellegrini, B., Cantoni, R., Stevens, R., Bergounioux, C., Cella, R., and Albani, D., 2002, The E2F family of transcription factors from *Arabidopsis thaliana*, Novel and conserved components of the retinoblastoma/E2F pathway in plants, J. Biol. Chem. 277, 9911-9919); CyclinA2;1 (CYCA2;1) was used as the S/G2 phase-specific gene; and CyclinB1;2 (CYCB1;2) was used as the G2/M phase-specific gene (Shaul, 0., Mironov, V., Burssens, S., Van Montagu, M., and Inze, D., 1996, Two *Arabidopsis* cyclin promoters mediate distinctive transcriptional oscillation in synchronized tobacco BY-2 cells, Proc. Natl. Acad. Sci. U.S.A., 93, 4868-4872). Expression of these genes was analyzed by semi-quantitative RT-PCR. An ILP1 overexpressing line (ILP1-ox, line #2, FIG. 3B) that showed the increased ploidy level was used, and expression of these cell cycle-related genes in dark-grown seedlings was examined.

There were no differences in expression of CYCD3;1, HISH4, and CYCB1;2 between the wild type (Col-0) and the ILP1 overexpressing line (ILPox) (FIG. 6A). However, expression of CYCA2;1 was significantly reduced in the ILP1 overexpressing line, compared with the wild type (FIG. 6A). CYCA2;1 is part of a gene family, and there are four CYCA2 members in the *Arabidopsis* genome (Vandepoele, K., Raes, J., De Veylder, L., Rouze, P., Rombauts, S., and Inze, D., 2002, Genome-wide analysis of core cell cycle genes in *Arabidopsis, Plant Cell* 14, 903-916). The expression of the CYCA2 genes in ILP1ox and ilp1-1D was inspected more precisely via real-time PCR. Reduced expression was observed in all the CYCA2 members (FIG. 6B, the upper panel). In particular, expression of CYCA2;1 in the ILP1ox line was reduced to approximately 40% of that of the wild type. Examination of expression of the CYCA2 genes in the ILP1 insertion mutants revealed that both ilp1-1 and ilp1-2 showed an increase in expression of substantially all members of the CYCA2 gene family (FIG. 6B, the lower panel).

Expression of ILP1 during leaf development was investigated. Expression was gradually reduced in accordance with development of the first leaf, and, 20 days after imbibition, it was reduced to one-tenth of the level at day 8 when the first leaves were in the proliferating phase (Vlieghe, K., Boudolf, V., Beemster, G. T., Maes, S., Magyar. Z., Atanassova, A., de Almeida Engler, J., De Groodt, R., Inzé, D., and De Veylder, L., 2005, The DP-E2F-like gene DELI controls the endocycle in *Arabidopsis thaliana, Curr. Biol.* 15, 59-63) (FIG. 6C). Also, expression of the CYCA2 gene family was investigated in comparison with the wild type during leaf development (FIG. 6D). All of the CYCA2 gene family exhibited high expression levels at day 8, and this was gradually reduced as in the case of ILP1 (data not shown) (Imai, K. K., Ohashi, Y., Tsuge, T., Yoshizumi, T., Matsui, M., Oka, A., and Aoyama, T., 2006, The A-Type Cyclin CYCA2;3 Is a Key Regulator of Ploidy Levels in *Arabidopsis* Endoreduplication, Plant Cell 18, 382-396). In ilp1-1D, expression of all of the CYCA2 gene family was reduced compared with the wild type (FIG. 6D, the upper panel). However, expression of all of the CYCA2 gene family was increased in ilp1-2 compared with the wild type, and relatively high expression was observed in CYCA2;3 and CYCA2;4 at day 12 (FIG. 6D, the lower panel). CYCA2;1 expression after day 12 was not detected in the wild type, ilp1-1D, or ilp1-2.

Observation of ploidy levels in leaves during cell division up to day 8 revealed that there were no apparent differences between wild-type and ilp1-1D. When compared with ilp1-2, however, reduction in the 2C fraction and an increase in the 8C and 16C fractions were observed. ilp1-1D gradually increased in the 8C and 16C fractions, compared with the wild type after day 10 (FIG. 6E). At day 22, the fraction of 16C cells was increased to 18% in ilp1-1D compared with 7% in the wild type (FIG. 6E). At day 8, the 2C fraction was 60% or more, and the 8C and 16C fractions were not detected in ilp1-2. However, the 8C and 16C fractions were increased in ilp1-2 as in the case of ilp1-1D after day 10 (FIG. 6E).

EXAMPLE 8

Regulation of Cyclin A2 Gene Expression in Mammalian Cells by Mouse ILP1

To understand whether or not the reduction of cyclin A2 expression is also observed in mammalian cells, a cotransfection assay was performed using NIH3T3 cells. cDNA of mouse ILP1 homolog (AAK68725) (FIG. 3E and FIG. 3F) was isolated by RT-PCR and cloned into an expression vector containing the Cytomegalovirus (CMV) promoter (FIG. 7A). This cDNA was cotransfected into NIH3T3 cells with a mouse cyclin A2 (Ccna2) promoter-LUC reporter by lipofection. A Ccna2 promoter containing −177 to +100 of the transcription initiation site was used (Huet, X., Rech, J., Plet, A., Vie, A., and Blanchard, J. M., 1996, Cyclin A expression is under negative transcriptional control during the cell cycle, Mol. Cell. Biol. 16, 3789-3798). This region shows conservation between mouse and human cyclin A2 promoters. As an internal standard for this assay, the β-galactosidase (LacZ) gene was used. As shown in FIG. 7B, reduction in reporter activity was observed in cells transfected with the mouse ILP1 gene both 24 hours and 48 hours after transfection.

EXAMPLE 9

Phenotype of T-DNA Insertion Mutants of CYCA2 Gene

Of the CYCA2 family, CYCA2;1 has been extensively studied, and the gene expression is reported to be specific to the S/G2-phase (Shaul, O., Mironov, V., Burssens, S., Van Montagu, M., and Inze, D., 1996, Two *Arabidopsis* cyclin promoters mediate distinctive transcriptional oscillation in synchronized tobacco BY-2 cells, Proc. Natl. Acad. Sci. U.S.A., 93, 4868-4872). To test whether or not reduction of CYCA2;1 expression is related to endoreduplication, the ploidy levels of CYCA2;1 T-DNA insertion mutants obtained from the SALK T-DNA collection were inspected (Alonso, J. M., Stepanova, A. N., Leisse, T. J., Kim, C. J., Chen, H., Shinn, P., Stevenson, D. K., Zimmerman, J., Barajas, P., Cheuk, R, et al., 2003, Genome-wide insertional mutagenesis of *Arabidopsis thaliana*, Science 301, 653-657). Two independent T-DNA insertion lines were examined. In insertion line 1 (cyca2; 1-1), the T-DNA was in the 1st exon (SALK__121077), and in insertion line 2 (cyca2; 1-2), it was in the 4th intron (SALK__136750) (FIG. 8A). RT-PCR analysis suggested these two lines were null (FIG. 8B). Both cyca2; 1-1 and cyca2; 1-2 homozygous lines showed almost no morphological differences compared with the wild type at the adult stage. Dark-grown seedling morphology was also the same as that of the wild type. When the ploidy levels in these T-DNA insertion lines were observed, an increased ratio of 32C cells was observed in dark-grown hypocotyls in the both lines, compared with the wild type (FIG. 8C). In the hypocotyls of light-grown seedlings, an increase in levels of 16C cells was observed (FIG. 8C). Ploidy levels in light-grown cotyledonal cells were also examined. Although the size of the cotyledons was not changed compared with the wild type, the 16C fraction was increased in both cyca2; 1-1 and cyca2; 1-2 (FIG. 8C). These data indicate that loss of CYCA2;1 expression induces an increase in ploidy.

EXAMPLE 10

Characterization of Other Mutants

Characteristics of Group 1 were observed in the other 5 mutants; i.e., ilp2-D, 3-D, 4-D, 5-D, and 7-D, and an increase in the DNA content was observed in the dark and in the light. These mutants, excluding ilp4-D, show phenotypes exhibiting enlarged cells, such as an increased cotyledonal area, an enlarged trichome, which is a hair having three branches on the surface of *Arabidopsis thaliana*, and an increased number of branches thereof, root elongation, and large hypocotyl diameters (FIGS. 9, 10, 12, and 13). In ILP2-, ILP5-, and ILP7-overexpressing transgenic plants, DNA contents are increased in the hypocotyls, and the phenotypes similar to those of the above mutants were observed (FIGS. 9, 12, and 13). Expression of ILP4 was stronger than that of ilp4-D in the ILP4-overexpressing transgenic plants (ILP4ox). In such transgenic plants, the cotyledonal area was increased (FIG. 11).

All publications, patents, and patent applications cited herein are incorporated herein by reference in their entirety.

Industrial Applicability

According to the present invention, a gene having activity of promoting endoreduplication and increasing a nuclear DNA content of a plant cell was discovered. The size of a plant body is determined by the number of cells constituting the plant body and the size thereof, and the plant cell becomes enlarged as the nuclear DNA content is increased. Accordingly, use of the gene of the present invention enables breeding of a plant with an increased size of a whole or part thereof. For example, it is known that endoreduplication takes place in tomato fruit. Thus, use of the gene of interest can result in improvement through breeding, such as production of larger tomatoes. Also, endosperm cells of cereal grains, such as rice or maize, are known to develop as the DNA content increases. Thus, the gene of interest may also be used to increase the endosperm size. If endoreduplication is accelerated with the use of the ILP gene, genes associated with material production can also be doubled. This can enhance the amount of production of various useful materials produced by plants (e.g., anthocyanin or flavonoids).

Mutants in which endoreduplication has been accelerated are known to become more tolerant to ultraviolet rays and the like (Hase Y, Trung K. H., Matsunaga T, Tanaka A, 2006, A mutation in the uvi4 gene promotes progression of endoreduplication and confers increased tolerance towards ultraviolet B light, Plant J. 46: 317-326). This is because DNA damage can be complemented by the increased number of genes per cell. As a secondary effect, the use of the ILP gene can result in breeding of crops that are tolerant to stresses that would cause DNA damages, such as ultraviolet rays.

The invention claimed is:

1. A transgenic plant with an increased nuclear DNA content in a plant cell into which an insolated nucleic acid has been introduced, wherein the isolated nucleic acid is:

(a) an isolated nucleic acid comprising SEQ ID NO: 1; or (b) an isolated nucleic acid comprising DNA which consists of a nucleotide sequence encoding SEQ ID NO:2.

2. The transgenic plant with an increased nuclear DNA content in a plant cell according to claim 1, wherein the plant is a plant body, a plant organ, a plant tissue, or a cultured plant cell.

3. A method for producing a transgenic plant, the method comprising:

introducing an isolated nucleic acid into a plant cell such that DNA content in the plant cell is increased; and reproducing a plant body from the plant cell, wherein the isolated nucleic acid is:

(a) an isolated nucleic acid comprising SEQ ID NO: 1; or (b) an isolated nucleic acid comprising DNA which consists of a nucleotide sequence encoding SEQ ID NO:2.

4. A transgenic plant with an increased nuclear DNA content in a plant cell into which an isolated nucleic acid has been introduced, wherein the isolated nucleic acid is:

an isolated nucleic acid encoding a protein consisting of the amino acid sequence of SEQ ID NO: 2.

5. The transgenic plant with an increased nuclear DNA content in a plant cell according to claim 4, wherein the plant is a plant body, a plant organ, a plant tissue, or a cultured plant cell.

6. A transgenic plant with an increased nuclear DNA content in a plant cell into which a recombinant vector has been introduced, wherein the recombinant vector comprises:

(a) an isolated nucleic acid comprising SEQ ID NO: 1; or (b) an isolated nucleic acid comprising DNA which consists of a nucleotide sequence encoding SEQ ID NO:2.

7. The transgenic plant with an increased nuclear DNA content in a plant cell according to claim 6, wherein the plant is a plant body, a plant organ, a plant tissue, or a cultured plant cell.

8. A method for producing a transgenic plant, the method comprising:

introducing an isolated nucleic acid into a plant cell such that DNA content in a plant cell is increased; and reproducing a plant body from the plant cell, wherein the isolated nucleic acid is:

an isolated nucleic acid encoding a protein consisting of the amino acid sequence of SEQ ID NO: 2.

9. A method for producing a transgenic plant, the method comprising:

introducing a recombinant vector into a plant cell such that DNA content in a plant cell is increased; and reproducing a plant body from the plant cell, wherein the recombinant vector comprises:

(a) an isolated nucleic acid comprising SEQ ID NO: 1; or (b) an isolated nucleic acid comprising DNA which consists of a nucleotide sequence encoding SEQ ID NO:2.

* * * * *

SEQUENCE LISTING

```
<160> NUMBER OF SEQ ID NOS: 61

<210> SEQ ID NO 1
<211> LENGTH: 3066
<212> TYPE: DNA
<213> ORGANISM: Arabidopsis thaliana
<220> FEATURE:
<221> NAME/KEY: CDS
<222> LOCATION: (1)..(2724)

<400> SEQUENCE: 1

atg gga agt aac cgt cct aag aat ttc cgg cgg cga ggg gac gac ggc       48
Met Gly Ser Asn Arg Pro Lys Asn Phe Arg Arg Arg Gly Asp Asp Gly
1               5                   10                  15

ggc gat gaa att gac ggt aaa gtt gct acc ccc tcg tca aaa ccg act       96
Gly Asp Glu Ile Asp Gly Lys Val Ala Thr Pro Ser Ser Lys Pro Thr
            20                  25                  30

tcg act ctt tcc tcc tcg aaa cct aaa aca ctc tca gcc tcg gcc ccg      144
Ser Thr Leu Ser Ser Ser Lys Pro Lys Thr Leu Ser Ala Ser Ala Pro
        35                  40                  45

aag aag aaa ctc cta agt ttc gcc gac gac gag gag gag gaa gaa gat      192
Lys Lys Lys Leu Leu Ser Phe Ala Asp Asp Glu Glu Glu Glu Glu Asp
    50                  55                  60

gga gct ccc cgt gtg acg ata aag cct aag aac ggc aga gac cgt gtc      240
Gly Ala Pro Arg Val Thr Ile Lys Pro Lys Asn Gly Arg Asp Arg Val
65                  70                  75                  80

aaa tcc tct tcc cgt ctc ggc gtt tcg gga tct tct cac aga cac tct      288
Lys Ser Ser Ser Arg Leu Gly Val Ser Gly Ser Ser His Arg His Ser
                85                  90                  95

tca acc aag gaa cgt cgt ccc gct tct tct aac gtg ctt cct cag gcc      336
Ser Thr Lys Glu Arg Arg Pro Ala Ser Ser Asn Val Leu Pro Gln Ala
            100                 105                 110

ggc tct tat tcg aaa gag gcg ctg ctc gag ctc cag aag aac aca cgg      384
Gly Ser Tyr Ser Lys Glu Ala Leu Leu Glu Leu Gln Lys Asn Thr Arg
        115                 120                 125
```

-continued

```
acg ctt cct tat tct cgc tct agt gcc aat gcc gag ccg aag gta gtg      432
Thr Leu Pro Tyr Ser Arg Ser Ser Ala Asn Ala Glu Pro Lys Val Val
    130                 135                 140

ctt aag ggt tta atc aaa cct ccg cag gat cat gag cag cag agt ctg      480
Leu Lys Gly Leu Ile Lys Pro Pro Gln Asp His Glu Gln Gln Ser Leu
145                 150                 155                 160

aag gat gta gtt aaa cag gtt tcg gat ttg gac ttc gat gag gaa ggg      528
Lys Asp Val Val Lys Gln Val Ser Asp Leu Asp Phe Asp Glu Glu Gly
                165                 170                 175

gaa gaa gag cag cat gaa gat gcg ttt gct gat cag gca gcg att att      576
Glu Glu Glu Gln His Glu Asp Ala Phe Ala Asp Gln Ala Ala Ile Ile
            180                 185                 190

aga gcc aag aaa gag agg atg agg cag tca cgt tca gca ccg gcg cct      624
Arg Ala Lys Lys Glu Arg Met Arg Gln Ser Arg Ser Ala Pro Ala Pro
        195                 200                 205

gat tac ata tca cta gat ggt ggt atc gta aat cat tct gct gtt gaa      672
Asp Tyr Ile Ser Leu Asp Gly Gly Ile Val Asn His Ser Ala Val Glu
    210                 215                 220

gga gtc agc gac gag gat gcg gat ttt cag gga att ttc gtc ggt ccg      720
Gly Val Ser Asp Glu Asp Ala Asp Phe Gln Gly Ile Phe Val Gly Pro
225                 230                 235                 240

aga cct cag aaa gat gat aag aaa ggt gtg ttt gat ttc ggt gat gaa      768
Arg Pro Gln Lys Asp Asp Lys Lys Gly Val Phe Asp Phe Gly Asp Glu
                245                 250                 255

aat cct act gct aaa gaa acc acg aca agt agt att tat gag gat gag      816
Asn Pro Thr Ala Lys Glu Thr Thr Thr Ser Ser Ile Tyr Glu Asp Glu
            260                 265                 270

gat gaa gaa gat aag ttg tgg gag gag gag caa ttt aag aag ggt att      864
Asp Glu Glu Asp Lys Leu Trp Glu Glu Glu Gln Phe Lys Lys Gly Ile
        275                 280                 285

ggt aaa aga atg gac gaa ggg tcg cat agg act gta act agt aat ggg      912
Gly Lys Arg Met Asp Glu Gly Ser His Arg Thr Val Thr Ser Asn Gly
    290                 295                 300

att ggc gtg cct ttg cat tct aaa cag cag aca ctg cca caa cag caa      960
Ile Gly Val Pro Leu His Ser Lys Gln Gln Thr Leu Pro Gln Gln Gln
305                 310                 315                 320

ccg cag atg tat gct tat cat gcc ggg aca cca atg ccg aat gtt tct     1008
Pro Gln Met Tyr Ala Tyr His Ala Gly Thr Pro Met Pro Asn Val Ser
                325                 330                 335

gtc gct cct acc att ggc cca gct act agt gtt gat aca tta cca atg     1056
Val Ala Pro Thr Ile Gly Pro Ala Thr Ser Val Asp Thr Leu Pro Met
            340                 345                 350

tca caa caa gcc gag ctt gcc aag aag gca ttg aaa gac aat gtt aag     1104
Ser Gln Gln Ala Glu Leu Ala Lys Lys Ala Leu Lys Asp Asn Val Lys
        355                 360                 365

aag ctt aag gaa tct cat gca aaa acg tta tcc tcc ctt acc aag aca     1152
Lys Leu Lys Glu Ser His Ala Lys Thr Leu Ser Ser Leu Thr Lys Thr
    370                 375                 380

gat gag aat ctg act gcg tcg ttg atg agt atc aca gct ctt gaa agt     1200
Asp Glu Asn Leu Thr Ala Ser Leu Met Ser Ile Thr Ala Leu Glu Ser
385                 390                 395                 400

tcg cta tct gca gct gga gat aag tat gtg ttc atg caa aaa ctc aga     1248
Ser Leu Ser Ala Ala Gly Asp Lys Tyr Val Phe Met Gln Lys Leu Arg
                405                 410                 415

gac ttc att tct gtt atc tgt gac ttc atg cag aat aag ggt tca tta     1296
Asp Phe Ile Ser Val Ile Cys Asp Phe Met Gln Asn Lys Gly Ser Leu
            420                 425                 430

att gaa gaa att gaa gat caa atg aag gaa ctt aac gaa aaa cat gct     1344
Ile Glu Glu Ile Glu Asp Gln Met Lys Glu Leu Asn Glu Lys His Ala
        435                 440                 445
```

```
tta tct att cta gaa agg aga att gca gat aac aat gat gaa atg ata      1392
Leu Ser Ile Leu Glu Arg Arg Ile Ala Asp Asn Asn Asp Glu Met Ile
    450                 455                 460

gag ttg ggg gcc gca gtg aaa gca gca atg aca gtt cta aac aaa cat      1440
Glu Leu Gly Ala Ala Val Lys Ala Ala Met Thr Val Leu Asn Lys His
465                 470                 475                 480

gga agc agt agt tca gtg att gct gct gcc aca ggt gct gcg ttg gct      1488
Gly Ser Ser Ser Ser Val Ile Ala Ala Ala Thr Gly Ala Ala Leu Ala
                485                 490                 495

gcc tct act tct ata agg cag cag atg aat caa cca gtt aag ctt gat      1536
Ala Ser Thr Ser Ile Arg Gln Gln Met Asn Gln Pro Val Lys Leu Asp
            500                 505                 510

gaa ttt ggc aga gac gaa aat ctg cag aag cgc agg gaa gtg gaa cag      1584
Glu Phe Gly Arg Asp Glu Asn Leu Gln Lys Arg Arg Glu Val Glu Gln
        515                 520                 525

agg gct gca gcc cgg cag aaa agg cga gct cga ttt gaa aat aag cgt      1632
Arg Ala Ala Ala Arg Gln Lys Arg Arg Ala Arg Phe Glu Asn Lys Arg
    530                 535                 540

gca tca gct atg gag gtt gat gga cct tct ctg aaa ata gaa gga gaa      1680
Ala Ser Ala Met Glu Val Asp Gly Pro Ser Leu Lys Ile Glu Gly Glu
545                 550                 555                 560

tca agc act gat gag agt gac act gag act tca gct tat aag gag aca      1728
Ser Ser Thr Asp Glu Ser Asp Thr Glu Thr Ser Ala Tyr Lys Glu Thr
                565                 570                 575

aga gat agc tta ctt cag tgt gct gat aag gtc ttt agt gat gca tct      1776
Arg Asp Ser Leu Leu Gln Cys Ala Asp Lys Val Phe Ser Asp Ala Ser
            580                 585                 590

gag gag tac tcc cag ctt tca aag gtg aag gcg aga ttt gag agg tgg      1824
Glu Glu Tyr Ser Gln Leu Ser Lys Val Lys Ala Arg Phe Glu Arg Trp
        595                 600                 605

aag cga gac tat tca tca act tat cgt gat gct tac atg tct ttg acc      1872
Lys Arg Asp Tyr Ser Ser Thr Tyr Arg Asp Ala Tyr Met Ser Leu Thr
    610                 615                 620

gtt cct tcc atc ttt tca cct tat gta aga ctg gag ctt ttg aaa tgg      1920
Val Pro Ser Ile Phe Ser Pro Tyr Val Arg Leu Glu Leu Leu Lys Trp
625                 630                 635                 640

gat cct ctt cat caa gat gtg gat ttc ttt gac atg aaa tgg cat ggg      1968
Asp Pro Leu His Gln Asp Val Asp Phe Phe Asp Met Lys Trp His Gly
                645                 650                 655

ttg ctt ttt gat tac ggg aag cca gaa gat ggg gat gat ttt gca cca      2016
Leu Leu Phe Asp Tyr Gly Lys Pro Glu Asp Gly Asp Asp Phe Ala Pro
            660                 665                 670

gat gat act gat gcc aac ctt gtc cct gag cta gta gaa aag gtt gca      2064
Asp Asp Thr Asp Ala Asn Leu Val Pro Glu Leu Val Glu Lys Val Ala
        675                 680                 685

att cca att ttg cac cat cag ata gtt cgt tgc tgg gat ata ctt agc      2112
Ile Pro Ile Leu His His Gln Ile Val Arg Cys Trp Asp Ile Leu Ser
    690                 695                 700

acc cgg gag aca aga aat gct gtt gct gct aca agc ttg gtg aca aat      2160
Thr Arg Glu Thr Arg Asn Ala Val Ala Ala Thr Ser Leu Val Thr Asn
705                 710                 715                 720

tat gtt tct gct tcg agt gag gcc tta gca gaa cta ttt gct gct att      2208
Tyr Val Ser Ala Ser Ser Glu Ala Leu Ala Glu Leu Phe Ala Ala Ile
                725                 730                 735

cgt gct cgc ctt gtt gaa gcc att gca gct att agt gtt ccg aca tgg      2256
Arg Ala Arg Leu Val Glu Ala Ile Ala Ala Ile Ser Val Pro Thr Trp
            740                 745                 750

gat cct ctg gta ttg aag gct gta cct aat act cca caa gtt gcc gca      2304
Asp Pro Leu Val Leu Lys Ala Val Pro Asn Thr Pro Gln Val Ala Ala
        755                 760                 765
```

-continued

```
tat agg ttt ggg aca tca gtc cgt ctt atg aga aat ata tgt atg tgg     2352
Tyr Arg Phe Gly Thr Ser Val Arg Leu Met Arg Asn Ile Cys Met Trp
    770                 775                 780

aaa gac atc ctg gcg ctt cca gtg ttg gag aac ttg gct ctt agt gac     2400
Lys Asp Ile Leu Ala Leu Pro Val Leu Glu Asn Leu Ala Leu Ser Asp
785                 790                 795                 800

ctt ttg ttt gga aaa gtt cta ccc cat gtc aga agc att gca tca aat     2448
Leu Leu Phe Gly Lys Val Leu Pro His Val Arg Ser Ile Ala Ser Asn
                805                 810                 815

atc cat gat gct gtg aca aga act gaa aga atc gtt gct tct ttg tct     2496
Ile His Asp Ala Val Thr Arg Thr Glu Arg Ile Val Ala Ser Leu Ser
            820                 825                 830

gga gtg tgg aca gga cca agc gtc aca cga acc cac agt cgt ccg ctg     2544
Gly Val Trp Thr Gly Pro Ser Val Thr Arg Thr His Ser Arg Pro Leu
        835                 840                 845

caa cct ctt gtg gat tgt act ctg aca ctt aga aga att ctc gag aaa     2592
Gln Pro Leu Val Asp Cys Thr Leu Thr Leu Arg Arg Ile Leu Glu Lys
    850                 855                 860

agg ctt ggc tca gga ctg gac gat gcg gaa acc act ggt ctc gcc cgc     2640
Arg Leu Gly Ser Gly Leu Asp Asp Ala Glu Thr Thr Gly Leu Ala Arg
865                 870                 875                 880

aga tta aag aga ata cta gtc gag ctc cat gaa cat gac cac gcc agg     2688
Arg Leu Lys Arg Ile Leu Val Glu Leu His Glu His Asp His Ala Arg
                885                 890                 895

gaa att gtc aga aca ttc aat ctt aag gag gca gtt tgaccaaaag          2734
Glu Ile Val Arg Thr Phe Asn Leu Lys Glu Ala Val
            900                 905

tttattgatg ggaaactgga aagtcaacac agaaatcttt agcctcaggt tatcaggctc   2794

acctttcggg ctgtaccagc aaaggctcat cgatttcaac atcgaggatt acaagatttt   2854

ccctaggatt attaggctag caccaaaacc ttccggaatc cattttcaga cacagaagag   2914

ttttagtact ttggcttaat gtaagtgtaa cctcttgtgg ttgtagaaaa ccttataata   2974

aatataagct aaagtatctc gagtctttta tttttccctt tatatctgta tgagtttaga   3034

tttagcaaag acaatattat ttctatgaat at                                 3066


<210> SEQ ID NO 2
<211> LENGTH: 908
<212> TYPE: PRT
<213> ORGANISM: Arabidopsis thaliana

<400> SEQUENCE: 2

Met Gly Ser Asn Arg Pro Lys Asn Phe Arg Arg Arg Gly Asp Asp Gly
1               5                   10                  15

Gly Asp Glu Ile Asp Gly Lys Val Ala Thr Pro Ser Ser Lys Pro Thr
            20                  25                  30

Ser Thr Leu Ser Ser Ser Lys Pro Lys Thr Leu Ser Ala Ser Ala Pro
        35                  40                  45

Lys Lys Lys Leu Leu Ser Phe Ala Asp Asp Glu Glu Glu Glu Glu Asp
    50                  55                  60

Gly Ala Pro Arg Val Thr Ile Lys Pro Lys Asn Gly Arg Asp Arg Val
65                  70                  75                  80

Lys Ser Ser Ser Arg Leu Gly Val Ser Gly Ser Ser His Arg His Ser
                85                  90                  95

Ser Thr Lys Glu Arg Arg Pro Ala Ser Ser Asn Val Leu Pro Gln Ala
            100                 105                 110

Gly Ser Tyr Ser Lys Glu Ala Leu Leu Glu Leu Gln Lys Asn Thr Arg
        115                 120                 125
```

-continued

```
Thr Leu Pro Tyr Ser Arg Ser Ser Ala Asn Ala Glu Pro Lys Val Val
    130                 135                 140

Leu Lys Gly Leu Ile Lys Pro Pro Gln Asp His Glu Gln Gln Ser Leu
145                 150                 155                 160

Lys Asp Val Val Lys Gln Val Ser Asp Leu Asp Phe Asp Glu Glu Gly
                165                 170                 175

Glu Glu Glu Gln His Glu Asp Ala Phe Ala Asp Gln Ala Ala Ile Ile
            180                 185                 190

Arg Ala Lys Lys Glu Arg Met Arg Gln Ser Arg Ser Ala Pro Ala Pro
        195                 200                 205

Asp Tyr Ile Ser Leu Asp Gly Gly Ile Val Asn His Ser Ala Val Glu
    210                 215                 220

Gly Val Ser Asp Glu Asp Ala Asp Phe Gln Gly Ile Phe Val Gly Pro
225                 230                 235                 240

Arg Pro Gln Lys Asp Asp Lys Lys Gly Val Phe Asp Phe Gly Asp Glu
                245                 250                 255

Asn Pro Thr Ala Lys Glu Thr Thr Thr Ser Ser Ile Tyr Glu Asp Glu
            260                 265                 270

Asp Glu Glu Asp Lys Leu Trp Glu Glu Glu Gln Phe Lys Lys Gly Ile
        275                 280                 285

Gly Lys Arg Met Asp Glu Gly Ser His Arg Thr Val Thr Ser Asn Gly
    290                 295                 300

Ile Gly Val Pro Leu His Ser Lys Gln Gln Thr Leu Pro Gln Gln Gln
305                 310                 315                 320

Pro Gln Met Tyr Ala Tyr His Ala Gly Thr Pro Met Pro Asn Val Ser
                325                 330                 335

Val Ala Pro Thr Ile Gly Pro Ala Thr Ser Val Asp Thr Leu Pro Met
            340                 345                 350

Ser Gln Gln Ala Glu Leu Ala Lys Lys Ala Leu Lys Asp Asn Val Lys
        355                 360                 365

Lys Leu Lys Glu Ser His Ala Lys Thr Leu Ser Ser Leu Thr Lys Thr
    370                 375                 380

Asp Glu Asn Leu Thr Ala Ser Leu Met Ser Ile Thr Ala Leu Glu Ser
385                 390                 395                 400

Ser Leu Ser Ala Ala Gly Asp Lys Tyr Val Phe Met Gln Lys Leu Arg
                405                 410                 415

Asp Phe Ile Ser Val Ile Cys Asp Phe Met Gln Asn Lys Gly Ser Leu
            420                 425                 430

Ile Glu Glu Ile Glu Asp Gln Met Lys Glu Leu Asn Glu Lys His Ala
        435                 440                 445

Leu Ser Ile Leu Glu Arg Arg Ile Ala Asp Asn Asn Asp Glu Met Ile
    450                 455                 460

Glu Leu Gly Ala Ala Val Lys Ala Ala Met Thr Val Leu Asn Lys His
465                 470                 475                 480

Gly Ser Ser Ser Ser Val Ile Ala Ala Ala Thr Gly Ala Ala Leu Ala
                485                 490                 495

Ala Ser Thr Ser Ile Arg Gln Gln Met Asn Gln Pro Val Lys Leu Asp
            500                 505                 510

Glu Phe Gly Arg Asp Glu Asn Leu Gln Lys Arg Arg Glu Val Glu Gln
        515                 520                 525

Arg Ala Ala Ala Arg Gln Lys Arg Arg Ala Arg Phe Glu Asn Lys Arg
    530                 535                 540

Ala Ser Ala Met Glu Val Asp Gly Pro Ser Leu Lys Ile Glu Gly Glu
545                 550                 555                 560
```

```
Ser Ser Thr Asp Glu Ser Asp Thr Glu Thr Ser Ala Tyr Lys Glu Thr
                565                 570                 575

Arg Asp Ser Leu Leu Gln Cys Ala Asp Lys Val Phe Ser Asp Ala Ser
            580                 585                 590

Glu Glu Tyr Ser Gln Leu Ser Lys Val Lys Ala Arg Phe Glu Arg Trp
        595                 600                 605

Lys Arg Asp Tyr Ser Ser Thr Tyr Arg Asp Ala Tyr Met Ser Leu Thr
    610                 615                 620

Val Pro Ser Ile Phe Ser Pro Tyr Val Arg Leu Glu Leu Leu Lys Trp
625                 630                 635                 640

Asp Pro Leu His Gln Asp Val Asp Phe Phe Asp Met Lys Trp His Gly
                645                 650                 655

Leu Leu Phe Asp Tyr Gly Lys Pro Glu Asp Gly Asp Asp Phe Ala Pro
            660                 665                 670

Asp Asp Thr Asp Ala Asn Leu Val Pro Glu Leu Val Glu Lys Val Ala
        675                 680                 685

Ile Pro Ile Leu His His Gln Ile Val Arg Cys Trp Asp Ile Leu Ser
    690                 695                 700

Thr Arg Glu Thr Arg Asn Ala Val Ala Ala Thr Ser Leu Val Thr Asn
705                 710                 715                 720

Tyr Val Ser Ala Ser Ser Glu Ala Leu Ala Glu Leu Phe Ala Ala Ile
                725                 730                 735

Arg Ala Arg Leu Val Glu Ala Ile Ala Ala Ile Ser Val Pro Thr Trp
            740                 745                 750

Asp Pro Leu Val Leu Lys Ala Val Pro Asn Thr Pro Gln Val Ala Ala
        755                 760                 765

Tyr Arg Phe Gly Thr Ser Val Arg Leu Met Arg Asn Ile Cys Met Trp
    770                 775                 780

Lys Asp Ile Leu Ala Leu Pro Val Leu Glu Asn Leu Ala Leu Ser Asp
785                 790                 795                 800

Leu Leu Phe Gly Lys Val Leu Pro His Val Arg Ser Ile Ala Ser Asn
                805                 810                 815

Ile His Asp Ala Val Thr Arg Thr Glu Arg Ile Val Ala Ser Leu Ser
            820                 825                 830

Gly Val Trp Thr Gly Pro Ser Val Thr Arg Thr His Ser Arg Pro Leu
        835                 840                 845

Gln Pro Leu Val Asp Cys Thr Leu Thr Leu Arg Arg Ile Leu Glu Lys
    850                 855                 860

Arg Leu Gly Ser Gly Leu Asp Asp Ala Glu Thr Thr Gly Leu Ala Arg
865                 870                 875                 880

Arg Leu Lys Arg Ile Leu Val Glu Leu His Glu His Asp His Ala Arg
                885                 890                 895

Glu Ile Val Arg Thr Phe Asn Leu Lys Glu Ala Val
            900                 905
```

<210> SEQ ID NO 3
<211> LENGTH: 1328
<212> TYPE: DNA
<213> ORGANISM: Arabidopsis thaliana
<220> FEATURE:
<221> NAME/KEY: CDS
<222> LOCATION: (66)..(1037)

<400> SEQUENCE: 3

```
aggttcatac ttactgaaaa aaacagagga aaaaaaggag ctccctttc tatctctaag     60
```

-continued

```
ggaaa atg ggt agc aag atg ttg ttt agt ttg aca agt cct cga ctt ttc     110
      Met Gly Ser Lys Met Leu Phe Ser Leu Thr Ser Pro Arg Leu Phe
      1               5                  10                  15

tcc gcc gtt tct cgc aaa cct tcc tct tct ttc tct cct tct cct ccg     158
Ser Ala Val Ser Arg Lys Pro Ser Ser Ser Phe Ser Pro Ser Pro Pro
                20                  25                  30

tcg ccg tct tcg agg act caa tgg act cag ctc agc cct gga aaa tcg     206
Ser Pro Ser Ser Arg Thr Gln Trp Thr Gln Leu Ser Pro Gly Lys Ser
            35                  40                  45

att tct ttg aga aga aga gtc ttc ttg ttg cct gct aaa gcc aca aca     254
Ile Ser Leu Arg Arg Arg Val Phe Leu Leu Pro Ala Lys Ala Thr Thr
        50                  55                  60

gag caa tca ggt cca gta gga gga gac aac gtc gat agc aat gtt ttg     302
Glu Gln Ser Gly Pro Val Gly Gly Asp Asn Val Asp Ser Asn Val Leu
    65                  70                  75

ccc tat tgt agc atc aac aag gct gag aag aaa aca att ggt gaa atg     350
Pro Tyr Cys Ser Ile Asn Lys Ala Glu Lys Lys Thr Ile Gly Glu Met
80                  85                  90                  95

gaa caa gag ttt ctc caa gcg ttg caa tct ttc tat tat gat ggc aaa     398
Glu Gln Glu Phe Leu Gln Ala Leu Gln Ser Phe Tyr Tyr Asp Gly Lys
                100                 105                 110

gcg atc atg tct aat gaa gat ttt gat aac ctt aaa gaa gag tta atg     446
Ala Ile Met Ser Asn Glu Asp Phe Asp Asn Leu Lys Glu Glu Leu Met
            115                 120                 125

tgg gaa gga agc agt gtt gtg atg cta agt tcc gat gaa caa aga ttc     494
Trp Glu Gly Ser Ser Val Val Met Leu Ser Ser Asp Glu Gln Arg Phe
        130                 135                 140

ttg gaa gct tcc atg gct tat gtt tct gga aat cca atc ttg aat gat     542
Leu Glu Ala Ser Met Ala Tyr Val Ser Gly Asn Pro Ile Leu Asn Asp
    145                 150                 155

gaa gaa tat gat aag ctc aaa ctc aaa cta aag att gat ggt agc gac     590
Glu Glu Tyr Asp Lys Leu Lys Leu Lys Leu Lys Ile Asp Gly Ser Asp
160                 165                 170                 175

att gtg agc gag ggt cca aga tgc agt ctc cgt agt aaa aag gtg tat     638
Ile Val Ser Glu Gly Pro Arg Cys Ser Leu Arg Ser Lys Lys Val Tyr
                180                 185                 190

agt gat ctc gct gta gat tat ttc aaa atg tta ttg ttg aat gtt cca     686
Ser Asp Leu Ala Val Asp Tyr Phe Lys Met Leu Leu Leu Asn Val Pro
            195                 200                 205

gca acc gtt gtt gct ctc gga ctc ttt ttc ttc ctg gac gac att aca     734
Ala Thr Val Val Ala Leu Gly Leu Phe Phe Phe Leu Asp Asp Ile Thr
        210                 215                 220

ggt ttt gag atc aca tac atc atg gag ctt cca gaa cca tac agt ttc     782
Gly Phe Glu Ile Thr Tyr Ile Met Glu Leu Pro Glu Pro Tyr Ser Phe
    225                 230                 235

ata ttc act tgg ttc gct gct gtg cct gtg att gta tat ctg gct tta     830
Ile Phe Thr Trp Phe Ala Ala Val Pro Val Ile Val Tyr Leu Ala Leu
240                 245                 250                 255

tca atc acc aaa ttg atc atc aag gac ttc ttg atc ttg aag ggt cct     878
Ser Ile Thr Lys Leu Ile Ile Lys Asp Phe Leu Ile Leu Lys Gly Pro
                260                 265                 270

tgt ccg aat tgt gga acg gaa aac acc tcc ttc ttt gga aca att ctg     926
Cys Pro Asn Cys Gly Thr Glu Asn Thr Ser Phe Phe Gly Thr Ile Leu
            275                 280                 285

tca atc tcc agc ggc ggc aaa acc aac act gtc aaa tgc acc aac tgc     974
Ser Ile Ser Ser Gly Gly Lys Thr Asn Thr Val Lys Cys Thr Asn Cys
        290                 295                 300

gga acc gcg atg gtg tat gac tcg ggt tct agg ttg atc aca ttg cca    1022
Gly Thr Ala Met Val Tyr Asp Ser Gly Ser Arg Leu Ile Thr Leu Pro
    305                 310                 315
```

-continued

```
gaa gga agc caa gct taaaccctgt gagctagatg aagatgggaa aagaagaatg     1077
Glu Gly Ser Gln Ala
320

ggttttgtca gaagcaaaat agattcgaag ttaaatgtat atgtaagatc ttccatgtta   1137

gctctctctc cttcacatgt tttctgattt gtaagtattg tgtgtaagca ataagagata   1197

tataatatga gcacttcttc atctaccttt gtagataaaa atataatcat tactatagtt   1257

aaatcaaatt gtatacatga aagaccaaat tcgaatttaa aatgtttatt tcgacaaaaa   1317

aaaaaaaaaa a                                                         1328


<210> SEQ ID NO 4
<211> LENGTH: 324
<212> TYPE: PRT
<213> ORGANISM: Arabidopsis thaliana

<400> SEQUENCE: 4

Met Gly Ser Lys Met Leu Phe Ser Leu Thr Ser Pro Arg Leu Phe Ser
1               5                   10                  15

Ala Val Ser Arg Lys Pro Ser Ser Ser Phe Ser Pro Ser Pro Pro Ser
            20                  25                  30

Pro Ser Ser Arg Thr Gln Trp Thr Gln Leu Ser Pro Gly Lys Ser Ile
        35                  40                  45

Ser Leu Arg Arg Arg Val Phe Leu Leu Pro Ala Lys Ala Thr Thr Glu
    50                  55                  60

Gln Ser Gly Pro Val Gly Gly Asp Asn Val Asp Ser Asn Val Leu Pro
65                  70                  75                  80

Tyr Cys Ser Ile Asn Lys Ala Glu Lys Lys Thr Ile Gly Glu Met Glu
                85                  90                  95

Gln Glu Phe Leu Gln Ala Leu Gln Ser Phe Tyr Tyr Asp Gly Lys Ala
            100                 105                 110

Ile Met Ser Asn Glu Asp Phe Asp Asn Leu Lys Glu Glu Leu Met Trp
        115                 120                 125

Glu Gly Ser Ser Val Val Met Leu Ser Ser Asp Glu Gln Arg Phe Leu
    130                 135                 140

Glu Ala Ser Met Ala Tyr Val Ser Gly Asn Pro Ile Leu Asn Asp Glu
145                 150                 155                 160

Glu Tyr Asp Lys Leu Lys Leu Lys Leu Lys Ile Asp Gly Ser Asp Ile
                165                 170                 175

Val Ser Glu Gly Pro Arg Cys Ser Leu Arg Ser Lys Lys Val Tyr Ser
            180                 185                 190

Asp Leu Ala Val Asp Tyr Phe Lys Met Leu Leu Leu Asn Val Pro Ala
        195                 200                 205

Thr Val Val Ala Leu Gly Leu Phe Phe Phe Leu Asp Asp Ile Thr Gly
    210                 215                 220

Phe Glu Ile Thr Tyr Ile Met Glu Leu Pro Glu Pro Tyr Ser Phe Ile
225                 230                 235                 240

Phe Thr Trp Phe Ala Ala Val Pro Val Ile Val Tyr Leu Ala Leu Ser
                245                 250                 255

Ile Thr Lys Leu Ile Ile Lys Asp Phe Leu Ile Leu Lys Gly Pro Cys
            260                 265                 270

Pro Asn Cys Gly Thr Glu Asn Thr Ser Phe Phe Gly Thr Ile Leu Ser
        275                 280                 285

Ile Ser Ser Gly Gly Lys Thr Asn Thr Val Lys Cys Thr Asn Cys Gly
    290                 295                 300

Thr Ala Met Val Tyr Asp Ser Gly Ser Arg Leu Ile Thr Leu Pro Glu
```

```
305                 310                 315                 320

Gly Ser Gln Ala


<210> SEQ ID NO 5
<211> LENGTH: 1119
<212> TYPE: DNA
<213> ORGANISM: Arabidopsis thaliana
<220> FEATURE:
<221> NAME/KEY: CDS
<222> LOCATION: (19)..(1095)

<400> SEQUENCE: 5

acccacccca cccaggtt atg gat tct ctc gct ctc gct ccc cag gtt tac        51
                    Met Asp Ser Leu Ala Leu Ala Pro Gln Val Tyr
                    1               5                   10

agc cgc aag gac aaa tct ctc ggc gtt ctt gtc gcc aat ttc ttg aca        99
Ser Arg Lys Asp Lys Ser Leu Gly Val Leu Val Ala Asn Phe Leu Thr
            15                  20                  25

ctg tat aat cgt ccc gat gtt gat cta ttt ggg ctc gat gat gcc gcc       147
Leu Tyr Asn Arg Pro Asp Val Asp Leu Phe Gly Leu Asp Asp Ala Ala
        30                  35                  40

gcg aaa tta gga gtt gaa cgt cgg cgt att tat gat gtg gtc aat ata       195
Ala Lys Leu Gly Val Glu Arg Arg Arg Ile Tyr Asp Val Val Asn Ile
    45                  50                  55

ttg gag agt att ggg ctt gtt gca aga agt ggg aag aat cag tat tcg       243
Leu Glu Ser Ile Gly Leu Val Ala Arg Ser Gly Lys Asn Gln Tyr Ser
60                  65                  70                  75

tgg aaa ggt ttt gga gct gtt cct cgt gct cta tct gaa ctc aaa gaa       291
Trp Lys Gly Phe Gly Ala Val Pro Arg Ala Leu Ser Glu Leu Lys Glu
                80                  85                  90

gag gga atg aaa gag aag ttt gcg atc gtc cct ttt gtg gcc aag tca       339
Glu Gly Met Lys Glu Lys Phe Ala Ile Val Pro Phe Val Ala Lys Ser
            95                  100                 105

gag atg gtc gtt tat gag aaa gaa gga gaa gaa tct ttc atg tta tct       387
Glu Met Val Val Tyr Glu Lys Glu Gly Glu Glu Ser Phe Met Leu Ser
        110                 115                 120

cct gat gat caa gag ttc tca cca tct ccc aga cct gac aac agg aag       435
Pro Asp Asp Gln Glu Phe Ser Pro Ser Pro Arg Pro Asp Asn Arg Lys
    125                 130                 135

gag aga act ctc tgg cta ctt gca cag aac ttt gtg aag ctg ttt tta       483
Glu Arg Thr Leu Trp Leu Leu Ala Gln Asn Phe Val Lys Leu Phe Leu
140                 145                 150                 155

tgc tct gat gat gat ctg gta aca ttt gat agc gct aca aaa gca ttg       531
Cys Ser Asp Asp Asp Leu Val Thr Phe Asp Ser Ala Thr Lys Ala Leu
                160                 165                 170

ctg aat gag tct cag gat atg aat atg aga aag aaa gtt aga cgc ctt       579
Leu Asn Glu Ser Gln Asp Met Asn Met Arg Lys Lys Val Arg Arg Leu
            175                 180                 185

tac gac att gca aat gtg ttt tcc tca atg aag cta atc gag aag act       627
Tyr Asp Ile Ala Asn Val Phe Ser Ser Met Lys Leu Ile Glu Lys Thr
        190                 195                 200

cat gtc cca gag act aag aag ccg gca tat agg tgg ttg gga tct aaa       675
His Val Pro Glu Thr Lys Lys Pro Ala Tyr Arg Trp Leu Gly Ser Lys
    205                 210                 215

acc ata ttt gaa aac aga ttc att gat ggt tct gca agc tta tgt gat       723
Thr Ile Phe Glu Asn Arg Phe Ile Asp Gly Ser Ala Ser Leu Cys Asp
220                 225                 230                 235

cgt aat gtg cct aaa aag cgg gca ttt ggg acc gaa ctc aca aac gtt       771
Arg Asn Val Pro Lys Lys Arg Ala Phe Gly Thr Glu Leu Thr Asn Val
                240                 245                 250

aac gca aag aga aac aaa tca ggt tgt tct aaa gaa gac agc aag cgt       819
```

```
Asn Ala Lys Arg Asn Lys Ser Gly Cys Ser Lys Glu Asp Ser Lys Arg
            255                 260                 265

aat gga aat caa aac aca agc att gtt atc aag caa gaa caa tgt gat      867
Asn Gly Asn Gln Asn Thr Ser Ile Val Ile Lys Gln Glu Gln Cys Asp
        270                 275                 280

gat gtg aaa ccg gac gtg aag aat ttt gcc tct gga tca tcc act cct      915
Asp Val Lys Pro Asp Val Lys Asn Phe Ala Ser Gly Ser Ser Thr Pro
    285                 290                 295

gca ggc act tct gag agt aac gat atg gga aac aac att agg cca aga      963
Ala Gly Thr Ser Glu Ser Asn Asp Met Gly Asn Asn Ile Arg Pro Arg
300                 305                 310                 315

ggt aga ctt gga gtt atc gaa gcc ctt tct act ctt tac caa cca tca     1011
Gly Arg Leu Gly Val Ile Glu Ala Leu Ser Thr Leu Tyr Gln Pro Ser
                320                 325                 330

tat tgc aat cct gag tta ctt ggt ctt ttt gcg cat tac aac gag aca     1059
Tyr Cys Asn Pro Glu Leu Leu Gly Leu Phe Ala His Tyr Asn Glu Thr
            335                 340                 345

ttt agg tca tat caa gaa gag ttt ggt cgg gag aaa tgacttaatc          1105
Phe Arg Ser Tyr Gln Glu Glu Phe Gly Arg Glu Lys
        350                 355

atcaggtaga ttaa                                                     1119


<210> SEQ ID NO 6
<211> LENGTH: 359
<212> TYPE: PRT
<213> ORGANISM: Arabidopsis thaliana

<400> SEQUENCE: 6

Met Asp Ser Leu Ala Leu Ala Pro Gln Val Tyr Ser Arg Lys Asp Lys
1               5                   10                  15

Ser Leu Gly Val Leu Val Ala Asn Phe Leu Thr Leu Tyr Asn Arg Pro
            20                  25                  30

Asp Val Asp Leu Phe Gly Leu Asp Asp Ala Ala Ala Lys Leu Gly Val
        35                  40                  45

Glu Arg Arg Arg Ile Tyr Asp Val Val Asn Ile Leu Glu Ser Ile Gly
    50                  55                  60

Leu Val Ala Arg Ser Gly Lys Asn Gln Tyr Ser Trp Lys Gly Phe Gly
65                  70                  75                  80

Ala Val Pro Arg Ala Leu Ser Glu Leu Lys Glu Glu Gly Met Lys Glu
                85                  90                  95

Lys Phe Ala Ile Val Pro Phe Val Ala Lys Ser Glu Met Val Val Tyr
            100                 105                 110

Glu Lys Glu Gly Glu Glu Ser Phe Met Leu Ser Pro Asp Asp Gln Glu
        115                 120                 125

Phe Ser Pro Ser Pro Arg Pro Asp Asn Arg Lys Glu Arg Thr Leu Trp
    130                 135                 140

Leu Leu Ala Gln Asn Phe Val Lys Leu Phe Leu Cys Ser Asp Asp Asp
145                 150                 155                 160

Leu Val Thr Phe Asp Ser Ala Thr Lys Ala Leu Leu Asn Glu Ser Gln
                165                 170                 175

Asp Met Asn Met Arg Lys Lys Val Arg Arg Leu Tyr Asp Ile Ala Asn
            180                 185                 190

Val Phe Ser Ser Met Lys Leu Ile Glu Lys Thr His Val Pro Glu Thr
        195                 200                 205

Lys Lys Pro Ala Tyr Arg Trp Leu Gly Ser Lys Thr Ile Phe Glu Asn
    210                 215                 220

Arg Phe Ile Asp Gly Ser Ala Ser Leu Cys Asp Arg Asn Val Pro Lys
```

```
225                 230                 235                 240

Lys Arg Ala Phe Gly Thr Glu Leu Thr Asn Val Asn Ala Lys Arg Asn
                245                 250                 255

Lys Ser Gly Cys Ser Lys Glu Asp Ser Lys Arg Asn Gly Asn Gln Asn
            260                 265                 270

Thr Ser Ile Val Ile Lys Gln Glu Gln Cys Asp Asp Val Lys Pro Asp
        275                 280                 285

Val Lys Asn Phe Ala Ser Gly Ser Ser Thr Pro Ala Gly Thr Ser Glu
    290                 295                 300

Ser Asn Asp Met Gly Asn Asn Ile Arg Pro Arg Gly Arg Leu Gly Val
305                 310                 315                 320

Ile Glu Ala Leu Ser Thr Leu Tyr Gln Pro Ser Tyr Cys Asn Pro Glu
                325                 330                 335

Leu Leu Gly Leu Phe Ala His Tyr Asn Glu Thr Phe Arg Ser Tyr Gln
            340                 345                 350

Glu Glu Phe Gly Arg Glu Lys
        355


<210> SEQ ID NO 7
<211> LENGTH: 2010
<212> TYPE: DNA
<213> ORGANISM: Arabidopsis thaliana
<220> FEATURE:
<221> NAME/KEY: CDS
<222> LOCATION: (1)..(2007)

<400> SEQUENCE: 7

atg aag cag aag ggt ttt aaa gag aga ggt gtt gta gtg ggg aag aaa       48
Met Lys Gln Lys Gly Phe Lys Glu Arg Gly Val Val Val Gly Lys Lys
1               5                   10                  15

gta atg gtt gct gtt aga gct tca aag gag atc cca aaa gca gct ctt       96
Val Met Val Ala Val Arg Ala Ser Lys Glu Ile Pro Lys Ala Ala Leu
            20                  25                  30

tta tgg act tta act cat gtt gtt caa cct gga gat cga att aga ctt      144
Leu Trp Thr Leu Thr His Val Val Gln Pro Gly Asp Arg Ile Arg Leu
        35                  40                  45

ctt gtt gtt gtt cct tct aat tac aca agt aaa aag att tgg gga ttt      192
Leu Val Val Val Pro Ser Asn Tyr Thr Ser Lys Lys Ile Trp Gly Phe
    50                  55                  60

tcg agg ttc act agt gac tgt gca tca ggt tat gga aga ttt ctt gct      240
Ser Arg Phe Thr Ser Asp Cys Ala Ser Gly Tyr Gly Arg Phe Leu Ala
65                  70                  75                  80

gga acg aat tcg gat agg aaa gat gat att cat gag tca tgt tct cag      288
Gly Thr Asn Ser Asp Arg Lys Asp Asp Ile His Glu Ser Cys Ser Gln
                85                  90                  95

atg atg ttt cag tta cac aat gtt tat gat gca gag aag ata aat gtc      336
Met Met Phe Gln Leu His Asn Val Tyr Asp Ala Glu Lys Ile Asn Val
            100                 105                 110

aga atc aaa att gtt ttt gct tca ctt gat gga gtt att gct gct gaa      384
Arg Ile Lys Ile Val Phe Ala Ser Leu Asp Gly Val Ile Ala Ala Glu
        115                 120                 125

gct aag aaa tcc aac tca aac tgg gtg att tta gac agg gga ctg aag      432
Ala Lys Lys Ser Asn Ser Asn Trp Val Ile Leu Asp Arg Gly Leu Lys
    130                 135                 140

tat gag aag aaa tgc tgt att gag caa ttg gag tgc aat ctt gta gta      480
Tyr Glu Lys Lys Cys Cys Ile Glu Gln Leu Glu Cys Asn Leu Val Val
145                 150                 155                 160

atc aag aag tca cag cca aag gtt ctt cgt ctc aat ttg gtg aaa aat      528
Ile Lys Lys Ser Gln Pro Lys Val Leu Arg Leu Asn Leu Val Lys Asn
                165                 170                 175
```

-continued

```
gca gat aca gag cat cca gaa gct ata tca agg tta gct tca aag tct      576
Ala Asp Thr Glu His Pro Glu Ala Ile Ser Arg Leu Ala Ser Lys Ser
            180                 185                 190

gtc gag tct cgg aga agc tca aga act gga aaa aag ttg agg gaa ccg      624
Val Glu Ser Arg Arg Ser Ser Arg Thr Gly Lys Lys Leu Arg Glu Pro
        195                 200                 205

ttt gtg act cca gct agc agt cca gac caa gaa gtt tct tca cat act      672
Phe Val Thr Pro Ala Ser Ser Pro Asp Gln Glu Val Ser Ser His Thr
    210                 215                 220

gat ata ggg act tca tca ata tct agc tct gat gct gga gcc tca ccg      720
Asp Ile Gly Thr Ser Ser Ile Ser Ser Ser Asp Ala Gly Ala Ser Pro
225                 230                 235                 240

ttt tta gct tct cga gtc ttt gag ggt ctc aag aaa gag aat ttg tgg      768
Phe Leu Ala Ser Arg Val Phe Glu Gly Leu Lys Lys Glu Asn Leu Trp
                245                 250                 255

gtc aat gat gga agc aag agt ttc ttt gaa tcc gat tct gac tcg gat      816
Val Asn Asp Gly Ser Lys Ser Phe Phe Glu Ser Asp Ser Asp Ser Asp
            260                 265                 270

ggt gaa aag tgg agt cct tta tca atg gca tcc tca tct tct cat cct      864
Gly Glu Lys Trp Ser Pro Leu Ser Met Ala Ser Ser Ser Ser His Pro
        275                 280                 285

gtg aca aca gct gat ctt ctg agt cct agt ggg gat tta tcg aaa gct      912
Val Thr Thr Ala Asp Leu Leu Ser Pro Ser Gly Asp Leu Ser Lys Ala
    290                 295                 300

cat acc gaa act ccg aga aaa tca aga ttt gcg gtt ctt agg ctc gct      960
His Thr Glu Thr Pro Arg Lys Ser Arg Phe Ala Val Leu Arg Leu Ala
305                 310                 315                 320

tta tcg agg aaa gaa cct gaa gca gga aag gaa ata cgt aaa cct gat     1008
Leu Ser Arg Lys Glu Pro Glu Ala Gly Lys Glu Ile Arg Lys Pro Asp
                325                 330                 335

tca tgc tta aac aaa agc gtg agg gaa gtg gtt tct tta tct aga aag     1056
Ser Cys Leu Asn Lys Ser Val Arg Glu Val Val Ser Leu Ser Arg Lys
            340                 345                 350

cca gct cct gga ccg cct cca cta tgt act ata tgt caa cac aag gca     1104
Pro Ala Pro Gly Pro Pro Pro Leu Cys Thr Ile Cys Gln His Lys Ala
        355                 360                 365

cct aaa ttt gga aac cct cca aga tgg ttc act tac agc gaa ctg gag     1152
Pro Lys Phe Gly Asn Pro Pro Arg Trp Phe Thr Tyr Ser Glu Leu Glu
    370                 375                 380

acc gca aca aaa ggt ttt tct aaa ggg agt ttc ttg gct gaa ggt ggt     1200
Thr Ala Thr Lys Gly Phe Ser Lys Gly Ser Phe Leu Ala Glu Gly Gly
385                 390                 395                 400

ttt ggt tcg gtt cac cta gga act tta cca gat ggt caa att att gct     1248
Phe Gly Ser Val His Leu Gly Thr Leu Pro Asp Gly Gln Ile Ile Ala
                405                 410                 415

gtc aaa caa tat aaa att gct agt aca caa gga gac cga gaa ttc tgc     1296
Val Lys Gln Tyr Lys Ile Ala Ser Thr Gln Gly Asp Arg Glu Phe Cys
            420                 425                 430

tct gaa gtt gaa gtc ttg agc tgt gca cag cat cga aat gtt gtt atg     1344
Ser Glu Val Glu Val Leu Ser Cys Ala Gln His Arg Asn Val Val Met
        435                 440                 445

ctt att ggg cta tgt gtt gag gat ggg aaa aga ttg ctt gtt tat gag     1392
Leu Ile Gly Leu Cys Val Glu Asp Gly Lys Arg Leu Leu Val Tyr Glu
    450                 455                 460

tat atc tgc aat gga tca ttg cat tct cat ctt tat ggt atg ggg aga     1440
Tyr Ile Cys Asn Gly Ser Leu His Ser His Leu Tyr Gly Met Gly Arg
465                 470                 475                 480

gag cca ttg gga tgg tca gca cga caa aag att gcg gta gga gca gct     1488
Glu Pro Leu Gly Trp Ser Ala Arg Gln Lys Ile Ala Val Gly Ala Ala
                485                 490                 495
```

```
cgt ggg ttg aga tac ctt cat gaa gaa tgc aga gtc ggt tgc atc gtg      1536
Arg Gly Leu Arg Tyr Leu His Glu Glu Cys Arg Val Gly Cys Ile Val
            500                 505                 510

cat agg gat atg cgt cct aac aat att ctc ctc act cat gat ttt gag      1584
His Arg Asp Met Arg Pro Asn Asn Ile Leu Leu Thr His Asp Phe Glu
        515                 520                 525

cct ttg gtt gga gat ttc gga cta gcg aga tgg caa cca gaa gga gat      1632
Pro Leu Val Gly Asp Phe Gly Leu Ala Arg Trp Gln Pro Glu Gly Asp
    530                 535                 540

aaa gga gtg gaa acc cga gtg att gga act ttc ggg tac ttg gca cct      1680
Lys Gly Val Glu Thr Arg Val Ile Gly Thr Phe Gly Tyr Leu Ala Pro
545                 550                 555                 560

gaa tac gca caa agc gga cag att aca gag aaa gca gat gtt tac tca      1728
Glu Tyr Ala Gln Ser Gly Gln Ile Thr Glu Lys Ala Asp Val Tyr Ser
                565                 570                 575

ttt ggg gta gtc tta gtt gag ctt atc aca gga aga aaa gct atg gac      1776
Phe Gly Val Val Leu Val Glu Leu Ile Thr Gly Arg Lys Ala Met Asp
            580                 585                 590

ata aaa cgt cct aaa ggt caa caa tgt ctc acc gaa tgg gca aga cca      1824
Ile Lys Arg Pro Lys Gly Gln Gln Cys Leu Thr Glu Trp Ala Arg Pro
        595                 600                 605

ttg ttg cag aaa caa gcc att aac gaa ctt ctt gat ccg cgt cta atg      1872
Leu Leu Gln Lys Gln Ala Ile Asn Glu Leu Leu Asp Pro Arg Leu Met
    610                 615                 620

aat tgc tac tgt gag caa gaa gtt tat tgt atg gca cta tgt gct tac      1920
Asn Cys Tyr Cys Glu Gln Glu Val Tyr Cys Met Ala Leu Cys Ala Tyr
625                 630                 635                 640

ctc tgc att cgc cgt gac cct aac tca agg cca cga atg tct cag gtg      1968
Leu Cys Ile Arg Arg Asp Pro Asn Ser Arg Pro Arg Met Ser Gln Val
                645                 650                 655

ttg cgg atg tta gaa gga gac gtt gtc atg aat cca ata tag              2010
Leu Arg Met Leu Glu Gly Asp Val Val Met Asn Pro Ile
            660                 665


<210> SEQ ID NO 8
<211> LENGTH: 669
<212> TYPE: PRT
<213> ORGANISM: Arabidopsis thaliana

<400> SEQUENCE: 8

Met Lys Gln Lys Gly Phe Lys Glu Arg Gly Val Val Val Gly Lys Lys
1               5                   10                  15

Val Met Val Ala Val Arg Ala Ser Lys Glu Ile Pro Lys Ala Ala Leu
            20                  25                  30

Leu Trp Thr Leu Thr His Val Val Gln Pro Gly Asp Arg Ile Arg Leu
        35                  40                  45

Leu Val Val Val Pro Ser Asn Tyr Thr Ser Lys Lys Ile Trp Gly Phe
    50                  55                  60

Ser Arg Phe Thr Ser Asp Cys Ala Ser Gly Tyr Gly Arg Phe Leu Ala
65                  70                  75                  80

Gly Thr Asn Ser Asp Arg Lys Asp Asp Ile His Glu Ser Cys Ser Gln
                85                  90                  95

Met Met Phe Gln Leu His Asn Val Tyr Asp Ala Glu Lys Ile Asn Val
            100                 105                 110

Arg Ile Lys Ile Val Phe Ala Ser Leu Asp Gly Val Ile Ala Ala Glu
        115                 120                 125

Ala Lys Lys Ser Asn Ser Asn Trp Val Ile Leu Asp Arg Gly Leu Lys
    130                 135                 140
```

```
Tyr Glu Lys Lys Cys Cys Ile Glu Gln Leu Glu Cys Asn Leu Val Val
145                 150                 155                 160

Ile Lys Lys Ser Gln Pro Lys Val Leu Arg Leu Asn Leu Val Lys Asn
                165                 170                 175

Ala Asp Thr Glu His Pro Glu Ala Ile Ser Arg Leu Ala Ser Lys Ser
            180                 185                 190

Val Glu Ser Arg Arg Ser Ser Arg Thr Gly Lys Lys Leu Arg Glu Pro
        195                 200                 205

Phe Val Thr Pro Ala Ser Ser Pro Asp Gln Glu Val Ser Ser His Thr
    210                 215                 220

Asp Ile Gly Thr Ser Ser Ile Ser Ser Ser Asp Ala Gly Ala Ser Pro
225                 230                 235                 240

Phe Leu Ala Ser Arg Val Phe Glu Gly Leu Lys Lys Glu Asn Leu Trp
                245                 250                 255

Val Asn Asp Gly Ser Lys Ser Phe Phe Glu Ser Asp Ser Asp Ser Asp
            260                 265                 270

Gly Glu Lys Trp Ser Pro Leu Ser Met Ala Ser Ser Ser Ser His Pro
        275                 280                 285

Val Thr Thr Ala Asp Leu Leu Ser Pro Ser Gly Asp Leu Ser Lys Ala
    290                 295                 300

His Thr Glu Thr Pro Arg Lys Ser Arg Phe Ala Val Leu Arg Leu Ala
305                 310                 315                 320

Leu Ser Arg Lys Glu Pro Glu Ala Gly Lys Glu Ile Arg Lys Pro Asp
                325                 330                 335

Ser Cys Leu Asn Lys Ser Val Arg Glu Val Val Ser Leu Ser Arg Lys
            340                 345                 350

Pro Ala Pro Gly Pro Pro Pro Leu Cys Thr Ile Cys Gln His Lys Ala
        355                 360                 365

Pro Lys Phe Gly Asn Pro Pro Arg Trp Phe Thr Tyr Ser Glu Leu Glu
    370                 375                 380

Thr Ala Thr Lys Gly Phe Ser Lys Gly Ser Phe Leu Ala Glu Gly Gly
385                 390                 395                 400

Phe Gly Ser Val His Leu Gly Thr Leu Pro Asp Gly Gln Ile Ile Ala
                405                 410                 415

Val Lys Gln Tyr Lys Ile Ala Ser Thr Gln Gly Asp Arg Glu Phe Cys
            420                 425                 430

Ser Glu Val Glu Val Leu Ser Cys Ala Gln His Arg Asn Val Val Met
        435                 440                 445

Leu Ile Gly Leu Cys Val Glu Asp Gly Lys Arg Leu Leu Val Tyr Glu
    450                 455                 460

Tyr Ile Cys Asn Gly Ser Leu His Ser His Leu Tyr Gly Met Gly Arg
465                 470                 475                 480

Glu Pro Leu Gly Trp Ser Ala Arg Gln Lys Ile Ala Val Gly Ala Ala
                485                 490                 495

Arg Gly Leu Arg Tyr Leu His Glu Glu Cys Arg Val Gly Cys Ile Val
            500                 505                 510

His Arg Asp Met Arg Pro Asn Asn Ile Leu Leu Thr His Asp Phe Glu
        515                 520                 525

Pro Leu Val Gly Asp Phe Gly Leu Ala Arg Trp Gln Pro Glu Gly Asp
    530                 535                 540

Lys Gly Val Glu Thr Arg Val Ile Gly Thr Phe Gly Tyr Leu Ala Pro
545                 550                 555                 560

Glu Tyr Ala Gln Ser Gly Gln Ile Thr Glu Lys Ala Asp Val Tyr Ser
                565                 570                 575
```

```
Phe Gly Val Val Leu Val Glu Leu Ile Thr Gly Arg Lys Ala Met Asp
            580                 585                 590

Ile Lys Arg Pro Lys Gly Gln Gln Cys Leu Thr Glu Trp Ala Arg Pro
        595                 600                 605

Leu Leu Gln Lys Gln Ala Ile Asn Glu Leu Leu Asp Pro Arg Leu Met
    610                 615                 620

Asn Cys Tyr Cys Glu Gln Glu Val Tyr Cys Met Ala Leu Cys Ala Tyr
625                 630                 635                 640

Leu Cys Ile Arg Arg Asp Pro Asn Ser Arg Pro Arg Met Ser Gln Val
                645                 650                 655

Leu Arg Met Leu Glu Gly Asp Val Val Met Asn Pro Ile
            660                 665


<210> SEQ ID NO 9
<211> LENGTH: 417
<212> TYPE: DNA
<213> ORGANISM: Arabidopsis thaliana
<220> FEATURE:
<221> NAME/KEY: CDS
<222> LOCATION: (1)..(414)

<400> SEQUENCE: 9

atg gtg aat caa aga aag cta caa gaa gaa gaa gag gaa aag gag aat       48
Met Val Asn Gln Arg Lys Leu Gln Glu Glu Glu Glu Glu Lys Glu Asn
1               5                   10                  15

tat cct ctc att aca acc aaa gta gtt gag tat ttg cag cca gta atg       96
Tyr Pro Leu Ile Thr Thr Lys Val Val Glu Tyr Leu Gln Pro Val Met
            20                  25                  30

tgt cga gag ctt ctc tgc aaa ttt cca gat aac tct gct ttt gga ttc      144
Cys Arg Glu Leu Leu Cys Lys Phe Pro Asp Asn Ser Ala Phe Gly Phe
        35                  40                  45

gac tac tca cag agc tct ctt tgg tct cct ctc ttg cct cga aat tac      192
Asp Tyr Ser Gln Ser Ser Leu Trp Ser Pro Leu Leu Pro Arg Asn Tyr
    50                  55                  60

gcc agt cct tca gat cta gac tcc gac agt tgc gtt tgt cgg aat ctt      240
Ala Ser Pro Ser Asp Leu Asp Ser Asp Ser Cys Val Cys Arg Asn Leu
65                  70                  75                  80

aag cta agg gag ttt caa gta ggc aag aag aag aag atg aag atg atg      288
Lys Leu Arg Glu Phe Gln Val Gly Lys Lys Lys Lys Met Lys Met Met
                85                  90                  95

tca atg aag aag aac aag aag aag agt aaa tta ctg aaa cta gac ata      336
Ser Met Lys Lys Asn Lys Lys Lys Ser Lys Leu Leu Lys Leu Asp Ile
            100                 105                 110

cct tca atg aag aat gat gat tct tcc cct aaa att ggc tgt ttt ccc      384
Pro Ser Met Lys Asn Asp Asp Ser Ser Pro Lys Ile Gly Cys Phe Pro
        115                 120                 125

tct ccc tac cca agg gat gga atg gtg tgt taa                          417
Ser Pro Tyr Pro Arg Asp Gly Met Val Cys
    130                 135


<210> SEQ ID NO 10
<211> LENGTH: 138
<212> TYPE: PRT
<213> ORGANISM: Arabidopsis thaliana

<400> SEQUENCE: 10

Met Val Asn Gln Arg Lys Leu Gln Glu Glu Glu Glu Glu Lys Glu Asn
1               5                   10                  15

Tyr Pro Leu Ile Thr Thr Lys Val Val Glu Tyr Leu Gln Pro Val Met
            20                  25                  30
```

```
Cys Arg Glu Leu Leu Cys Lys Phe Pro Asp Asn Ser Ala Phe Gly Phe
        35                  40                  45

Asp Tyr Ser Gln Ser Ser Leu Trp Ser Pro Leu Leu Pro Arg Asn Tyr
    50                  55                  60

Ala Ser Pro Ser Asp Leu Asp Ser Asp Ser Cys Val Cys Arg Asn Leu
65                  70                  75                  80

Lys Leu Arg Glu Phe Gln Val Gly Lys Lys Lys Lys Met Lys Met Met
                85                  90                  95

Ser Met Lys Lys Asn Lys Lys Lys Ser Lys Leu Leu Lys Leu Asp Ile
            100                 105                 110

Pro Ser Met Lys Asn Asp Asp Ser Ser Pro Lys Ile Gly Cys Phe Pro
        115                 120                 125

Ser Pro Tyr Pro Arg Asp Gly Met Val Cys
    130                 135


<210> SEQ ID NO 11
<211> LENGTH: 1497
<212> TYPE: DNA
<213> ORGANISM: Arabidopsis thaliana
<220> FEATURE:
<221> NAME/KEY: CDS
<222> LOCATION: (178)..(1296)

<400> SEQUENCE: 11

ttttcgctct tctccagaaa cattccgttt cagatatttt tgatttttga atttgttttc      60

gctctctctc tctctctgct tagattagat ctgttcctgt gaattgattc tctgtttcat     120

cgtttgctca cgccgccgtt ttcgccggag gtggaagctc tcatcgccgt ttcgaaa        177

atg ccg gcg aat gat gct gaa tac gat ctc aaa gtt tta tct caa tct       225
Met Pro Ala Asn Asp Ala Glu Tyr Asp Leu Lys Val Leu Ser Gln Ser
1               5                   10                  15

gcg tca gca ggg gat tac aca ttt gcg aat gag gat aac ttg gag cat       273
Ala Ser Ala Gly Asp Tyr Thr Phe Ala Asn Glu Asp Asn Leu Glu His
            20                  25                  30

tgt acg aag tat ttg aat cag acg atg gtt aca ttt gga ttt ccc gcc       321
Cys Thr Lys Tyr Leu Asn Gln Thr Met Val Thr Phe Gly Phe Pro Ala
        35                  40                  45

tcg ctc gat ctc ttt tcg aat gat cct gtt tct ata tca agg acc tgc       369
Ser Leu Asp Leu Phe Ser Asn Asp Pro Val Ser Ile Ser Arg Thr Cys
    50                  55                  60

aat tgt atg tac tcg ttg ctg cag cag cga caa cgt gat ata gag ttt       417
Asn Cys Met Tyr Ser Leu Leu Gln Gln Arg Gln Arg Asp Ile Glu Phe
65                  70                  75                  80

aga gaa tct gct aat gag ctg aga cag aga cag caa tcg gat ata gct       465
Arg Glu Ser Ala Asn Glu Leu Arg Gln Arg Gln Gln Ser Asp Ile Ala
                85                  90                  95

aga ctt gaa gct aaa gtt gag agg ctt gaa gcg cta ctc caa cag aag       513
Arg Leu Glu Ala Lys Val Glu Arg Leu Glu Ala Leu Leu Gln Gln Lys
            100                 105                 110

gac aga gaa att gca aca att acc aga acc gaa gcc aaa aac act gca       561
Asp Arg Glu Ile Ala Thr Ile Thr Arg Thr Glu Ala Lys Asn Thr Ala
        115                 120                 125

gct ttg aag tct cag att gaa aag tta cag cag gag agg gat gaa ttc       609
Ala Leu Lys Ser Gln Ile Glu Lys Leu Gln Gln Glu Arg Asp Glu Phe
    130                 135                 140

caa agg atg gtg att ggt aac cag caa gtg aag gct caa cag ata cac       657
Gln Arg Met Val Ile Gly Asn Gln Gln Val Lys Ala Gln Gln Ile His
145                 150                 155                 160

gaa atg aag aaa aag gag aag gat tac att aag ttg cag gaa cgg ctg       705
Glu Met Lys Lys Lys Glu Lys Asp Tyr Ile Lys Leu Gln Glu Arg Leu
```

-continued

```
                165                 170                 175

aat caa gtg tta atg gag aaa aag aaa gaa tca aga tct gga atg gag      753
Asn Gln Val Leu Met Glu Lys Lys Lys Glu Ser Arg Ser Gly Met Glu
            180                 185                 190

att atg aat ttg cta cag aaa gaa ggg agg caa cgt ggt acc tgg aat      801
Ile Met Asn Leu Leu Gln Lys Glu Gly Arg Gln Arg Gly Thr Trp Asn
        195                 200                 205

ggc aag aag act gat acc gac ttc tat aaa aag ata gtg gat gcg tac      849
Gly Lys Lys Thr Asp Thr Asp Phe Tyr Lys Lys Ile Val Asp Ala Tyr
    210                 215                 220

gaa gcg aaa aat caa gaa ttg atg gct gag aac act agt cta aga gca      897
Glu Ala Lys Asn Gln Glu Leu Met Ala Glu Asn Thr Ser Leu Arg Ala
225                 230                 235                 240

tta ctt cga tcc atg cag aca gat atg cgt gat ttc tta aat gct cca      945
Leu Leu Arg Ser Met Gln Thr Asp Met Arg Asp Phe Leu Asn Ala Pro
                245                 250                 255

aat ggg tca gct aca ttg gct gga agt gag aaa cgt gag gct gat cct      993
Asn Gly Ser Ala Thr Leu Ala Gly Ser Glu Lys Arg Glu Ala Asp Pro
            260                 265                 270

tca caa tct cca ctg ggt ggg aag acg gac gtg ttt gat cta cct tac     1041
Ser Gln Ser Pro Leu Gly Gly Lys Thr Asp Val Phe Asp Leu Pro Tyr
        275                 280                 285

cgg atg gct aga ggt caa ata gaa gaa agt ttg cgt act aag atg gct     1089
Arg Met Ala Arg Gly Gln Ile Glu Glu Ser Leu Arg Thr Lys Met Ala
    290                 295                 300

tcc ata aag gaa agc atg gtc cag tta caa gat gca cct aaa aga gca     1137
Ser Ile Lys Glu Ser Met Val Gln Leu Gln Asp Ala Pro Lys Arg Ala
305                 310                 315                 320

tct gtt aca tct gaa gca aca gag aga gag ctt gaa ctc gaa gct cag     1185
Ser Val Thr Ser Glu Ala Thr Glu Arg Glu Leu Glu Leu Glu Ala Gln
                325                 330                 335

ctt gtc gag gca aga agc ata atc caa gaa cag gag tcc ata atg tcg     1233
Leu Val Glu Ala Arg Ser Ile Ile Gln Glu Gln Glu Ser Ile Met Ser
            340                 345                 350

aaa cat ctc cca aaa tca gag cag cga agg gaa tct gta gct tcg ttg     1281
Lys His Leu Pro Lys Ser Glu Gln Arg Arg Glu Ser Val Ala Ser Leu
        355                 360                 365

gca gct gag gga gta tgaaaatgtc taggagctca aaatcagtgg atccaagttg     1336
Ala Ala Glu Gly Val
    370

ctaaaagaga cttgtcgcaa aatgtagtcg tagtactgta ttcactacca ccaaaactct   1396

ccttggatat ctaagtgatg tatattcaac ttttagttgt gacaaatcag agatctttta   1456

tccttttggg atatcataat cttattatat ggttgtctaa c                       1497


<210> SEQ ID NO 12
<211> LENGTH: 373
<212> TYPE: PRT
<213> ORGANISM: Arabidopsis thaliana

<400> SEQUENCE: 12

Met Pro Ala Asn Asp Ala Glu Tyr Asp Leu Lys Val Leu Ser Gln Ser
1               5                   10                  15

Ala Ser Ala Gly Asp Tyr Thr Phe Ala Asn Glu Asp Asn Leu Glu His
            20                  25                  30

Cys Thr Lys Tyr Leu Asn Gln Thr Met Val Thr Phe Gly Phe Pro Ala
        35                  40                  45

Ser Leu Asp Leu Phe Ser Asn Asp Pro Val Ser Ile Ser Arg Thr Cys
    50                  55                  60
```

-continued

```
Asn Cys Met Tyr Ser Leu Leu Gln Gln Arg Gln Arg Asp Ile Glu Phe
65                  70                  75                  80

Arg Glu Ser Ala Asn Glu Leu Arg Gln Arg Gln Gln Ser Asp Ile Ala
                85                  90                  95

Arg Leu Glu Ala Lys Val Glu Arg Leu Glu Ala Leu Leu Gln Gln Lys
            100                 105                 110

Asp Arg Glu Ile Ala Thr Ile Thr Arg Thr Glu Ala Lys Asn Thr Ala
        115                 120                 125

Ala Leu Lys Ser Gln Ile Glu Lys Leu Gln Gln Glu Arg Asp Glu Phe
    130                 135                 140

Gln Arg Met Val Ile Gly Asn Gln Gln Val Lys Ala Gln Gln Ile His
145                 150                 155                 160

Glu Met Lys Lys Lys Glu Lys Asp Tyr Ile Lys Leu Gln Glu Arg Leu
                165                 170                 175

Asn Gln Val Leu Met Glu Lys Lys Lys Glu Ser Arg Ser Gly Met Glu
            180                 185                 190

Ile Met Asn Leu Leu Gln Lys Glu Gly Arg Gln Arg Gly Thr Trp Asn
        195                 200                 205

Gly Lys Lys Thr Asp Thr Asp Phe Tyr Lys Lys Ile Val Asp Ala Tyr
    210                 215                 220

Glu Ala Lys Asn Gln Glu Leu Met Ala Glu Asn Thr Ser Leu Arg Ala
225                 230                 235                 240

Leu Leu Arg Ser Met Gln Thr Asp Met Arg Asp Phe Leu Asn Ala Pro
                245                 250                 255

Asn Gly Ser Ala Thr Leu Ala Gly Ser Glu Lys Arg Glu Ala Asp Pro
            260                 265                 270

Ser Gln Ser Pro Leu Gly Gly Lys Thr Asp Val Phe Asp Leu Pro Tyr
        275                 280                 285

Arg Met Ala Arg Gly Gln Ile Glu Glu Ser Leu Arg Thr Lys Met Ala
    290                 295                 300

Ser Ile Lys Glu Ser Met Val Gln Leu Gln Asp Ala Pro Lys Arg Ala
305                 310                 315                 320

Ser Val Thr Ser Glu Ala Thr Glu Arg Glu Leu Glu Leu Glu Ala Gln
                325                 330                 335

Leu Val Glu Ala Arg Ser Ile Ile Gln Glu Gln Glu Ser Ile Met Ser
            340                 345                 350

Lys His Leu Pro Lys Ser Glu Gln Arg Arg Glu Ser Val Ala Ser Leu
        355                 360                 365

Ala Ala Glu Gly Val
    370
```

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggggtaccat gggaagtaac cgtcctaag 29

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
acgcgtcgac tcaaactgcc tccttaagat t 31

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggggtaccgg aaaatgggta gcaagatg 28

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
cgagctcagg gtttaagctt ggcttcc 27

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggggacaagt ttgtacaaaa aagcaggctt catggattct ctcgctctcg c 51

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ggggaccact ttgtacaaga aagctgggta tttctcccga ccaaact 47

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ggggacaagt ttgtacaaaa aagcaggctt catgaagcag aagggtttta aa 52

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ggggaccact ttgtacaaga aagctgggtc ctatattgga ttcatgacaa c 51

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ggggacaagt ttgtacaaaa aagcaggctt catggtgaat caaagaaagc ta 52

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggggaccact ttgtacaaga aagctgggtc ttaacacacc attccatccc t 51

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ggggacaagt ttgtacaaaa aagcaggctt catgccggcg aatgatgctg aa 52

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggggaccact ttgtacaaga aagctgggtc tcatactccc tcagctgcca a 51

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tctagaggat cccccggggg taccgtcgac atggcaatga gtaaaggaga a 51

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cgagctctta tttgtaaagt tcatc 25

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
acgcgtcgac aactgcctcc ttaagattg 29

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggactagtga gctcgcacac taatgcgaag aaag 34

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ccgctcgagt ctagagcaga tgcatctaaa gattc 35

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
agcttgccaa gaaggcattg 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tcatcaacga cgcagtcaga 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgcttcagcg gttttcttag 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
atcctccatt gcaagtaccg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
tgtatgtgtt ggccgtaatg 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
tggtgtctct tgcatgctta 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
ctctatgccc ctgaaatcca 20

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
acctccacaa gcaatcaac 19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
caaagcctcc gatctcaaag 20

<210> SEQ ID NO 39

<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
cttgtccggt agctctccag 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
cgatgacgaa gaaacgagca 20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
tggcattaac gcaaacactt g 21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
ctggatcggt ggttccattc 20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
cctggacctg cctcatcata c 21

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
gggggatccg cgggtttctg gagtttaatg 30

<210> SEQ ID NO 45
<211> LENGTH: 29
<212> TYPE: DNA

<213> ORGANISM: Artificial Sequence
<220> FEATURE:
<223> OTHER INFORMATION: Description of Artificial Sequence: Synthetic primer

<400> SEQUENCE: 45
cctctagaga ctctaattgg ataccgagg 29

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ggggtacctt aggatccgtc actctcatca gtgct 35

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gctctagagg atccatgaca gttctaaaca aacat 35

<210> SEQ ID NO 48
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ggggacaagt ttgtacaaaa aagcaggctt cgccaccatg gacatggaga gcgagaagg 59

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ggggaccact ttgtacaaga aagctgggtc ctattttcct tcaatcagag actt 54

<210> SEQ ID NO 50
<211> LENGTH: 110
<212> TYPE: PRT
<213> ORGANISM: Unknown
<220> FEATURE:
<223> OTHER INFORMATION: Description of Unknown: ILP1 polypeptide

<400> SEQUENCE: 50

```
Lys Glu Ser His Ala Lys Thr Leu Ser Ser Leu Thr Lys Thr Asp Glu
1               5                   10                  15

Asn Leu Thr Ala Ser Leu Met Ser Ile Thr Ala Leu Glu Ser Ser Leu
            20                  25                  30

Ser Ala Ala Gly Asp Lys Tyr Val Phe Met Gln Lys Leu Arg Asp Phe
        35                  40                  45
```

```
Ile Ser Val Ile Cys Asp Phe Met Gln Asn Lys Gly Ser Leu Ile Glu
    50                  55                  60

Glu Ile Glu Asp Gln Met Lys Glu Leu Asn Glu Lys His Ala Leu Ser
65                  70                  75                  80

Ile Leu Glu Arg Arg Ile Ala Asp Asn Asn Asp Glu Met Ile Glu Leu
                85                  90                  95

Gly Ala Ala Val Lys Ala Ala Met Thr Val Leu Asn Lys His
            100                 105                 110


<210> SEQ ID NO 51
<211> LENGTH: 107
<212> TYPE: PRT
<213> ORGANISM: Arabidopsis thaliana

<400> SEQUENCE: 51

Pro Gln Glu Gln Pro Gln Met Tyr Ala Gly Arg Pro Glu Glu Leu Ala
1               5                   10                  15

Lys Glu Pro Asp Glu Asn Leu Thr Met Ser Ile Ala Ala Ala Glu Ser
            20                  25                  30

Cys Pro Ser Ala Pro Val Tyr Lys Tyr Ala Ser Leu Gln Glu Ile Ser
        35                  40                  45

Asp Phe Lys Ser Val Phe Arg Asn Phe Met Gln Gly Ile Cys Val Ala
    50                  55                  60

Phe Val Cys Val Ser Gly Ala Phe Ile Ser Ile Lys Arg Leu Leu Ser
65                  70                  75                  80

Ile Phe Phe Leu Ser Gln Lys Asn Gly Tyr Leu Ile Thr Ala Ile Glu
                85                  90                  95

Asp Gln Met Lys Val Asp Gly Tyr Ser Leu Ile
            100                 105


<210> SEQ ID NO 52
<211> LENGTH: 100
<212> TYPE: PRT
<213> ORGANISM: Homo sapiens

<400> SEQUENCE: 52

Ser Met Lys Glu Leu His Lys Thr Asn Arg Gln Gln His Glu Lys His
1               5                   10                  15

Leu Gln Ser Arg Val Asp Ser Thr Arg Ala Ile Glu Arg Leu Glu Gly
            20                  25                  30

Ser Ser Gly Gly Ile Gly Glu Arg Tyr Lys Phe Leu Gln Glu Met Arg
        35                  40                  45

Gly Tyr Val Gln Asp Leu Leu Glu Cys Phe Ser Glu Lys Val Pro Leu
    50                  55                  60

Ile Asn Glu Leu Glu Ser Ala Ile His Gln Leu Tyr Lys Gln Arg Ala
65                  70                  75                  80

Ser Arg Leu Val Gln Arg Arg Gln Asp Asp Ile Lys Asp Glu Ser Ser
                85                  90                  95

Glu Phe Ser Ser
            100


<210> SEQ ID NO 53
<211> LENGTH: 100
<212> TYPE: PRT
<213> ORGANISM: Mus musculus

<400> SEQUENCE: 53

Lys Glu Leu His Lys Thr Asn Gln Gln Gln His Glu Lys His Leu Gln
1               5                   10                  15
```

```
Ser Arg Val Asp Ser Thr Arg Ala Ile Glu Arg Leu Glu Gly Ser Ser
            20                  25                  30

Gly Gly Ile Gly Glu Arg Tyr Lys Phe Leu Gln Glu Met Arg Gly Tyr
        35                  40                  45

Val Gln Asp Leu Leu Glu Cys Phe Ser Glu Lys Val Pro Leu Ile Asn
    50                  55                  60

Glu Leu Glu Ser Ala Ile His Gln Leu Tyr Lys Gln Arg Ala Ser Arg
65                  70                  75                  80

Leu Val Gln Arg Arg Gln Asp Asp Ile Lys Asp Glu Ser Ser Glu Phe
                85                  90                  95

Ser Ser His Ser
            100


<210> SEQ ID NO 54
<211> LENGTH: 90
<212> TYPE: PRT
<213> ORGANISM: Homo sapiens

<400> SEQUENCE: 54

Arg Leu Thr Leu Leu Gln Glu Thr His Arg Ser His Leu Arg Glu Tyr
1               5                   10                  15

Glu Lys Tyr Val Gln Asp Val Lys Ser Ser Lys Ser Thr Ile Gln Asn
            20                  25                  30

Leu Glu Ser Ser Ser Asn Gln Ala Leu Asn Cys Lys Phe Tyr Lys Ser
        35                  40                  45

Met Lys Ile Tyr Val Glu Asn Leu Ile Asp Cys Leu Asn Glu Lys Ile
    50                  55                  60

Ile Asn Ile Gln Glu Ile Glu Ser Ser Met His Ala Leu Leu Leu Lys
65                  70                  75                  80

Gln Ala Met Thr Phe Met Lys Arg Arg Gln
                85                  90


<210> SEQ ID NO 55
<211> LENGTH: 288
<212> TYPE: PRT
<213> ORGANISM: Unknown
<220> FEATURE:
<223> OTHER INFORMATION: Description of Unknown: ILP1 polypeptide

<400> SEQUENCE: 55

Ser Ala Tyr Lys Glu Thr Arg Asp Ser Leu Leu Gln Cys Ala Asp Lys
1               5                   10                  15

Val Phe Ser Asp Ala Ser Glu Glu Tyr Ser Gln Leu Ser Lys Val Lys
            20                  25                  30

Ala Arg Phe Glu Arg Trp Lys Arg Asp Tyr Ser Ser Thr Tyr Arg Asp
        35                  40                  45

Ala Tyr Met Ser Leu Thr Val Pro Ser Ile Phe Ser Pro Tyr Val Arg
    50                  55                  60

Leu Glu Leu Leu Lys Trp Asp Pro Leu His Gln Asp Val Asp Phe Phe
65                  70                  75                  80

Asp Met Lys Trp His Gly Leu Leu Phe Asp Tyr Gly Lys Pro Glu Asp
                85                  90                  95

Gly Asp Asp Phe Ala Pro Asp Asp Thr Asp Ala Asn Leu Val Pro Glu
            100                 105                 110

Leu Val Glu Lys Val Ala Ile Pro Ile Leu His His Gln Ile Val Arg
        115                 120                 125

Cys Trp Asp Ile Leu Ser Thr Arg Glu Thr Arg Asn Ala Val Ala Ala
```

-continued

```
    130                 135                 140

Thr Ser Leu Val Thr Asn Tyr Val Ser Ala Ser Ser Glu Ala Leu Ala
145                 150                 155                 160

Glu Leu Phe Ala Ala Ile Arg Ala Arg Leu Val Glu Ala Ile Ala Ala
                165                 170                 175

Ile Ser Val Pro Thr Trp Asp Pro Leu Val Leu Lys Ala Val Pro Asn
            180                 185                 190

Thr Pro Gln Val Ala Ala Tyr Arg Phe Gly Thr Ser Val Arg Leu Met
        195                 200                 205

Arg Asn Ile Cys Met Trp Lys Asp Ile Leu Ala Leu Pro Val Leu Glu
    210                 215                 220

Asn Leu Ala Leu Ser Asp Leu Leu Phe Gly Lys Val Leu Pro His Val
225                 230                 235                 240

Arg Ser Ile Ala Ser Asn Ile His Asp Ala Val Thr Arg Thr Glu Arg
                245                 250                 255

Ile Val Ala Ser Leu Ser Gly Val Trp Thr Gly Pro Ser Val Thr Arg
            260                 265                 270

Thr His Ser Arg Pro Leu Gln Pro Leu Val Asp Cys Thr Leu Thr Leu
        275                 280                 285


<210> SEQ ID NO 56
<211> LENGTH: 287
<212> TYPE: PRT
<213> ORGANISM: Arabidopsis thaliana

<400> SEQUENCE: 56

Ser Ala Tyr Glu Glu Ala Arg Asp Ser Leu Leu Gln Arg Ala Asp Lys
1               5                   10                  15

Ile Phe Ser Asp Ala Ser Val Val Tyr Ser Glu Leu Ser Arg Val Lys
            20                  25                  30

Ser Ile Phe Lys Arg Gly Ala Arg His Pro Ser Pro Ala Phe Arg Ala
        35                  40                  45

Ala Tyr Thr Ser Leu Thr Val Pro Ser Met Tyr Ser Pro Tyr Leu Arg
    50                  55                  60

Leu Glu Leu Leu Arg Trp Asp Pro Leu His Gln Asp Val Asp Phe Ser
65                  70                  75                  80

Asp Met Asn Trp His Gly Leu Leu Phe His Ser Arg Ile Val Cys Gly
                85                  90                  95

Ser Thr Pro Val Cys Thr Asn Pro Asn Phe Val Ser Glu Leu Val Lys
            100                 105                 110

Tyr Val Ala Val Pro Ile Leu His His Arg Ile Val Arg Cys Trp Asp
        115                 120                 125

Ile Leu Ser Thr Arg Glu Thr Arg Asn Val Val Ala Ala Thr Ser Leu
    130                 135                 140

Val Ala Arg Tyr Val Phe Pro Ser Ser Glu Ala Leu Ala Glu Leu Ser
145                 150                 155                 160

Leu Ala Ile His Ala Arg Leu Val Glu Ala Ile Ile Ala Ile Ser Val
                165                 170                 175

Pro Thr Trp Asp Pro Gln Val Ser Lys Asp Val Pro Asn Ala Pro Gln
            180                 185                 190

Val Ala Ala Tyr Arg Phe Gly Thr Ser Val Arg Leu Met Arg Asn Ile
        195                 200                 205

Cys Met Trp Lys Asp Val Met Glu Leu Pro Val Leu Glu Lys Leu Ala
    210                 215                 220

Leu Ser Asp Leu Leu Phe Gly Lys Val Leu Pro His Val Arg Ser Ile
```

```
225                 230                 235                 240

Ala Ser Glu Ser Asn Ile His Asp Ala Val Thr Lys Thr Glu Arg Ile
                245                 250                 255

Val Ala Ser Leu Ser Gly Val Trp Thr Gly Pro Ser Val Thr Arg Thr
            260                 265                 270

His Ser His Leu Leu Gln Pro Leu Val Asp Cys Thr Leu Thr Leu
        275                 280                 285


<210> SEQ ID NO 57
<211> LENGTH: 289
<212> TYPE: PRT
<213> ORGANISM: Homo sapiens

<400> SEQUENCE: 57

Thr Asn Phe Asn Leu Glu Lys Asp Arg Ile Ser Lys Glu Ser Gly Lys
1               5                   10                  15

Val Phe Glu Asp Val Leu Glu Ser Phe Tyr Ser Ile Asp Cys Ile Lys
            20                  25                  30

Ser Gln Phe Glu Ala Trp Arg Ser Lys Tyr Tyr Thr Ser Tyr Lys Asp
        35                  40                  45

Ala Tyr Ile Gly Leu Cys Leu Pro Lys Leu Phe Asn Pro Leu Ile Arg
    50                  55                  60

Leu Gln Leu Leu Thr Trp Thr Pro Leu Glu Ala Lys Cys Arg Asp Phe
65                  70                  75                  80

Glu Asn Met Leu Trp Phe Glu Ser Leu Leu Phe Tyr Gly Cys Glu Glu
                85                  90                  95

Arg Glu Gln Glu Lys Asp Asp Val Asp Val Ala Leu Leu Pro Thr Ile
            100                 105                 110

Val Glu Lys Val Ile Leu Pro Lys Leu Thr Val Ile Ala Glu Asn Met
        115                 120                 125

Trp Asp Pro Phe Ser Thr Thr Gln Thr Ser Arg Met Val Gly Ile Thr
    130                 135                 140

Leu Lys Leu Ile Asn Gly Tyr Pro Ser Val Val Asn Ala Glu Asn Lys
145                 150                 155                 160

Asn Thr Gln Val Tyr Leu Lys Ala Leu Leu Leu Arg Met Arg Arg Thr
                165                 170                 175

Leu Asp Asp Asp Val Phe Met Pro Leu Tyr Pro Lys Asn Val Leu Glu
            180                 185                 190

Asn Lys Asn Ser Gly Pro Tyr Leu Phe Phe Gln Arg Gln Phe Trp Ser
        195                 200                 205

Ser Val Lys Leu Leu Gly Asn Phe Leu Gln Trp Tyr Gly Ile Phe Ser
    210                 215                 220

Asn Lys Thr Leu Gln Glu Leu Ser Ile Asp Gly Leu Leu Asn Arg Tyr
225                 230                 235                 240

Ile Leu Met Ala Phe Gln Asn Ser Glu Tyr Gly Asp Asp Ser Ile Lys
                245                 250                 255

Lys Ala Gln Asn Val Ile Asn Cys Phe Pro Lys Gln Trp Phe Met Asn
            260                 265                 270

Leu Lys Gly Glu Arg Thr Ile Ser Gln Leu Glu Asn Phe Cys Arg Tyr
        275                 280                 285

Leu


<210> SEQ ID NO 58
<211> LENGTH: 289
<212> TYPE: PRT
<213> ORGANISM: Mus musculus
```

<400> SEQUENCE: 58

Thr Asn Phe Asn Leu Glu Lys Asp Arg Ile Leu Lys Glu Ser Ser Lys
1               5                   10                  15

Val Phe Glu Asp Val Leu Glu Ser Phe Tyr Ser Ile Asp Cys Ile Lys
            20                  25                  30

Ala Gln Phe Glu Ala Trp Arg Ser Lys Tyr Tyr Met Ser Tyr Lys Asp
        35                  40                  45

Ala Tyr Ile Gly Leu Cys Leu Pro Lys Leu Phe Asn Pro Leu Ile Arg
    50                  55                  60

Leu Gln Leu Leu Thr Trp Thr Pro Leu Glu Ala Lys Cys Arg Asp Phe
65                  70                  75                  80

Glu Thr Met Leu Trp Phe Glu Ser Leu Leu Phe Tyr Gly Cys Glu Asp
                85                  90                  95

Arg Glu Gln Glu Lys Asp Glu Ala Asp Val Ala Leu Leu Pro Thr Ile
            100                 105                 110

Val Glu Lys Val Ile Leu Pro Lys Leu Thr Val Ile Ala Glu Thr Met
        115                 120                 125

Trp Asp Pro Phe Ser Thr Thr Gln Thr Ser Arg Met Val Gly Ile Thr
    130                 135                 140

Met Lys Leu Ile Asn Gly Tyr Pro Ser Val Val Asn Ala Asp Asn Lys
145                 150                 155                 160

Asn Thr Gln Val Tyr Leu Lys Ala Leu Leu Leu Arg Met Arg Arg Thr
                165                 170                 175

Leu Asp Asp Asp Val Phe Met Pro Leu Tyr Pro Lys Asn Val Leu Glu
            180                 185                 190

Asn Lys Asn Ser Gly Pro Tyr Leu Phe Phe Gln Arg Gln Phe Trp Ser
        195                 200                 205

Ser Val Lys Leu Leu Gly Asn Phe Leu Gln Trp Tyr Gly Ile Phe Ser
    210                 215                 220

Asn Lys Thr Leu Gln Glu Leu Ser Ile Asp Gly Leu Leu Asn Arg Tyr
225                 230                 235                 240

Ile Leu Met Ala Phe Gln Asn Ser Glu Tyr Gly Asp Asp Ser Ile Arg
                245                 250                 255

Lys Ala Gln Asn Val Ile Asn Cys Phe Pro Lys Gln Trp Phe Val Asn
            260                 265                 270

Leu Lys Gly Glu Arg Thr Ile Ser Gln Leu Glu Asn Phe Cys Arg Tyr
        275                 280                 285

Leu

<210> SEQ ID NO 59
<211> LENGTH: 288
<212> TYPE: PRT
<213> ORGANISM: Drosophila melanogaster

<400> SEQUENCE: 59

Gln Glu Leu Ser Val Thr Thr Met Ala Gln Ile Glu Ser Gln Ser Val
1               5                   10                  15

Asp Ala Leu Glu Asp Val Thr Asp Asp Phe Ser Lys Ile Glu Leu Ile
            20                  25                  30

Leu Met Lys Phe Phe Ala Trp Arg Lys Thr Asp Met Ser Ser Tyr Gln
        35                  40                  45

Asp Ala Phe Val Ser Leu Cys Leu Pro Lys Val Leu Ala Pro Leu Val
    50                  55                  60

Arg His Glu Leu Val Leu Trp Ser Pro Leu Leu Asp Val Tyr Ala Asp

-continued

```
65                  70                  75                  80

Ile Glu Asn Met Arg Trp Tyr Gln Ala Cys Met Leu Tyr Ala Ser Gln
                85                  90                  95

Ala Asp Glu Thr Val Glu Gln Leu Lys Ile Asp Pro Asp Ile Asn Leu
            100                 105                 110

Val Pro Ala Leu Ile Glu Lys Ile Val Leu Pro Lys Val Thr Ala Leu
        115                 120                 125

Val Thr Glu Cys Trp Asp Pro Leu Ser Thr Thr Gln Thr Leu Arg Leu
    130                 135                 140

Val Gly Phe Ile Asn Arg Leu Gly Arg Glu Phe Pro Leu Ser Gly Thr
145                 150                 155                 160

Asn Lys Gln Leu Asn Lys Leu Phe Glu Ser Ile Met Glu Arg Met Arg
                165                 170                 175

Leu Ala Leu Glu Asn Asp Val Phe Ile Pro Ile Phe Pro Lys Gln Val
            180                 185                 190

Gln Glu Ala Lys Thr Ser Phe Phe Gln Arg Gln Phe Cys Ser Gly Leu
        195                 200                 205

Lys Leu Phe Arg Asn Phe Leu Ser Trp Gln Gly Ile Leu Ala Asp Lys
    210                 215                 220

Leu Leu Arg Glu Leu Ala Ile Gly Ala Leu Leu Asn Arg Tyr Leu Leu
225                 230                 235                 240

Leu Ala Met Arg Val Cys Thr Pro Asn Asp Ala Ile Asn Lys Ala Tyr
                245                 250                 255

Ile Ile Val Asn Thr Leu Pro Thr Val Trp Leu Leu Pro Asn Ser Glu
            260                 265                 270

Thr Leu Lys Asn Met Glu Leu Phe Ile Gly Tyr Ile Lys Gln Thr Leu
        275                 280                 285


<210> SEQ ID NO 60
<211> LENGTH: 296
<212> TYPE: PRT
<213> ORGANISM: Homo sapiens

<400> SEQUENCE: 60

Glu Met Ile Asp Phe Gln Lys Ser Gln Gly Asp Ile Leu Gln Lys Gln
1               5                   10                  15

Lys Lys Val Phe Glu Asp Val Gln Asp Asp Phe Cys Asn Ile Gln Asn
            20                  25                  30

Ile Leu Leu Lys Phe Gln Gln Trp Arg Glu Lys Phe Pro Asp Ser Tyr
        35                  40                  45

Tyr Glu Ala Phe Ile Ser Leu Cys Ile Pro Lys Leu Leu Asn Pro Leu
    50                  55                  60

Ile Arg Val Gln Leu Ile Asp Trp Asn Pro Leu Lys Leu Glu Ser Thr
65                  70                  75                  80

Gly Leu Lys Glu Met Pro Trp Phe Lys Ser Val Glu Glu Phe Met Asp
                85                  90                  95

Ser Ser Val Glu Asp Ser Lys Lys Glu Ser Ser Ser Asp Lys Lys Val
            100                 105                 110

Leu Ser Ala Ile Ile Asn Lys Thr Ile Ile Pro Arg Leu Thr Asp Phe
        115                 120                 125

Val Glu Phe Leu Trp Asp Pro Leu Ser Thr Ser Gln Thr Thr Ser Leu
    130                 135                 140

Ile Thr His Cys Arg Val Ile Leu Glu Glu His Ser Thr Cys Glu Asn
145                 150                 155                 160

Glu Val Ser Lys Ser Arg Gln Asp Leu Leu Lys Ser Ile Val Ser Arg
```

```
                165                 170                 175

Met Lys Lys Ala Val Glu Asp Asp Val Phe Ile Pro Leu Tyr Pro Lys
            180                 185                 190

Ser Ala Val Glu Asn Lys Thr Ser Pro His Ser Lys Phe Gln Glu Arg
        195                 200                 205

Gln Phe Trp Ser Gly Leu Lys Leu Phe Arg Asn Ile Leu Leu Trp Asn
    210                 215                 220

Gly Leu Leu Thr Asp Asp Thr Leu Gln Glu Leu Gly Leu Gly Lys Leu
225                 230                 235                 240

Leu Asn Arg Tyr Leu Ile Ile Ala Leu Leu Asn Ala Thr Pro Gly Pro
                245                 250                 255

Asp Val Val Lys Lys Cys Asn Gln Val Ala Ala Cys Leu Pro Glu Lys
            260                 265                 270

Trp Phe Glu Asn Ser Ala Met Arg Thr Ser Ile Pro Gln Leu Glu Asn
        275                 280                 285

Phe Ile Gln Phe Leu Leu Gln Ser
    290                 295


<210> SEQ ID NO 61
<211> LENGTH: 310
<212> TYPE: PRT
<213> ORGANISM: Caenorhabditis elegans

<400> SEQUENCE: 61

Thr Asp Asp Glu Glu Pro Thr Pro Gln Ser Met Asn Asp Gln Lys Ile
1               5                   10                  15

Cys Asp Glu Val Glu Ala Val Ala Ser Val Leu Phe Ala Glu Ala Leu
            20                  25                  30

Asp Glu Tyr Ser Asp Leu Arg Lys Val Phe Gly Arg Met Thr Asp Trp
        35                  40                  45

Leu Ala Val Asp Pro Lys Ser Phe Gln Asp Ala Tyr Val Tyr Leu Cys
    50                  55                  60

Ile Pro Lys Leu Ser Ser Pro Tyr Val Arg Leu Gln Ile Leu Arg Ala
65                  70                  75                  80

Asp Phe Leu Arg Lys Glu Thr Ile Leu Thr Ser Met Gln Trp Phe His
                85                  90                  95

Ile Ala Met Leu Ala Gly Ser Glu Asn Ala Glu Ile Asp Gln Ser His
            100                 105                 110

Glu Ile Leu Val Glu Leu Ala Pro Ala Ile Val Glu Lys Val Val Ile
        115                 120                 125

Pro Phe Leu Ile Gly Leu Phe Leu Lys Leu Ser Ser Asn Phe Asp Thr
    130                 135                 140

Val Lys Glu Glu Trp Asp Pro Met Ser Leu Arg Gln Thr Arg His Leu
145                 150                 155                 160

Thr Thr Phe Cys Ser Leu Phe Glu Lys Leu Pro Asn Leu Thr Glu Lys
                165                 170                 175

Ser Lys Gln Phe Asn Ala Phe Leu Asn Ala Ile Arg Glu Arg Ile Cys
            180                 185                 190

Asp Cys Ile Ser Glu Asp Leu Phe Met Pro Ile Phe Met Pro Asn Ala
        195                 200                 205

Leu Glu Gln Pro Ile Cys Arg Gln Phe His Asp Arg Gln Phe Trp Thr
    210                 215                 220

Cys Ile Lys Leu Ile Lys Ser Ile Asn Ala Leu Ser Pro Leu Ile Ser
225                 230                 235                 240

Ile Ala Ala Arg Phe Glu Leu Val Val Glu Lys Cys Val Asn Ser Gln
```

-continued

```
                245                 250                 255

Cys Val Met Ala Leu Arg Thr Gly Ser Lys Asn Asp Val Thr Ala Glu
            260                 265                 270

Arg Lys Val Arg Gly Leu Leu Ala Glu Leu Asp Asp Ser Leu Leu Lys
        275                 280                 285

Met Gly Gly Arg Thr Ser Phe Arg Gln Leu Ile Gly Thr Leu Glu Leu
    290                 295                 300

Ile Ala Glu Glu Gln Ser
305                 310
```